US011679180B2

(12) United States Patent
Marmorstein et al.

(10) Patent No.: US 11,679,180 B2
(45) Date of Patent: Jun. 20, 2023

(54) METHODS AND MATERIALS FOR USING FIBRIN SUPPORTS FOR RETINAL PIGMENT EPITHELIUM TRANSPLANTATION

(71) Applicant: Mayo Foundation for Medical Education and Research, Rochester, MN (US)

(72) Inventors: Alan D. Marmorstein, Rochester, MN (US); Raymond Iezzi, Rochester, MN (US); Jarel K. Gandhi, Rochester, MN (US); Jose S. Pulido, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 684 days.

(21) Appl. No.: 16/467,681

(22) PCT Filed: Nov. 13, 2017

(86) PCT No.: PCT/US2017/061300
§ 371 (c)(1),
(2) Date: Jun. 7, 2019

(87) PCT Pub. No.: WO2018/106414
PCT Pub. Date: Jun. 14, 2018

(65) Prior Publication Data
US 2020/0061246 A1 Feb. 27, 2020

Related U.S. Application Data

(60) Provisional application No. 62/431,259, filed on Dec. 7, 2016.

(51) Int. Cl.
| | |
|---|---|
| A61L 27/38 | (2006.01) |
| C12N 5/079 | (2010.01) |
| A61K 35/36 | (2015.01) |
| A61K 35/30 | (2015.01) |
| A61K 38/36 | (2006.01) |
| A61K 38/48 | (2006.01) |
| A61L 27/22 | (2006.01) |
| A61L 27/52 | (2006.01) |
| A61L 27/34 | (2006.01) |
| A61L 27/36 | (2006.01) |

(52) U.S. Cl.
CPC .......... *A61L 27/3813* (2013.01); *A61K 35/30* (2013.01); *A61K 35/36* (2013.01); *A61K 38/363* (2013.01); *A61K 38/484* (2013.01); *A61L 27/225* (2013.01); *A61L 27/34* (2013.01); *A61L 27/3687* (2013.01); *A61L 27/3808* (2013.01); *A61L 27/3839* (2013.01); *A61L 27/52* (2013.01); *C12N 5/0621* (2013.01); *C12Y 304/21007* (2013.01); *A61L 2420/02* (2013.01); *A61L 2430/16* (2013.01); *C12N 2501/734* (2013.01); *C12N 2501/999* (2013.01); *C12N 2506/45* (2013.01); *C12N 2533/56* (2013.01); *C12N 2533/90* (2013.01)

(58) Field of Classification Search
None
See application file for complete search history.

(56) References Cited

U.S. PATENT DOCUMENTS

| | | |
|---|---|---|
| 6,045,791 A | 4/2000 | Liu |
| 6,179,826 B1 | 1/2001 | Aebischer et al. |
| 6,413,245 B1 | 7/2002 | Yaacobi et al. |
| 6,607,522 B1 | 8/2003 | Hamblin et al. |
| 8,231,908 B2 | 7/2012 | Kinoshita |
| 8,425,473 B2 | 4/2013 | Ho et al. |
| 2004/0115176 A1 | 6/2004 | Swartz et al. |
| 2004/0236343 A1 | 11/2004 | Taylor et al. |
| 2006/0047250 A1 | 3/2006 | Hickingbotham et al. |
| 2007/0060887 A1 | 3/2007 | Marsh et al. |
| 2007/0225631 A1 | 9/2007 | Bowlin et al. |
| 2007/0237757 A1 | 10/2007 | Wyatt et al. |
| 2008/0097335 A1 | 4/2008 | Trogden et al. |
| 2009/0270487 A1 | 10/2009 | Wyatt et al. |
| 2010/0284998 A1 | 11/2010 | Smith et al. |
| 2010/0291058 A1 | 11/2010 | Bowlin et al. |
| 2011/0171185 A1 | 7/2011 | Klimanskaya et al. |
| 2011/0269173 A1 | 11/2011 | Zhu et al. |
| 2012/0207723 A1 | 8/2012 | He et al. |
| 2012/0219737 A1 | 8/2012 | Sugino et al. |
| 2012/0269776 A1 | 10/2012 | Alaminos Mingorance et al. |
| 2013/0004469 A1 | 1/2013 | Glazier et al. |

(Continued)

FOREIGN PATENT DOCUMENTS

| | | |
|---|---|---|
| AU | 4802901 | 8/2001 |
| CN | 103007355 | 4/2013 |

(Continued)

OTHER PUBLICATIONS

Singh. Sukhjit; et al; "Natural and artificial substrates for retinal pigment epithelial monolayer transplantation" Biomaterials, 22, 3337-3343, 2001 (Year: 2001).*

Yaji, Naoko; et al; "Transplantation of tissue-engineered retinal pigment epithelial cell sheets in a rabbit model" Biomaterials, 30, 797-803, 2009 (Year: 2009).*

(Continued)

*Primary Examiner* — David W Berke-Schlessel
(74) *Attorney, Agent, or Firm* — Fish & Richardson P.C.

(57) ABSTRACT

This document provides methods and materials for performing retinal pigment epithelium transplantation. For example, methods and materials for using fibrin supports for retinal pigment epithelium transplantation are provided.

18 Claims, 47 Drawing Sheets
Specification includes a Sequence Listing.

(56) References Cited

U.S. PATENT DOCUMENTS

| | | |
|---|---|---|
| 2013/0046382 A1 | 2/2013 | Mazzocchi et al. |
| 2013/0218167 A1 | 8/2013 | Coffey et al. |
| 2013/0253405 A1 | 9/2013 | Tu |
| 2013/0295060 A1 | 11/2013 | Yang et al. |
| 2013/0345618 A1 | 12/2013 | Auld et al. |
| 2014/0057281 A1 | 2/2014 | Takahashi et al. |
| 2014/0234381 A1 | 8/2014 | Tao et al. |
| 2015/0032223 A1 | 1/2015 | Miyagawa et al. |
| 2015/0118200 A1 | 4/2015 | Sugino et al. |
| 2015/0132847 A1 | 5/2015 | Lipke et al. |
| 2015/0147768 A1 | 5/2015 | Chan et al. |
| 2015/0159134 A1 | 6/2015 | Choudhary et al. |
| 2015/0368713 A1 | 12/2015 | Bharti et al. |
| 2016/0058908 A1 | 3/2016 | Oohashi et al. |
| 2016/0168523 A1 | 6/2016 | Glazier et al. |
| 2016/0331867 A1 | 11/2016 | Chiou |
| 2016/0346006 A1 | 12/2016 | Hickengbotham et al. |
| 2017/0067017 A1 | 3/2017 | Meyer et al. |
| 2017/0246350 A1 | 8/2017 | Du et al. |
| 2018/0049918 A1 | 2/2018 | Benner et al. |
| 2019/0000669 A1 | 1/2019 | Hammack et al. |
| 2019/0169569 A1 | 6/2019 | Bharti et al. |
| 2020/0157497 A1 | 5/2020 | Marmorstein |
| 2022/0000664 A1 | 1/2022 | Gandhi et al. |

FOREIGN PATENT DOCUMENTS

| | | |
|---|---|---|
| CN | 103656742 | 3/2014 |
| CN | 110520139 | 11/2019 |
| CN | 114807035 | 7/2022 |
| EP | 0700429 | 10/2000 |
| EP | 2554661 | 4/2008 |
| EP | 3551216 | 10/2019 |
| JP | H09-501303 | 2/1997 |
| JP | 2006501848 | 1/2006 |
| JP | 2007524411 | 8/2007 |
| JP | 2013502234 | 1/2013 |
| JP | 2013502915 | 1/2013 |
| JP | 2016052271 | 4/2016 |
| WO | WO 94/25569 | 11/1994 |
| WO | WO 2005/090550 | 9/2005 |
| WO | WO 2007/013331 | 2/2007 |
| WO | WO 2007/119213 | 10/2007 |
| WO | WO 2014/106136 | 7/2014 |
| WO | WO 2014/121077 | 8/2014 |
| WO | WO 2015/077498 | 5/2015 |
| WO | WO 2015/087231 | 6/2015 |
| WO | WO 2016/047849 | 3/2016 |
| WO | WO 2016/062862 | 4/2016 |
| WO | WO 2017/044488 | 3/2017 |
| WO | WO 2018/106414 | 6/2018 |

OTHER PUBLICATIONS

Age-Related Macular Degeneration (AMD) National Eye Institute, (n.d.). https://nei.nih.gov/eyedata/amd#5 (accessed Sep. 14, 2016).

Brandl et al., "In-Depth Characterisation of Retinal Pigment Epithelium (RPE) Cells Derived from Human Induced Pluripotent Stem Cells (hiPSC)," NeuroMolecular Med., 16(3):551-64, Sep. 2014.

Carr et al., "Molecular characterization and functional analysis of phagocytosis by human embryonic stem cell-derived RPE cells using a novel human retinal assay," Mol. Vis., 15:283-95, Feb. 2009.

Chaurasia et al., "Optimization of Fibrin Glue Spray Systems for Ophthalmic Surgery," Transl. Vis. Sci. Technol., 1(2):2, Jun. 2012.

Dalvin et al., "Vitelliform dystrophies: Prevalence in Olmsted County, Minnesota, United States," Ophthalmic Genet., 38(2):143-7, Mar. 2016.

Diniz et al., "Subretinal Implantation of Retinal Pigment Epithelial Cells Derived From Human Embryonic Stem Cells: Improved Survival When Implanted as a Monolayer," Invest. Ophthalmol. Vis. Sci., 54(7):5087-96, Jul. 2013.

Filho et al., "Grid laser photocoagulation in the treatment of serous avascular pigment epithelial detachment in age-related macular degeneration," Arq. Bass. Oitalmol., 77(5):315-20, 2014.

Filová et al., "Vascular endothelial cells on two-and three-dimensional fibrin assemblies for biomaterial coatings," J. Biomed. Mater. Res. A., 90A(1):55-69, Jun. 2009.

Hou et al., "In vivo and in vitro study of suprachoroidal fibrin glue," Jpn. J. Opththalmol., 53(6):640-7, Nov. 2009.

Hu et al., "A Novel Approach for Subretinal Implantation of Ultrathin Substrates Containing Stem Cell-Derived Retinal Pigment Epithelium Monolayer," Ophthalmic Res., 48(4):186-91, Oct. 2012.

Idelson et al., "Directed Differentiation of Human Embryonic Stem Cells into Functional Retinal Pigment Epithelium Cells," Cell Stem Cell., 5(4):396-408, Oct. 2009.

Jayaram et al., Stem Cell and Encapsulated Drug Delivery to the Inner Retina using a Fibrin Polymer Spray System 54(15):4686, Jun. 2013, (Abstract).

Johnson et al., "Autosomal Recessive Bestrophinopathy Is Not Associated With the Loss of Bestrophin-1 Anion Channel Function in a Patient With a Novel BEST1 Mutation," Ophthalmol. Vis. Sci., 56(8):4619-30, Jul. 2015.

Kamao et al., "Characterization of Human Induced Pluripotent Stem Cell-Derived Retinal Pigment Epithelium Cell Sheets Aiming for Clinical Application," Stem Cell Rep., 2(2):205-18, Feb. 2014.

Lai et al., "Characterization of Cross-Linked Porous Gelatin Carriers and Their Interaction with Corneal Endothelium: Biopolymer Concentration Effect," PLoS ONE, 8(1):e54058, Jan. 2013.

Lu et al., "Mesh-supported submicron parylene-C membranes for culturing retinal pigment epithelial cells," Biomed. Microdevices, 14(4):659-67, Aug. 2012.

Mandai et al., "Autologous Induced Stem-Cell-Derived Retinal Cells for Macular Degeneration," N. Eng. J. Med., 376(11):1038-46, Mar. 2017.

McHugh et al., "Porous Poly($\varepsilon$-Caprolactone) Scaffolds for Retinal Pigment Epithelium Transplantation," Invest. Ophthalmol. Vis. Sci., 55(3):1754-62, Mar. 2014.

Medcell.med.yale.edu [online], "Cell Biology," Jan. 11, 2012 Retrieved from URL:<http://medcell.med.yale.edu/lectures/epithelial_structure.php> 5 pages, retrieved on Sep. 4, 2019.

Mishra et al., "Effect of prevascularization on in vivo vascularization of poly (propylene fumarate)/fibrin scaffolds," Biomaterials, 77:255-66, Jan. 2016.

Moya et al., "Microfluidic device to culture 3D in vitro human capillary networks," Methods Mol. Biol., 1202:21-7, Jan. 2014.

PCT International Preliminary Report on Patentability in International Appln. No. PCT/US2017/061300 dated Jun. 11, 2019, 10 pages.

PCT International Search Report and Written Opinion in International Appln. No. PCT/US2017/061300 dated Feb. 6, 2018, 13 pages.

Peyman et al., "A technique for retinal pigment epithelium transplantation for age-related macular degeneration secondary to extensive subfoveal scarring," Ophthalmic Surg., 22(2):102-8, Feb. 1991.

Pinnock et al., "Customizable engineered blood vessels using 3D printed inserts," Methods, 99:20-7, Apr. 2016.

Roider et al., "Response of the Retinal Pigment Epithelium to Selective Photocoagulation," Arch Ophthalmol., 110(12):1786-92, 1992.

Roth, "Recombinant tissue plasminogen activator for the treatment of acute ischemic stroke," Bayl. Univ. Med. Cent. Proc., 24(3)257-9, 2011.

Rowe et al., "Influence of thrombin concentration on the mechanical and morphological properties of cell-seeded fibrin hydrogels," Acta Biomater., 3(1):59-67, Jan. 2007.

Schwartz et al., "Embryonic stem cell trials for macular degeneration: a preliminary report," Lancet, 379(9817):713-20, Feb. 2012.

Schwartz et al., "Human embryonic stem cell-derived retinal pigment epithelium in patients with age-related macular degeneration and Stargardt's macular dystrophy: follow-up of two open-label phase 1/2 studies," Lancet., 385(9967):509-16, Feb. 2015.

Schwartz et al., "Subretinal Transplantation of Embryonic Stem Cell-Derived Retinal Pigment Epithelium for the Treatment of

(56) References Cited

OTHER PUBLICATIONS

Macular Degeneration: An Assessment at 4 Years," Invest. Ophthalmol. Vis. Sci., 57(5):ORSFc1-9, Apr. 2016.
Singh et al., "Functional analysis of serially expanded human iPS cell-derived RPE cultures," Ophthalmol. Vis. Sci., 54(10):6767-78, Oct. 2013.
Sonoda et al., "A protocol for the culture and differentiation of highly polarized human retinal pigment epithelial cells," Nat. Protoc., 4(5):662-673, Apr. 2009.
Stanzel et al., "Human RPE Stem Cells Grown into Polarized RPE Monolayers on a Polyester Matrix are Maintained after Grafting into Rabbit Subretinal Space," Stem Cell Rep., 2(1):64-77, Jan. 2014.
Sun et al., "Protective Effects of Human iPS-Derived Retinal Pigmented Epithelial Cells in Comparison with Human Mesenchymal Stromal Cells and Human Neural Stem Cells on the Degenerating Retina in rd1 mice," Stem Cells, 33(5):1543-53, Feb. 2015.
Tababat-Khani et al., "Photocoagulation of human retinal pigment epithelium in vitro: unravelling the effects on ARPE-19 by transcriptomics and proteomics," Acta Ophthalmol., 93(4):348-54, Jun. 2015.
Uehara et al., "Effect of Fibrin Formulation on Initial Strength of Tendon Repair and Migration of Bone Marrow Stromal Cells in Vitro," J. Bone Joint Surg. Am., 97(21):1792-8, Nov. 2015.
Undas et al., "A Role in the Pathophysiology of Arterial and Venous Thromboembolic Diseases," Arterioscler. Thromb. Vasc. Biol., 31:e88-99, Aug. 2011.
Ye et al., "Primer-BLAST: A tool to design target-specific primers for polymerase chain reaction," BMC Bioinformatics, 13(1):134, Jun. 2012.
Zarbin, "Cell-Based Therapy for Degenerative Retinal Disease," Trends Mol. Med., 22(2):P115-34., Feb. 2016.
Ahmed et al., "Autologous fibrin glue as an encapsulating scaffold for delivery of retinal progenitor cells," Front. Bioeng. Biotechnology, Feb. 3, 2015, 2:85, 11 pages.
Mooney et al., "Specific Fibrinogen and Thrombin Concentrations Promote Neuronal Rather Than Glial Growth When Primary Neural Cells are Seeded Within Plasma-Derived Fibrin Gels," Tissue Eng. Part A, May 1, 2010, 16(5):1607-1619.
Algvere et al., "Transplantation of RPE in age-related macular degeneration: observations in disciform lesions and dry RPE atrophy," Graefes Arch. Clin. Exp. Ophthalmology, Mar. 1997, 235(3):149-158.
Chowdhury et al., "A Novel Rat Model to Study the Role of Intracranial Pressure Modulation on Optic Neuropathies," PLoS One, Dec. 2013, 8(12):e82151, 8 pages.
Da Cruz et al., "Phase 1 clinical study of an embryonic stem cell-derived retinal pigment epithelium patch in age-related macular degeneration," Nat. Biotechnology. Apr. 2018, 36(4):328-337.
De Boer et al., "Fibrin and activated platelets cooperatively guide stem cells to a vascular injury and promote differentiation towards an endothelial cell phenotype," Arteriosclerosis, Thrombosis, and Vascular Biology, 26(7):1653-9, Jul. 2006.
Fernandes et al., "Development of a new tissue injector for subretinal transplantation of human embryonic stem cell derived retinal pigmented epithelium," Int. J. Retin. Vitreous, Oct. 2017, 3:41, 9 pages.
Kamao et al., "Evaluation of the Surgical Device and Procedure for Extracellular Matrix—Scaffold-Supported Human iPSC—Derived Retinal Pigment Epithelium Cell Sheet Transplantation," Invest Ophthalmol. Vis. Science, Jan. 2017, 58(1):211-220.
Kashani et al., "A bioengineered retinal pigment epithelial monolayer for advanced, dry age-related macular degeneration," Sci. Transl. Medicine, Apr. 4, 2018, 10(435):eaao4097, 11 pages.
Najafabadi et al., "Behavior of a spontaneously arising human retinal pigment epithelial cell line cultivated on thin alginate film," Journal of Ophthalmic & Vision Research, 10(3):286-94, Jul. 2015.
Oganesian et al., "A new model of retinal pigment epithelium transplantation with microspheres," Archives of Ophthalmology, 117(9):1192-200, Sep. 1999.

Rowland et al., "Differentiation of human pluripotent stem cells to retinal pigmented epithelium in defined conditions using purified extracellular matrix proteins," Journal of Tissue Engineering and Regenerative Medicine, 7(8):642-53, Aug. 2013.
Sharma et al., "Clinical-grade stem cell-derived retinal pigment epithelium patch rescues retinal degeneration in rodents and pigs," Sci. Transl. Medicine, Jan. 16, 2019, 11(475):eaat5580, 47 pages.
Stanzel et al. "Subretinal Delivery of Ultrathin Rigid-Elastic Cell Carriers Using a Metallic Shooter Instrument and Biodegradable Hydrogel Encapsulation," Invest Ophthalmol. Vis. Science, Jan. 2012, 53(1):490-500.
Ausubel et al., "GMP scale-up and banking of pluripotent stem cells for cellular therapy applications," InHuman Pluripotent Stem Cells, Humana Press, 2011:147-59, 2011.
Blombäck, "Fibrinogen structure, activation, polymerization and fibrin gel structure," Thromb Res., 75(3):327-328, 1994.
Calejo et al., "Honeycomb porous films as permeable scaffold materials for human embryonic stem cell-derived retinal pigment epithelium," Journal of Biomedical Materials Research Part A 104.7 (2016):1646-1656.
Chen et al., "Considerations in designing systems for large scale production of human cardiomyocytes from pluripotent stem cells," Stem cell research & therapy, 5(1):12, Mar. 2014.
Del Priore et al., "Survival of allogeneic porcine retinal pigment epithelial sheets after subretinal transplantation," Invest Ophthalmol, Vis. Sci., 45(3):985-992, 2004.
Eaker et al., "Concise review: Guidance in developing commercializable autologous/patient-specific cell therapy manufacturing," Stem cells translational medicine, (11):871-83, Nov. 2013.
Fitzpatrick et al., "PNIPAAm-grafted-collagen as an injectable, in situ gelling, bioactive cell delivery scaffold," Biomacromolecules, 11(9):2261-7, Sep. 2010.
Gandhi et al., "Differential intraocular pressure measurements by tonometry and direct cannulation after treatment with soluble adenylyl cyclase inhibitors," Journal of Ocular Pharmacology and Therapeutics, 33(8):574-81, Oct. 2017.
Gandhi et al., "Fibrin hydrogels as a xenofree and rapidly degradable support for transplantation of retinal pigment epithelium monolayers," Acta. biomaterialia., 67:134-46, Feb. 2018.
Inoue et al., "iPS cells: a game changer for future medicine," The EMBO journal, 33(5):409-17, Mar. 2014.
Johnson et al., "Disease modeling studies using induced pluripotent stem cells: are we using enough controls?" Regen Med., 899-903, Dec. 2017.
Koss et al., "Subretinal implantation of a monolayer of human embryonic stem cell-derived retinal pigment epithelium: a feasibility and safety study in Yucatan minipigs," Graefe's Archive for Clinical and Experimental Ophthalmology, 254(8):1553-65, Aug. 2016.
Lam et al., "Improved human pluripotent stem cell attachment and spreading on xeno-free laminin-521-coated microcarriers results in efficient growth in agitated cultures," BioResearch open access, 4(1):242-57, Apr. 2015.
Lu et al., "A defined xeno-free and feeder-free culture system for the derivation, expansion and direct differentiation of transgene-free patient-specific induced pluripotent stem cells," Biomaterials, 35(9):2816-26, Mar. 2014.
Machin and Mackie, "Routine measurement of fibrinogen concentration," BMJ, 307(6909):882-883, Oct. 1993.
Mackie et al., "Haemostasis and Thrombosis Task Force of the British Committee for Standards in Haematology. Guidelines on fibrinogen assays," British journal of haematology, 121(3):396-404, May 2003.
Miyazaki et al., "Recombinant human laminin isoforms can support the undifferentiated growth of human embryonic stem cells," Biochemical and biophysical research communications, 375(1):27-32, Oct. 2008.
Neofytou et al., "Hurdles to clinical translation of human induced pluripotent stem cells," The Journal of clinical investigation, 125(7):2551-7, Jul. 2015.

(56) References Cited

OTHER PUBLICATIONS

Reyes et al., "Xeno-free and defined human embryonic stem cell-derived retinal pigment epithelial cells functionally integrate in a large-eyed preclinical model," Stem cell reports, 6(1):9-17, Jan. 2016.
Rezai et al., "Biodegradable polymer film as a source for formation of human fetal retinal pigment epithelium spheroids," Investigative ophthalmology & visual science, 40(6):1223-8, May 1999.
Takahashi et al., "Induction of pluripotent stem cells from adult human fibroblasts by defined factors," Cell, 131(5):861-72, Nov. 2007.
Unger et al., "Good manufacturing practice and clinical-grade human embryonic stem cell lines," Human molecular genetics, 17(R1):R48-53, Apr. 2008.
Xiang et al., "A novel Bruch's membrane-mimetic electrospun substrate scaffold for human retinal pigment epithelium cells," Biomaterials, 35(37):9777-88, Dec. 2014.
Yamanaka, "The winding road to pluripotency (Nobel Lecture)," Angewandte Chemie International Edition, 52(52):13900-9, Dec. 2013.
U.S. Appl. No. 16/618,579, filed Dec. 2, 2019, Alan D. Marmorstein.
Bhatt et al., "Experimental transplantation of human retinal pigment epithelial cells on collagen substrates," Am. J. Ophthalmology, Feb. 15, 1994, 117(2):214-221.
CA.gov [online], "Stem Cell Experts Discuss the Ethical Implications of Translating iPSCs to the Clinic," Sep. 27, 2016, retrieved on Apr. 22, 2022, retrieved from URL<https://blog.cirm.ca.gov/2016/09/27/stem-cell-experts-discuss-the-ethical-implications-of-translating-ipscs-to-the-clinic/>, 7 pages.
Collet et al., "Influence of fibrin network conformation and fibrin fiber diameter on fibrinolysis speed: dynamic and structural approaches by confocal microscopy," Arterioscler. Thromb. Vasc. Biology, May 2000, 20(5):1354-1361.
Cyranoski, "Japanese woman is first recipient of next-generation stem cells," Nature, Sep. 12, 2014, 2 pages.
Gabrielian et al., "Growth of human fetal retinal pigment epithelium as microspheres," Graefes Arch. Clin. Exp. Ophthalmology, Feb. 1999, 237(3):241-248.
Giordano et al., "Retinal pigment epithelium cells cultured on synthetic biodegradable polymers," J. Biomed. Mater. Research, Jan. 1997, 34(1):87-93.
RegMedNet.com [online], "Cell therapy commercialization: GMP and Scalability," Sep. 26, 2017, retrieved on Apr. 22, 2022, retrieved from URL<https://www.regmednet.com/cell-therapy-commercialization-gmp-and-scalability/>, 7 pages.
Taylor et al., "Controlled release of neurotrophin-3 from fibrin gels for spinal cord injury," J. Control. Release, Aug. 11, 2004, 98(2):281-294.
ThermoFisher, "Nunc Cell-culture treated Six-well plate description" https://www.thermofisher.com/order/catalog/product/140675, accessed Jan. 27, 2022 (Year: 2022).
Vaajasaari et al. "Toward the defined and xeno-free differentiation of functional human pluripotent stem cell-derived retinal pigment epithelial cells." Molecular Vision 17(2011): 558. (Year: 2011).
Warnke et al., "Primordium of an artificial Bruch's membrane made of nanofibers for engineering of retinal pigment epithelium cell monolayers," Acta Biomaterialia, Dec. 2013, 9(12):9414-9422.
U.S. Appl. No. 17/428,703, filed Aug. 5, 2021, Jarel K. Gandhi, Published as U.S. Patent Application Publication No. 2022/0000664.
German et al., "Retinal pigment epithelial cells promote spatial reorganization and differentiation of retinal photoreceptors," J. Neurosci. Research, 86(16):3503-3514, Dec. 2008.
Slaughter et al., "Antifibrinolytic drugs and perioperative hemostasis," Am. J. Hematology, 56(1):32-36, Sep. 1997.
Linsley et al., "The effect of fibrinogen, collagen type 1, and fibronectin on mesenchymal stem cell growth and differentiation into osteoblasts." Tissue Engineering Part A 19.11-12 (2013): 1416-1423. (Year: 2013).
Yunping, "[Comparison of growth of human retinal pigment epithelial cell on two prosthetic replacements of Bruch's membrane]," Dissertation, Central South University, 2010, 112 pages (with English Abstract).
Chen et al., "Approach discussion of the differentiation of stem cells induced to retinal pigment epithelial cells," Int. Eye Science, Oct. 8, 2020, 20(10):1722-1725 (with English abstract).
Gandhi et al., "Human Fibrinogen for Maintenance and Differentiation of Induced Pluripotent Stem Cells in Two Dimensions and Three Dimensions," Stem Cells Transl. Medicine, Feb. 15, 2019, 8(6):512-521.
Ji et al., "[Research progress on the differentiation of human induced pluripotent stem cells into retinal pigment epithelial cells and its application in clinical treatment]," China Med. Biotechnology, Aug. 10, 2017, 12(4):356-359, 368 (with English Abstract).
Yang et al., "Induced Pluripotent Stem Cells and Outer Retinal Disease," Stem Cells International, Jan. 15, 2016, 2016:2850873, 6 pages.
Zeng, "[Comparison of the biological characteristics of 2D and 3D induced human embryonic stem cell-derived retinal pigment epithelium]," Thesis, The Third Military Medical University, May 2016, 65 pages (with English Abstract).

\* cited by examiner

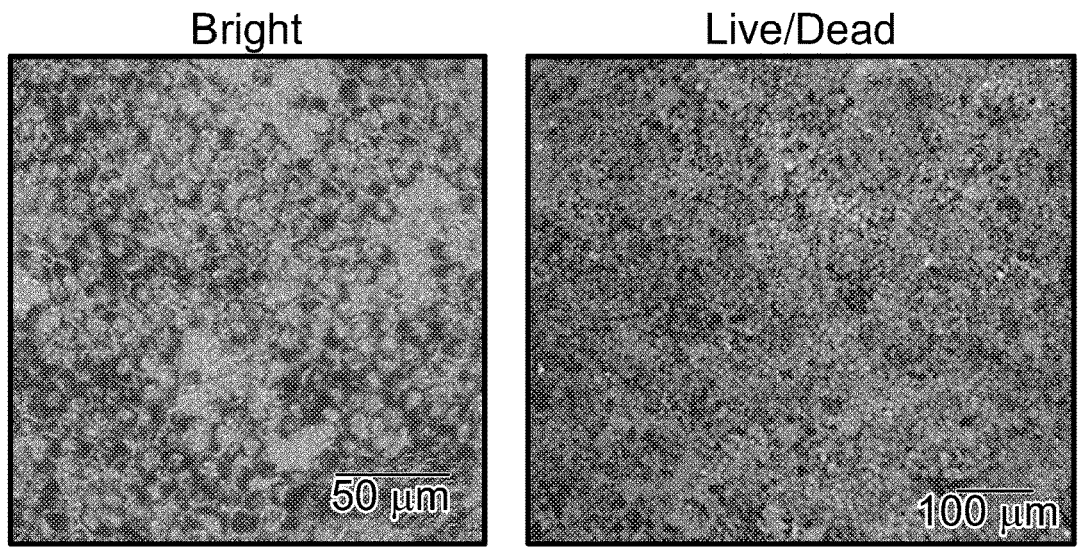
FIG. 38A
FIG. 38B
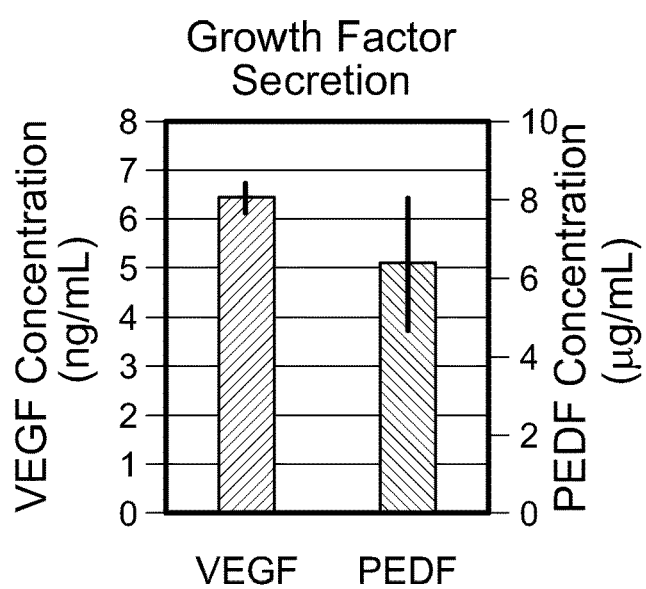
FIG. 38C
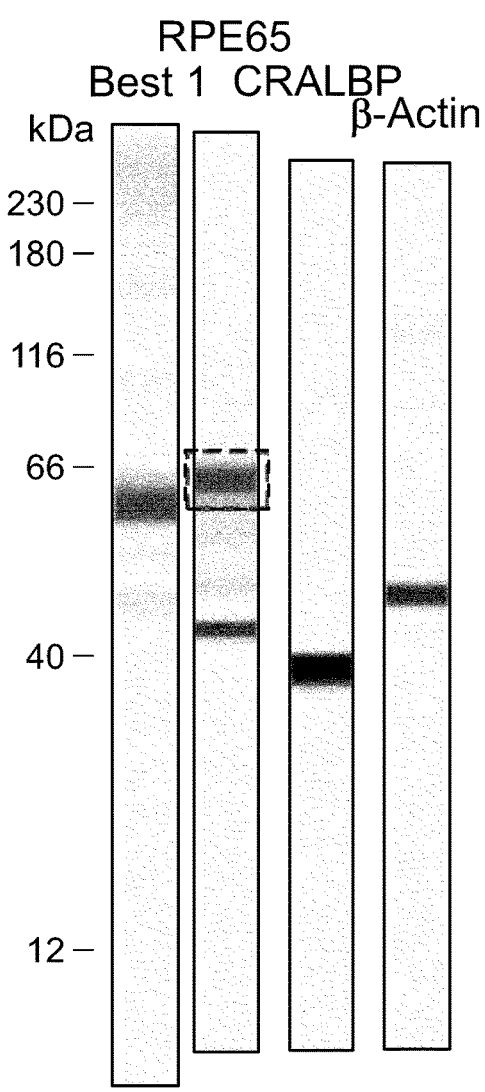
FIG. 38D

| Gene | iPSC-RPE on Fibrin | Amplicon Size | Forward Primer (SEQ ID NO:) | Reverse Primer (SEQ ID NO:) |
|---|---|---|---|---|
| RPE65 | + | 101 | AACTTGGGTTTGGCAAGAGC (1) | CCACACTCAGAACTACACCATCA (2) |
| 5' BEST1 | + | 359 | ATTTATAGGCTGGCCCTCACGGAA (3) | TGTTCTGCCGGAGTCATAAAGCCT (4) |
| 3' BEST1 | + | 125 | TGCCAGAGATCCCGAAAAT (5) | GGAATGTGCTTCATCCCTGTT (6) |
| MERTK | + | 172 | ACTGCCTGGATGAACTGTATGA (7) | GAGCTCTCCAGCAACTGTGT (8) |
| LRAT | + | 277 | TGGTCTCCAACAAGCGTCTC (9) | TCACAAAACTTGTCGGACTGG (10) |
| RDH5 (RDH) | + | 259 | CCTTCCTCACCAAGTACCTGAAA (11) | CTCTTGCTGGAAGGCTGGAT (12) |
| RLBP1 (CRALBP) | + | 122 | AAGCTGCTTGAGAGGGTCTTT (13) | ACGGCCTTGCCATCATACTT (14) |
| CRX | + | 150 | CCAGGGTTCAGGTTGGTTC (15) | CATCTGTGGAGGGTCTTGGG (16) |
| MITF | + | 142 | AATACAGGAACTTGAAATGCAGGC (17) | ATGCTGAAGGAGGTCTTGGC (18) |
| TFE3 | + | 130 | CGGGAGATCTCTGAGACCGA (19) | GGATGAGAGTGCCCAGTTCC (20) |
| TFEB | + | 159 | CGCATCAAGGAGTTGGGAAT (21) | CTCCAGGCGGGCGAGAGT (22) |
| MLANA | + | 181 | CTGCTTCATCGGCTGTTGGTA (23) | GAGCATTGGGAACCACAGGT (24) |
| PMEL | + | 127 | TGCCTGGGATTCTTCTCACAG (25) | TGCTTCATAAGTCTGCGCCTAT (26) |
| TYR | + | 324 | TTGACAGTATTTTGAGCAGTGGC (27) | GACACAGCAAGCTCACAAGC (28) |
| GPR143 (OA1) | + | 236 | TCTGAAGGTTCTGATGCCAGC (29) | GCTGGTGATGAGAGCAAGGT (30) |
| OCLN | + | 223 | AAGCAAGTGAAGGGATCTGC (31) | TCACAGAGGTTTGGCTTCCG (32) |

FIG. 40

| | | | |
|---|---|---|---|
| EZR | + | 307 | CGCTCTAAGGGTTCTGCTCT (33) | TCCTGGGCAGAGACACCTTCTTA (34) |
| CDH2 | + | 341 | ATCCTGCTTATCCTTGTGCTGA (35) | GGGTCATTGTCAGCCGCTTT (36) |
| ITGB5 | + | 306 | GGTGGACACCATCGTGAAAG (37) | GAAGCCATTTCATAGCGGGC (38) |
| ITGAV | + | 124 | AATGTCACCTGGGGCATTCA (39) | AAAAGCCCATCCTGTACATTACAAA (40) |
| SERPINF1 (PEDF) | + | 349 | CTTCAAGGGGCAGTGGGTAAC (41) | GGACTTGGTGACTTCGCCTT (42) |
| AQP11 | + | 110 | TCCGAACCAAGCTTCGTATC (43) | TAGCGAAAGTGCCAAAGCTG (44) |
| AQP1 | + | 134 | TGGACACCTCCTGGCTATTG (45) | GGGCCAGGATGAAGTCGTAG (46) |
| SLC16A8 (MCT3) | + | 119 | CTGCAGTTCGAGGTGCTCAT (47) | AGGGCGGCCGGCAGAG (48) |
| SLC16A1 (MCT1) | + | 242 | ACCACTTTAGGTCGGCTCA (49) | TCTGGTCCGAGATTCTGCT (50) |
| BSG (CD147,EMMPRIN) | + | 129 | AACTCTTCCTGAGGCAGGTGG (51) | GGAATCTACGGGGTGGGTTT (52) |
| HIF1A | + | 128 | GCCAGACGATCATGCAGCTA (53) | GCAGTCTACATGCTAAATCAGAGG (54) |
| OTX2 | + | 134 | TCGAGGGTGCAGGTATGGTT (55) | TCTGAACTCACTTCCCGAGC (56) |
| ACTB | + | 207 | GATCAAGATCATTGCTCCTCCTG (57) | CTGCGCAAGTTAGGTTTGTCA (58) |
| GAPDH | + | 109 | CTCTGCTCCTCCTGTTCGAC (59) | ACCAAATCGTTGACTCCGA (60) |
| LIN28A | - | 256 | AGATCAAAAGGAGACAGGTGCT (61) | AATAGCCCCCACCATTGTG (62) |
| NCAM | + | 157 | ACTGACGGAGCCCGAGAAG (63) | TTGCTCGGTTCTCTTCACCC (64) |
| CD36 | + | 125 | TTGGCTTAATGAGACTGGGACC (65) | ACATCACCACCACCAACACTGA (66) |

FIG. 40 (Cont.)

| NANOG | + | GTGACGCAGAAGGCCTCA (67) | TGCACCAGGTCTGAGTGTTC (68) |
|---|---|---|---|
| SeV | - | GGATCACTAGGTGATATCGAGC (69) | ACCAGACAAGAGTTTAAGAGATATGTATC (70) |
| SeV KLF | - | TTCCTGCATGCCAGAGGAGCCC (71) | AATGTATCGAAGGTGCTCAA (72) |
| SeV KOS | - | ATGCACCGGCTACGACGTGAGCGC (73) | ACCTTGACAATCCTGATGTGG (74) |
| SeV c-myc | - | TAACTGACTAGCAGGCTTGTCG (75) | TCCACATACAGTCCTGGATGATGATG (76) |

FIG. 40 (Cont.)

Insert Device (Side)

Insert Device (Top)

Insert Device (with Membrane)

15mm max

Green Piece Screws in to Hold Membrane in Place.

SEQUENCE LISTING

<160> NUMBER OF SEQ ID NOS: 76

<210> SEQ ID NO 1
<211> LENGTH: 20
<212> TYPE: DNA
<213> ORGANISM: Artificial
<220> FEATURE:
<223> OTHER INFORMATION: synthetic oligonucleotide

<400> SEQUENCE: 1
aacttgggtt tggcaagagc                                                       20

<210> SEQ ID NO 2
<211> LENGTH: 23
<212> TYPE: DNA
<213> ORGANISM: Artificial
<220> FEATURE:
<223> OTHER INFORMATION: synthetic oligonucleoti

<400> SEQUENCE: 2
ccacactcag aactacacca tca                                                   23

<210> SEQ ID NO 3
<211> LENGTH: 24
<212> TYPE: DNA
<213> ORGANISM: Artificial
<220> FEATURE:
<223> OTHER INFORMATION: synthetic oligonucleotide

<400> SEQUENCE: 3
atttataggc tggccctcac ggaa                                                  24

<210> SEQ ID NO 4
<211> LENGTH: 24
<212> TYPE: DNA
<213> ORGANISM: Artificial
<220> FEATURE:
<223> OTHER INFORMATION: synthetic oligonucleotide

<400> SEQUENCE: 4
tgttctgccg gagtcataaa gcct                                                  24

<210> SEQ ID NO 5
<211> LENGTH: 20
<212> TYPE: DNA
<213> ORGANISM: Artificial
<220> FEATURE:
<223> OTHER INFORMATION: synthetic oligonucleotide

<400> SEQUENCE: 5
tgccagagat ccccgaaaat                                                       20

<210> SEQ ID NO 6
<211> LENGTH: 21
<212> TYPE: DNA
<213> ORGANISM: Artificial
<220> FEATURE:
<223> OTHER INFORMATION: synthetic oligonucleotide

<400> SEQUENCE: 6
ggaatgtgct tcatccctgt t                                                     21

<210> SEQ ID NO 7
<211> LENGTH: 22
<212> TYPE: DNA
<213> ORGANISM: Artificial

```
<220> FEATURE:
<223> OTHER INFORMATION: synthetic oligonucleotide

<400> SEQUENCE: 7
actgcctgga tgaactgtat ga                                          22

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
gagctctcca gcaactgtgt                                             20

<210> SEQ ID NO 9
<211> LENGTH: 20
<212> TYPE: DNA
<213> ORGANISM: Artificial
<220> FEATURE:
<223> OTHER INFORMATION: synthetic oligonucleotide

<400> SEQUENCE: 9
tggtctccaa caagcgtctc                                             20

<210> SEQ ID NO 10
<211> LENGTH: 21
<212> TYPE: DNA
<213> ORGANISM: Artificial
<220> FEATURE:
<223> OTHER INFORMATION: synthetic oligonucleotide

<400> SEQUENCE: 10
tcacaaaact tgtcggactg g                                           21

<210> SEQ ID NO 11
<211> LENGTH: 23
<212> TYPE: DNA
<213> ORGANISM: Artificial
<220> FEATURE:
<223> OTHER INFORMATION: synthetic oligonucleotide

<400> SEQUENCE: 11
ccttcctcac caagtacctg aaa                                         23

<210> SEQ ID NO 12
<211> LENGTH: 20
<212> TYPE: DNA
<213> ORGANISM: Artificial
<220> FEATURE:
<223> OTHER INFORMATION: synthetic oligonucleotide

<400> SEQUENCE: 12
ctcttgctgg aaggctggat                                             20

<210> SEQ ID NO 13
<211> LENGTH: 21
<212> TYPE: DNA
<213> ORGANISM: Artificial
<220> FEATURE:
<223> OTHER INFORMATION: synthetic oligonucleotide

<400> SEQUENCE: 13
aagctgcttg agagggtctt t                                           21
```

```
<210> SEQ ID NO 14
<211> LENGTH: 20
<212> TYPE: DNA
<213> ORGANISM: Artificial
<220> FEATURE:
<223> OTHER INFORMATION: synthetic oligonucleotide

<400> SEQUENCE: 14
acggccttgc catcatactt                                               20

<210> SEQ ID NO 15
<211> LENGTH: 20
<212> TYPE: DNA
<213> ORGANISM: Artificial
<220> FEATURE:
<223> OTHER INFORMATION: synthetic oligonucleotide

<400> SEQUENCE: 15
ccagggttca ggtttggttc                                               20

<210> SEQ ID NO 16
<211> LENGTH: 20
<212> TYPE: DNA
<213> ORGANISM: Artificial
<220> FEATURE:
<223> OTHER INFORMATION: synthetic oligonucleotide

<400> SEQUENCE: 16
catctgtgga gggtcttggg                                               20

<210> SEQ ID NO 17
<211> LENGTH: 24
<212> TYPE: DNA
<213> ORGANISM: Artificial
<220> FEATURE:
<223> OTHER INFORMATION: synthetic oligonucleotide

<400> SEQUENCE: 17
aatacaggaa cttgaaatgc aggc                                          24

<210> SEQ ID NO 18
<211> LENGTH: 20
<212> TYPE: DNA
<213> ORGANISM: Artificial
<220> FEATURE:
<223> OTHER INFORMATION: synthetic oligonucleotide

<400> SEQUENCE: 18
atgctgaagg aggtcttggc                                               20

<210> SEQ ID NO 19
<211> LENGTH: 20
<212> TYPE: DNA
<213> ORGANISM: Artificial
<220> FEATURE:
<223> OTHER INFORMATION: synthetic oligonucleotide

<400> SEQUENCE: 19
cgggagatct ctgagaccga                                               20

<210> SEQ ID NO 20
<211> LENGTH: 20
<212> TYPE: DNA
<213> ORGANISM: Artificial
<220> FEATURE:
<223> OTHER INFORMATION: synthetic oligonucleotide
```

```
<400> SEQUENCE: 20
ggatgagagt gcccagttcc                                              20

<210> SEQ ID NO 21
<211> LENGTH: 20
<212> TYPE: DNA
<213> ORGANISM: Artificial
<220> FEATURE:
<223> OTHER INFORMATION: synthetic oligonucleotide

<400> SEQUENCE: 21
cgcatcaagg agttgggaat                                              20

<210> SEQ ID NO 22
<211> LENGTH: 17
<212> TYPE: DNA
<213> ORGANISM: Artificial
<220> FEATURE:
<223> OTHER INFORMATION: synthetic oligonucleotide

<400> SEQUENCE: 22
ctccaggcgg cgagagt                                                 17

<210> SEQ ID NO 23
<211> LENGTH: 20
<212> TYPE: DNA
<213> ORGANISM: Artificial
<220> FEATURE:
<223> OTHER INFORMATION: synthetic oligonucleotide

<400> SEQUENCE: 23
ctgctcatcg gctgttggta                                              20

<210> SEQ ID NO 24
<211> LENGTH: 20
<212> TYPE: DNA
<213> ORGANISM: Artificial
<220> FEATURE:
<223> OTHER INFORMATION: synthetic oligonucleotide

<400> SEQUENCE: 24
gagcattggg aaccacaggt                                              20

<210> SEQ ID NO 25
<211> LENGTH: 21
<212> TYPE: DNA
<213> ORGANISM: Artificial
<220> FEATURE:
<223> OTHER INFORMATION: synthetic oligonucleotide

<400> SEQUENCE: 25
tgcctgggat tcttctcaca g                                            21

<210> SEQ ID NO 26
<211> LENGTH: 22
<212> TYPE: DNA
<213> ORGANISM: Artificial
<220> FEATURE:
<223> OTHER INFORMATION: synthetic oligonucleotide

<400> SEQUENCE: 26
tgcttcataa gtctgcgcct at                                           22

<210> SEQ ID NO 27
```

```
<211> LENGTH: 24
<212> TYPE: DNA
<213> ORGANISM: Artificial
<220> FEATURE:
<223> OTHER INFORMATION: synthetic oligonucleotide

<400> SEQUENCE: 27
ttgacagtat ttttgagcag tggc                                            24

<210> SEQ ID NO 28
<211> LENGTH: 20
<212> TYPE: DNA
<213> ORGANISM: Artificial
<220> FEATURE:
<223> OTHER INFORMATION: synthetic oligonucleotide

<400> SEQUENCE: 28
gacacagcaa gctcacaagc                                                 20

<210> SEQ ID NO 29
<211> LENGTH: 21
<212> TYPE: DNA
<213> ORGANISM: Artificial
<220> FEATURE:
<223> OTHER INFORMATION: synthetic oligonucleotide

<400> SEQUENCE: 29
tctgaaggtt ctgatgccag c                                               21

<210> SEQ ID NO 30
<211> LENGTH: 20
<212> TYPE: DNA
<213> ORGANISM: Artificial
<220> FEATURE:
<223> OTHER INFORMATION: synthetic oligonucleotide

<400> SEQUENCE: 30
gctggtgatg agagcaaggt                                                 20

<210> SEQ ID NO 31
<211> LENGTH: 20
<212> TYPE: DNA
<213> ORGANISM: Artificial
<220> FEATURE:
<223> OTHER INFORMATION: synthetic oligonucleotide

<400> SEQUENCE: 31
aagcaagtga agggatctgc                                                 20

<210> SEQ ID NO 32
<211> LENGTH: 20
<212> TYPE: DNA
<213> ORGANISM: Artificial
<220> FEATURE:
<223> OTHER INFORMATION: synthetic oligonucleotide

<400> SEQUENCE: 32
tcacagaggt ttggcttccg                                                 20

<210> SEQ ID NO 33
<211> LENGTH: 20
<212> TYPE: DNA
<213> ORGANISM: Artificial
<220> FEATURE:
<223> OTHER INFORMATION: synthetic oligonucleotide

<400> SEQUENCE: 33
```

-continued cgctctaagg gttctgctct                                          20

<210> SEQ ID NO 34
<211> LENGTH: 21
<212> TYPE: DNA
<213> ORGANISM: Artificial
<220> FEATURE:
<223> OTHER INFORMATION: synthetic oligonucleotide

<400> SEQUENCE: 34
tcctgggcag acaccttctt a                                        21

<210> SEQ ID NO 35
<211> LENGTH: 22
<212> TYPE: DNA
<213> ORGANISM: Artificial
<220> FEATURE:
<223> OTHER INFORMATION: synthetic oligonucleotide

<400> SEQUENCE: 35
atcctgctta tccttgtgct ga                                       22

<210> SEQ ID NO 36
<211> LENGTH: 20
<212> TYPE: DNA
<213> ORGANISM: Artificial
<220> FEATURE:
<223> OTHER INFORMATION: synthetic oligonucleotide

<400> SEQUENCE: 36
gggtcattgt cagccgcttt                                          20

<210> SEQ ID NO 37
<211> LENGTH: 20
<212> TYPE: DNA
<213> ORGANISM: Artificial
<220> FEATURE:
<223> OTHER INFORMATION: synthetic oligonucleotide

<400> SEQUENCE: 37
ggtggacacc atcgtgaaag                                          20

<210> SEQ ID NO 38
<211> LENGTH: 20
<212> TYPE: DNA
<213> ORGANISM: Artificial
<220> FEATURE:
<223> OTHER INFORMATION: synthetic oligonucleotide

<400> SEQUENCE: 38
gaagccattt catagcgggc                                          20

<210> SEQ ID NO 39
<211> LENGTH: 20
<212> TYPE: DNA
<213> ORGANISM: Artificial
<220> FEATURE:
<223> OTHER INFORMATION: synthetic oligonucleotide

<400> SEQUENCE: 39
aatgtcacct ggggcattca                                          20

<210> SEQ ID NO 40
<211> LENGTH: 25
<212> TYPE: DNA

```
<213> ORGANISM: Artificial
<220> FEATURE:
<223> OTHER INFORMATION: synthetic oligonucleotide

<400> SEQUENCE: 40
aaaagcccat cctgtacatt acaaa                                          25

<210> SEQ ID NO 41
<211> LENGTH: 21
<212> TYPE: DNA
<213> ORGANISM: Artificial
<220> FEATURE:
<223> OTHER INFORMATION: synthetic oligonucleotide

<400> SEQUENCE: 41
cttcaagggg cagtgggtaa c                                              21

<210> SEQ ID NO 42
<211> LENGTH: 20
<212> TYPE: DNA
<213> ORGANISM: Artificial
<220> FEATURE:
<223> OTHER INFORMATION: synthetic oligonucleotide

<400> SEQUENCE: 42
ggacttggtg acttcgcctt                                                20

<210> SEQ ID NO 43
<211> LENGTH: 20
<212> TYPE: DNA
<213> ORGANISM: Artificial
<220> FEATURE:
<223> OTHER INFORMATION: synthetic oligonucleotide

<400> SEQUENCE: 43
tccgaaccaa gcttcgtatc                                                20

<210> SEQ ID NO 44
<211> LENGTH: 20
<212> TYPE: DNA
<213> ORGANISM: Artificial
<220> FEATURE:
<223> OTHER INFORMATION: synthetic oligonucleotide

<400> SEQUENCE: 44
tagcgaaagt gccaaagctg                                                20

<210> SEQ ID NO 45
<211> LENGTH: 20
<212> TYPE: DNA
<213> ORGANISM: Artificial
<220> FEATURE:
<223> OTHER INFORMATION: synthetic oligonucleotide

<400> SEQUENCE: 45
tggacacctc ctggctattg                                                20

<210> SEQ ID NO 46
<211> LENGTH: 20
<212> TYPE: DNA
<213> ORGANISM: Artificial
<220> FEATURE:
<223> OTHER INFORMATION: synthetic oligonucleotide

<400> SEQUENCE: 46
gggccaggat gaagtcgtag                                                20
```

<210> SEQ ID NO 47
<211> LENGTH: 20
<212> TYPE: DNA
<213> ORGANISM: Artificial
<220> FEATURE:
<223> OTHER INFORMATION: synthetic oligonucleotide

<400> SEQUENCE: 47
ctgcagttcg aggtgctcat                                       20

<210> SEQ ID NO 48
<211> LENGTH: 15
<212> TYPE: DNA
<213> ORGANISM: Artificial
<220> FEATURE:
<223> OTHER INFORMATION: synthetic oligonucleotide

<400> SEQUENCE: 48
aggcggccgg cagag                                            15

<210> SEQ ID NO 49
<211> LENGTH: 20
<212> TYPE: DNA
<213> ORGANISM: Artificial
<220> FEATURE:
<223> OTHER INFORMATION: synthetic oligonucleotide

<400> SEQUENCE: 49
accactttta ggtcggctca                                       20

<210> SEQ ID NO 50
<211> LENGTH: 20
<212> TYPE: DNA
<213> ORGANISM: Artificial
<220> FEATURE:
<223> OTHER INFORMATION: synthetic oligonucleotide

<400> SEQUENCE: 50
tctggtccgg agattctgct                                       20

<210> SEQ ID NO 51
<211> LENGTH: 21
<212> TYPE: DNA
<213> ORGANISM: Artificial
<220> FEATURE:
<223> OTHER INFORMATION: synthetic oligonucleotide

<400> SEQUENCE: 51
aactcttcct gaggcaggtg g                                     21

<210> SEQ ID NO 52
<211> LENGTH: 20
<212> TYPE: DNA
<213> ORGANISM: Artificial
<220> FEATURE:
<223> OTHER INFORMATION: synthetic oligonucleotide

<400> SEQUENCE: 52
ggaatctacg gggtgggttt                                       20

<210> SEQ ID NO 53
<211> LENGTH: 20
<212> TYPE: DNA
<213> ORGANISM: Artificial
<220> FEATURE:

```
<223> OTHER INFORMATION: synthetic oligonucleotide

<400> SEQUENCE: 53
gccagacgat catgcagcta                                              20

<210> SEQ ID NO 54
<211> LENGTH: 24
<212> TYPE: DNA
<213> ORGANISM: Artificial
<220> FEATURE:
<223> OTHER INFORMATION: synthetic oligonucleotide

<400> SEQUENCE: 54
gcagtctaca tgctaaatca gagg                                         24

<210> SEQ ID NO 55
<211> LENGTH: 20
<212> TYPE: DNA
<213> ORGANISM: Artificial
<220> FEATURE:
<223> OTHER INFORMATION: synthetic oligonucleotide

<400> SEQUENCE: 55
tcgagggtgc aggtatggtt                                              20

<210> SEQ ID NO 56
<211> LENGTH: 20
<212> TYPE: DNA
<213> ORGANISM: Artificial
<220> FEATURE:
<223> OTHER INFORMATION: synthetic oligonucleotide

<400> SEQUENCE: 56
tctgaactca cttcccgagc                                              20

<210> SEQ ID NO 57
<211> LENGTH: 23
<212> TYPE: DNA
<213> ORGANISM: Artificial
<220> FEATURE:
<223> OTHER INFORMATION: synthetic oligonucleotide

<400> SEQUENCE: 57
gatcaagatc attgctcctc ctg                                          23

<210> SEQ ID NO 58
<211> LENGTH: 22
<212> TYPE: DNA
<213> ORGANISM: Artificial
<220> FEATURE:
<223> OTHER INFORMATION: synthetic oligonucleotide

<400> SEQUENCE: 58
ctgcgcaagt taggttttgt ca                                           22

<210> SEQ ID NO 59
<211> LENGTH: 20
<212> TYPE: DNA
<213> ORGANISM: Artificial
<220> FEATURE:
<223> OTHER INFORMATION: synthetic oligonucleotide

<400> SEQUENCE: 59
ctctgctcct cctgttcgac                                              20
```

```
<210> SEQ ID NO 60
<211> LENGTH: 20
<212> TYPE: DNA
<213> ORGANISM: Artificial
<220> FEATURE:
<223> OTHER INFORMATION: synthetic oligonucleotide

<400> SEQUENCE: 60
accaaatccg ttgactccga                                           20

<210> SEQ ID NO 61
<211> LENGTH: 22
<212> TYPE: DNA
<213> ORGANISM: Artificial
<220> FEATURE:
<223> OTHER INFORMATION: synthetic oligonucleotide

<400> SEQUENCE: 61
agatcaaaag gagacaggtg ct                                        22

<210> SEQ ID NO 62
<211> LENGTH: 20
<212> TYPE: DNA
<213> ORGANISM: Artificial
<220> FEATURE:
<223> OTHER INFORMATION: synthetic oligonucleotide

<400> SEQUENCE: 62
aatagccccc acccattgtg                                           20

<210> SEQ ID NO 63
<211> LENGTH: 19
<212> TYPE: DNA
<213> ORGANISM: Artificial
<220> FEATURE:
<223> OTHER INFORMATION: synthetic oligonucleotide

<400> SEQUENCE: 63
actgacggag cccgagaag                                            19

<210> SEQ ID NO 64
<211> LENGTH: 20
<212> TYPE: DNA
<213> ORGANISM: Artificial
<220> FEATURE:
<223> OTHER INFORMATION: synthetic oligonucleotide

<400> SEQUENCE: 64
ttgctcggtt ctcttcaccc                                           20

<210> SEQ ID NO 65
<211> LENGTH: 22
<212> TYPE: DNA
<213> ORGANISM: Artificial
<220> FEATURE:
<223> OTHER INFORMATION: synthetic oligonucleotide

<400> SEQUENCE: 65
ttggcttaat gagactggga cc                                        22

<210> SEQ ID NO 66
<211> LENGTH: 21
<212> TYPE: DNA
<213> ORGANISM: Artificial
<220> FEATURE:
<223> OTHER INFORMATION: synthetic oligonucleotide
```

```
<400> SEQUENCE: 66
acatcaccac accaacactg a                                              21

<210> SEQ ID NO 67
<211> LENGTH: 18
<212> TYPE: DNA
<213> ORGANISM: Artificial
<220> FEATURE:
<223> OTHER INFORMATION: synthetic oligonucleotide

<400> SEQUENCE: 67
gtgacgcaga aggcctca                                                  18

<210> SEQ ID NO 68
<211> LENGTH: 20
<212> TYPE: DNA
<213> ORGANISM: Artificial
<220> FEATURE:
<223> OTHER INFORMATION: synthetic oligonucleotide

<400> SEQUENCE: 68
tgcaccaggt ctgagtgttc                                                20

<210> SEQ ID NO 69
<211> LENGTH: 22
<212> TYPE: DNA
<213> ORGANISM: Artificial
<220> FEATURE:
<223> OTHER INFORMATION: synthetic oligonucleotide

<400> SEQUENCE: 69
ggatcactag gtgatatcga gc                                             22

<210> SEQ ID NO 70
<211> LENGTH: 29
<212> TYPE: DNA
<213> ORGANISM: Artificial
<220> FEATURE:
<223> OTHER INFORMATION: synthetic oligonucleotide

<400> SEQUENCE: 70
accagacaag agtttaagag atatgtatc                                      29

<210> SEQ ID NO 71
<211> LENGTH: 22
<212> TYPE: DNA
<213> ORGANISM: Artificial
<220> FEATURE:
<223> OTHER INFORMATION: synthetic oligonucleotide

<400> SEQUENCE: 71
ttcctgcatg ccagaggagc cc                                             22

<210> SEQ ID NO 72
<211> LENGTH: 20
<212> TYPE: DNA
<213> ORGANISM: Artificial
<220> FEATURE:
<223> OTHER INFORMATION: synthetic oligonucleotide

<400> SEQUENCE: 72
aatgtatcga aggtgctcaa                                                20

<210> SEQ ID NO 73
<211> LENGTH: 23
```

```
<212> TYPE: DNA
<213> ORGANISM: Artificial
<220> FEATURE:
<223> OTHER INFORMATION: synthetic oligonucleotide

<400> SEQUENCE: 73
atgcaccgct acgacgtgag cgc                                         23

<210> SEQ ID NO 74
<211> LENGTH: 21
<212> TYPE: DNA
<213> ORGANISM: Artificial
<220> FEATURE:
<223> OTHER INFORMATION: synthetic oligonucleotide

<400> SEQUENCE: 74
accttgacaa tcctgatgtg g                                           21

<210> SEQ ID NO 75
<211> LENGTH: 22
<212> TYPE: DNA
<213> ORGANISM: Artificial
<220> FEATURE:
<223> OTHER INFORMATION: synthetic oligonucleotide

<400> SEQUENCE: 75
taactgacta gcaggcttgt cg                                          22

<210> SEQ ID NO 76
<211> LENGTH: 26
<212> TYPE: DNA
<213> ORGANISM: Artificial
<220> FEATURE:
<223> OTHER INFORMATION: synthetic oligonucleotide

<400> SEQUENCE: 76
tccacataca gtcctggatg atgatg                                      26
```

METHODS AND MATERIALS FOR USING FIBRIN SUPPORTS FOR RETINAL PIGMENT EPITHELIUM TRANSPLANTATION

This application is a National Stage application under 35 U.S.C. § 371 of International Application No. PCT/US2017/061300, having an International Filing Date of Nov. 13, 2017, which claims the benefit of U.S. Provisional Ser. No. 62/431,259, filed Dec. 7, 2016. This disclosures of the prior applications are considered part of (and are incorporated by reference in) the disclosure of this application.

BACKGROUND

1. Technical Field

This document relates to retinal pigment epithelium transplantation. For example, this document relates to methods and materials for using fibrin supports for retinal pigment epithelium transplantation.

2. Background Information

Macular degeneration diseases represent a variety of diseases and etiology, but commonly stem from retinal pigment epithelium (RPE) dysfunction. Genetic macular degenerations, including the bestrophinopathies, occur due to protein mutations involved in RPE function. The bestrophinopathies (e.g., Best's disease) arise from a mutation in the Best1 gene, causing RPE dysfunction leading to eventual photoreceptor death. The prevalence has previously been reported as 1 in 16,000-21,500 (Dalvin et al., *Ophthalmic Genet.*, Epub:1-5 (2016)). While the genetically-caused macular degenerations are rare, age-related macular degeneration (AMD) is the leading cause of blindness in the first world. It is estimated to account for 5 million cases in the US in 2050. AMD is a more complex disease of immune and vascular function that directly affects RPE function.

RPE replacement as a treatment for macular degeneration has been a popular focus in recent history. Modern advances in stem cell technologies have made embryonic (ES) and induced pluripotent (IPS) stem cells attractive candidates for transplantation. Multiple reports show the ability to differentiate both stem cell sources towards an RPE lineage (Sonoda et al., *Nat. Protoc.*, 4:662-673 (2009); Johnson et al., *Ophthalmol. Vis. Sci.*, 56:4619 (2015); Brandl et al., *NeuroMolecular Med.*, 16:551-564 (2014); Idelson et al., *Cell Stem Cell.*, 5:396-408 (2009); Carr et al., *Mol. Vis.*, 15:283-295 (2009)). Both ES-RPE and IPS-RPE have been shown to exhibit normal RPE function, including cell markers, phagocytosis, and pigmentation (Singh et al., *Ophthalmol. Vis. Sci.*, 54:6767-6778 (2013)).

SUMMARY

This document relates to RPE transplantation. While in vitro successes of RPE transplantation have been attained, many difficulties have risen in translation towards clinical application. The earliest trials attempted to deliver RPE single cell suspensions to the subretinal space in dry AMD patients (Peyman et al., *Ophthalmic Surg.*, 22:102-108 (1991); and Schwartz et al., *The Lancet.*, 379:713-720 (2012)). These studies showed safety efficacy, as no adverse reactions were reported (Schwartz et al., *The Lancet.*, 379: 713-720 (2012); Schwartz et al., *The Lancet.*, 385:509-516 (2015); and Schwartz et al., *Ophthalmol. Vis. Sci.*, 57:ORSFc1-9 (2016)). However, transplantation was characterized by low percentage of RPE attachment and survival. As expected, no major improvement was detected in visual acuity (Schwartz et al., *The Lancet.*, 385:509-516 (2015)).

As an epithelium, cell-cell contact is involved in RPE survival and function. Subsequent trials have focused on the growth of RPE monolayers for transplantation. A recent study utilized collagen gel culture of RPE and use of collagenase to detach the monolayer as a single unit prior to transplantation (Kamao et al., *Stem Cell Rep.*, 2:205-218 (2014); and Sun et al., *Stem Cells*, 33:1543-1553 (2015)). Animal studies transplanting the unsupported RPE monolayer with this model have shown an improvement in attached cell viability after transplantation. However, a concern presented was the inability to maintain a flat, wrinkle-free monolayer through the surgical procedure. As such, cell attachment is seen off target and with clumping phenotype. The first human trial with this strategy has been performed (Mandai et al., *N Eng J Med.*, 376:1038-1046 (2017)) and the clinical trial is on-going.

To overcome the maintenance of the monolayer, a general tissue engineering strategy has been to utilize synthetic polymer substrates as a basal support to RPE during the differentiation process and subsequent implantation. Two materials that are currently in clinical trials include parylene (Hu et al., *Ophthalmic Res.*, 48:186-191 (2012); and Diniz et al., *Invest. Ophthalmol. Vis. Sci.*, 54:5087-5096 (2013)) and polyester (Stanzel et al., *Stem Cell Rep.*, 2:64-77 (2014)). These materials can be modified to create micropores and improve cell attachment (Lu et al., *Biomed. Microdevices*, 14:659-667 (2012); McHugh et al., *Invest. Ophthalmol. Vis. Sci.*, 55:1754-1762 (2014); and Lai et al., *PLoS ONE.* 8:e54058 (2013)). These materials also degrade slowly, enabling culture of cells through the long RPE differentiation protocol. Because of this slow degradation, the material can remain between the RPE and choroid after implantation for several months to years, causing concerns of chronic inflammation and fibrosis, low permeability and potentially reduced RPE survival. Additionally, due to the rigidity of the material, there is concern of damage to the underlying choroid, as seen in previous animal studies (Diniz et al., *Invest. Ophthalmol. Vis. Sci.*, 54:5087-5096 (2013)).

This document provides methods and materials for using fibrin supports for RPE transplantation. Fibrin can be a cross-linking fibril network formed spontaneously after the activation of a precursor to its self-polymerizing monomers. Fibrin typically makes up the clot that forms physiologically during wound healing, and has a well characterized cascade of activation, formation, degradation, and clearance (Undas et al., *Arterioscler. Thromb. Vasc. Biol.*, 31:e88-e99 (2011)). For example, fibrin gels can be rapidly degraded through the activation of plasminogen to plasmin, a process activated by enzymes like tissue plasminogen activator (tPA). Fibrin, often referred to as fibrin glue, is used in the clinic as a natural sealant during surgical incisions in soft tissues and is available commercially. The fibrin used herein can be highly adhesive, can have biomechanical rigidity, can be biocompatible, and can be degradable.

To confirm the suitability of fibrin as a substrate for RPE transplantation, the properties of the fibrin hydrogel to form a thin layer, rigid hydrogel with defined parameters for degradation on the scale of hours was varied. Then, the optimized conditions were applied to iPSC-RPE monolayers. The ability to detach the fibrin-RPE (FRPE) implant was investigated. In vitro cell viability and phenotype was assessed after each step, including hydrogel degradation, to insure the potential efficacy of the cells for transplantation. As described herein, fibrin hydrogels can be used as a temporary apically-apposed or basal support substrate for RPE transplantation. For example, RPE transplantation can be performed using an RPE monolayer/fibrin implant provided herein. The fibrin scaffold can be on the apical side or basal side of the RPE monolayer for improved RPE attachment. In some cases, RPE can be grown on the fibrin support to develop a monolayer with basal support. These cultures can be cut to develop individual units for implantation. In other examples, the fibrin scaffold can be on the apical side of the RPE monolayer for improved RPE attachment. In some cases, modular tiling of multiple (e.g., two, three, four, or more) RPE monolayer/fibrin implants can provide large area coverage, and laser tacking can be used to enable precision of delivery location. In some cases, the fibrin scaffold can be degraded under controlled conditions during surgery using, for example via tPA.

In general, one aspect of this document features a retinal implant comprising, or consisting essentially of, (a) a retinal pigment epithelium monolayer having an apical surface and a basal surface, and (b) a fibrin hydrogel layer attached to the apical and/or basal surface of the monolayer. The fibrin hydrogel layer can be from about 20 μm to about 400 μm thick. The implant can comprise plasminogen. The implant can comprise from about 0.1 U of plasminogen per mL to about 40 U of plasminogen per mL. In some cases, the implant can comprise from about 0.001 U of plasminogen per mL to about 40 U of plasminogen per mL. In some cases, the fibrin hydrogel layer can be obtained autologously.

In another aspect, this document features a method for making a retinal or sub-retinal implant. The method comprises, or consists essentially of, (a) obtaining a retinal pigment epithelium monolayer having an apical surface and a basal surface, and (b) depositing a coating of fibrinogen and thrombin onto the apical surface of the monolayer. The coating can be from about 20 μm to about 400 μm thick. The method coating can comprise from about 20 mg of fibrinogen per mL to about 80 mg of fibrinogen per mL. The method coating can comprise from about 2 U of thrombin per mL to about 1500 U of thrombin per mL. The method can comprise depositing plasminogen onto the apical surface of the monolayer. The method can comprise depositing plasminogen within the fibrin hydrogel onto the apical surface of the monolayer. The method coating can comprise from about 0.1 U of plasminogen per mL to about 40 U of plasminogen per mL. In some cases, the implant can comprise from about 0.001 U of plasminogen per mL to about 40 U of plasminogen per mL.

In another aspect, this document features a method for making a retinal or sub-retinal implant. The method comprises, or consists essentially of, culturing retinal epithelial cells on a fibrin basal support substrate in a medium comprising a protease inhibitor or an antifibrinolytic agent (e.g., a small molecule protease inhibitors). The medium can comprise the protease inhibitor, and the protease inhibitor can be aprotinin. The medium can comprise from about 5 U of aprotinin per mL to about 500 U of aprotinin per mL. The medium further can comprise plasminogen. The medium can comprise from about 0.1 U of plasminogen per mL to about 40 U of plasminogen per mL (e.g., 0.1 U of plasminogen per mL to about 30 U of plasminogen per mL). In some cases, the implant can comprise from about 0.001 U of plasminogen per mL to about 40 U of plasminogen per mL. In some examples, plasminogen can be added to the medium just prior to transplantation. The fibrin basal support substrate can comprise endothelial cells. In some cases, the endothelial cells were obtained from a source selected from the group consisting of iPSC-derived endothelial cells, blood outgrowth endothelial cells (BOEC), endothelial colony-forming cells (ECFCs), endothelial progenitor cells (EPCs), and umbilical vein endothelial cells (UVEC). The fibrin basal support substrate can comprise sub-RPE tissue cell populations. The sub-RPE tissue cell populations can comprise melanocytes, pericytes, or fibroblasts. In some cases, the fibrin basal support substrate can be obtained autologously.

In another aspect, this document features a retinal implant comprising (a) a retinal pigment epithelium monolayer having an apical surface and a basal surface, and (b) a fibrin hydrogel layer attached to the basal surface of the monolayer. The fibrin hydrogel layer can be from about 20 μm to about 400 μm thick. The implant can comprise plasminogen. The implant can comprise from about 0.1 U of plasminogen per mL to about 40 U of plasminogen per mL or from about 0.001 U of plasminogen per mL to about 40 U of plasminogen per mL. The fibrin hydrogel layer can comprise a coating. The coating can comprise basement membrane proteins, matrigel, or geltrex. In some cases, the fibrin hydrogel monolayer can be obtained autologously.

In another aspect, this document features a method for making a retinal implant. The method comprises (a) obtaining a fibrin hydrogel layer, (b) coating a surface of the fibrin hydrogel layer with an agent, and (c) forming a retinal pigment epithelium monolayer having an apical surface and a basal surface on the coating, wherein the basal surface is closer to the fibrin hydrogel layer than the apical surface. The fibrin hydrogel layer can be from about 20 μm to about 400 μm thick. The fibrin hydrogel layer can comprise from about 20 mg of fibrinogen per mL to about 80 mg of fibrinogen per mL. The fibrin hydrogel layer can comprise from about 2 U of thrombin per mL to about 1500 U of thrombin per mL. The fibrin hydrogel layer can comprise from about 0.1 U of plasminogen per mL to about 40 U of plasminogen per mL or from about 0.001 U of plasminogen per mL to about 40 U of plasminogen per mL. In some cases, the fibrin hydrogel monolayer can be obtained autologously.

In another aspect, this document features a method for making a retinal implant. The method comprises culturing retinal epithelial cells on a fibrin basal support substrate in a medium comprising a protease inhibitor or an anti-fibrinolytic agent. The medium can comprise the protease inhibitor, and the protease inhibitor can be aprotinin. The medium can comprise from about 5 U of aprotinin per mL to about 500 U of aprotinin per mL. The medium can comprise the anti-fibrinolytic agent, and the antifibrinolytic agent can be transexamic acid or aminocaproic acid. The medium can further comprise plasminogen. The medium can comprise from about 0.1 U of plasminogen per mL to about 40 U of plasminogen per mL or from about 0.001 U of plasminogen per mL to about 40 U of plasminogen per mL. The fibrin basal support substrate can comprise endothelial cells. The endothelial cells can be obtained from a source selected from the group consisting of iPSC-derived endothelial cells, blood outgrowth endothelial cells (BOEC), endothelial colony-forming cells (ECFCs), endothelial progenitor cells (EPCs), and umbilical vein endothelial cells (UVEC). The fibrin basal support substrate can comprise a coating. The coating can comprise basement membrane proteins, matrigel, or geltrex. The coating can be present prior to culturing the retinal epithelial cells on the fibrin basal support substrate. The fibrin basal support substrate can comprise sub-RPE tissue cell populations. The sub-RPE tissue cell populations can comprise melanocytes, pericytes, or fibroblasts. In some cases, the fibrin basal support substrate can be obtained autologously.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 34 is mechanical strength data of fibrin gels formed in the 1.5 mm×5 mm geometry.

FIG. 35 is shows images of the fibrin hydrogel structure.

FIG. 36B also contains graph plotting the kinetics of degradation when varying tPA concentrations. Fibrinogen and plasminogen concentrations were fixed. A non-linear relationship was observed between tPA concentration and degradation time.

FIG. 37 is shows data for the need to include a protease inhibitor such as aprotinin.

FIG. 38 is characterization of iPSC-RPE grown on a fibrin hydrogel support. FIG. 38A shows iPSC-RPE appear as pigmented, cobblestone patterned monolayers when viewed under phase contrast light microscopy. FIG. 38B uses a live/dead assay to show that iPSC-RPE are viable when cultured on fibrin. FIG. 38C shows ELISA quantification of VEGF and PEDF secretion by the iPSC-RPE. FIG. 38D shows western blot analysis for the key RPE markers, Best1, RPE65, and CRALBP, with a reference B-actin.

FIG. 40 is a table showing the RNA profile of iPSC-RPE cultured on fibrin gels using PCR.

DETAILED DESCRIPTION

Figure 1A:
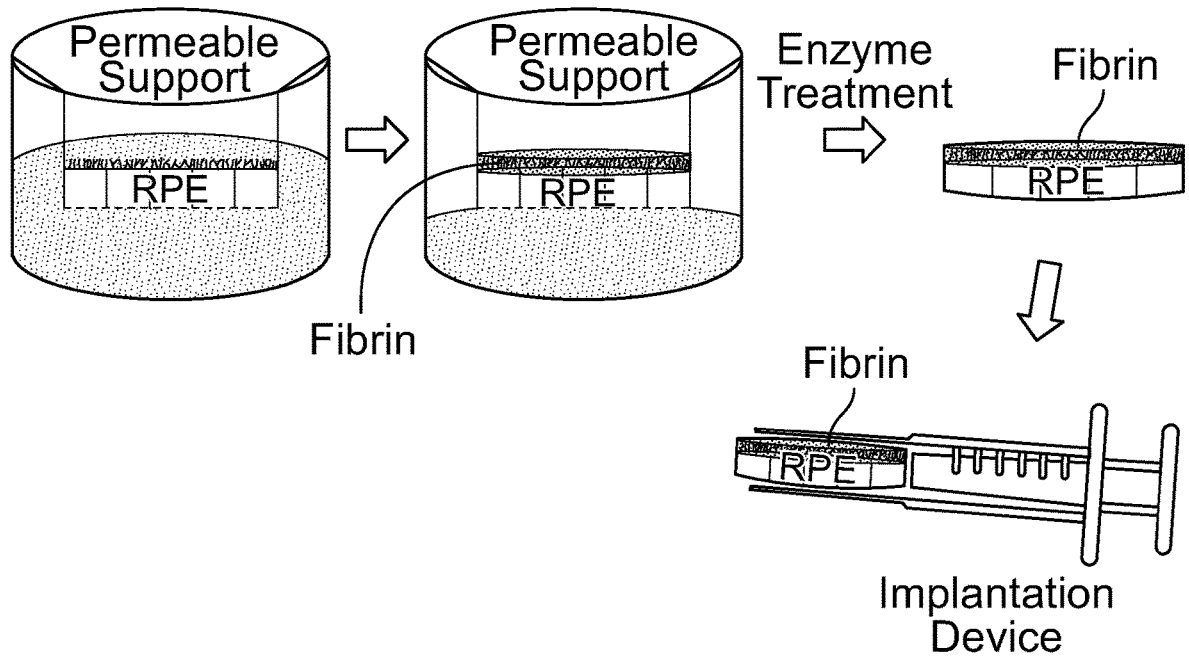
FIG. 1A is a schematic of a method for making an RPE monolayer with apical fibrin and loading it into a surgical implantation device.
Figure 1B:
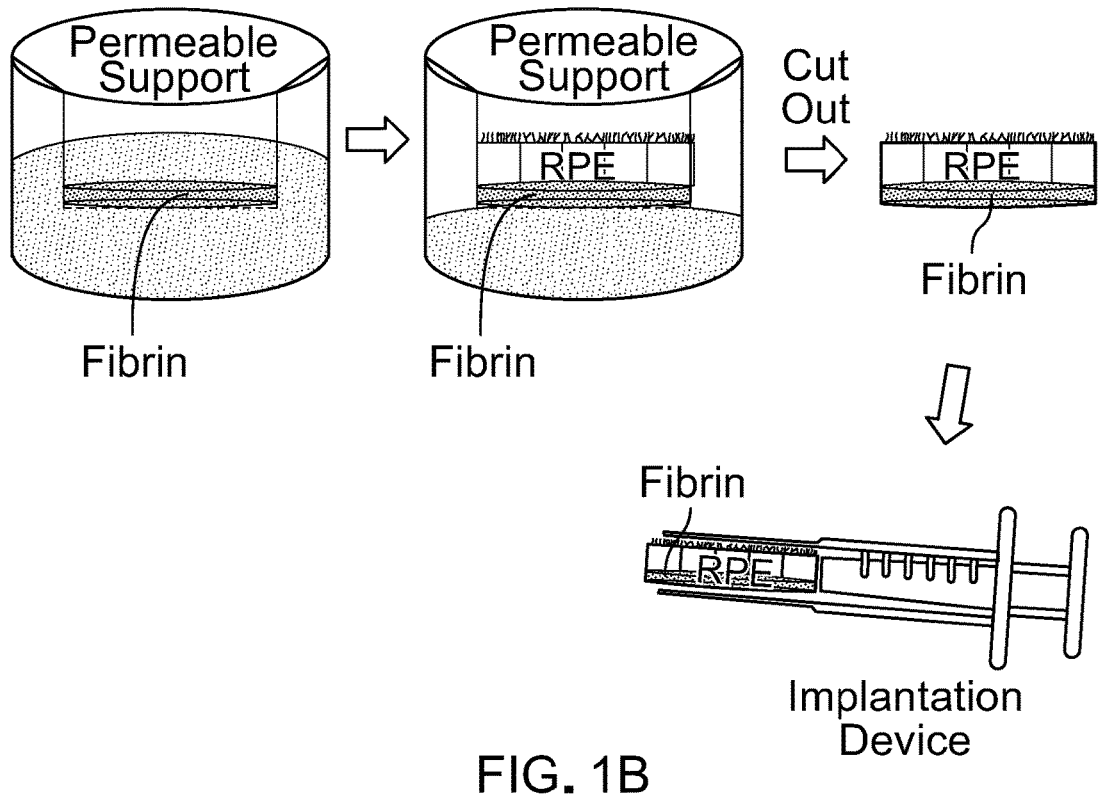
FIG. 1B is a schematic of a method for making an RPE monolayer with basal fibrin and loading it into a surgical implantation device.

This document relates to retinal pigment epithelium transplantation. For example, this document provides methods and materials for using fibrin supports for retinal pigment epithelium transplantation. As described herein, fibrin hydrogels can be used as a temporary substrate for RPE transplantation. The fibrin hydrogel can be a basal support substrate (FIG. 1B) or an apically-apposed substrate (FIG.

1A) for the RPE. In some cases, the RPE can be sandwiched between two fibrin hydrogels; one basal support substrate and one apically-apposed substrate.

The RPE monolayer/fibrin implants provided herein can maintain the RPE as a flat, wrinkle-free monolayer. In some cases, the fibrin configuration can provide mechanical support and protection during the transplantation process and can ensure implantation of correct RPE polarity. In some cases, the RPE monolayer/fibrin implants provided herein can reduce potential chronic inflammation, obstacles to RPE/Bruch's membrane attachment and can maintain diffusion permeability from choroid.

Any appropriate method can be used to produce a fibrin substrate for RPE monolayers. Gelation kinetics can be directly related to thrombin concentration, and fibrin hydrogel mechanical properties can be directly related to initial fibrinogen concentration. In some cases, a higher fibrinogen concentration can result in increased cross links and a stiffer fibrin hydrogel. In general, fibrin hydrogel can be formed as a thin sheet. In some cases, compaction of the fibrin hydrogel can further stiffen the hydrogel.

In some cases, fibrin thin film deposition can be achieved through either spray-coating or sandwich method. In one example, a mixture of fibrinogen and thrombin (and optionally plasminogen) can be sprayed onto the apical side of RPE monolayer and allowed to gel fully to achieve an apical fibrin coating. In one example, a droplet mixture of fibrinogen and thrombin (and optionally plasminogen) can be placed onto the apical side of RPE monolayer, and the droplet can be compressed or spread and allowed to gel fully to achieve an apical fibrin coating.

In some cases, a spray coating of a thin layer of fibrin can be used to form a fibrin hydrogel. Sprayer systems such as those used for general and laproscopic surgery can be repurposed to produce fibrin hydrogels as described herein. See, also, Chaurasia et al. (*Transl. Vis. Sci. Technol.,* 1:2 (2012)). The thickness of the fibrin hydrogels provided herein can be from about 10 μm to about 400 μm (e.g., from about 20 μm to about 400 μm, from about 50 μm to about 400 μm, from about 10 μm to about 200 μm, or from about 50 μm to about 200 μm).

A fibrin hydrogel provided herein can be easily maneuvered with surgical tools for precise orientation and location. In some cases, a fibrin hydrogel provided herein can be pliable, while maintaining its original shape and surface properties. In some cases, adherent cells do not detach from the surface of a fibrin hydrogel provided herein.

In some cases, a fibrin hydrogel provided herein can be made by spraying a solution containing from about 0.01 mg/mL to about 80 mg/mL of fibrinogen (e.g., from about 20 mg/mL to about 80 mg/mL of fibrinogen). In some cases, greater than 30 mg/mL of fibrinogen (e.g., from about 30 mg/mL to about 80 mg/mL of fibrinogen) can be used to produce a fibrin hydrogel that can be manipulated with tweezers. In some cases, a fibrin hydrogel provided herein can be made by spraying a solution containing from about 40 mg/mL to about 60 mg/mL of fibrinogen.

In some cases, a fibrin hydrogel provided herein can be made using fibrinogen as described herein and from about 2 U/mL to about 1000 U/mL of thrombin (e.g., from about 10 U/mL to about 200 U/mL of thrombin). In some cases, greater than 5 U/mL of thrombin (e.g., from about 10 U/mL to about 100/mL of thrombin) can be used to produce a fibrin hydrogel that can be manipulated with tweezers. In some cases, a fibrin hydrogel provided herein can be made by spraying a solution containing from about 40 mg/mL to about 60 mg/mL of fibrinogen and from about 10 U/mL to about 100 U/mL of thrombin.

In some cases, a fibrin hydrogel provided herein can be preloaded with inactive plasminogen. For example, inactive plasminogen can be pre-loaded into a fibrin hydrogel by binding it to the intact fibrin hydrogel. In some cases, inclusion of plasminogen can be achieved through the incubation and diffusion of plasminogen into the fibrin gel prior to delivery of a fibrin supported RPE for implantation into an eye. In some cases, an RPE/fibrin hydrogel implant provided herein that contains plasminogen can be exposed to tPA after the implant is positioned within an eye. In these cases, the tPA exposure activates the plasminogen into plasmin, which in turn degrades the fibrin hydrogel. The plasmin concentration is directly related to fibrin degradation kinetics as described herein. In some cases, a fibrin hydrogel provided herein can be made to contain from about 0.001 U/mL to about 40 U/mL of plasminogen (e.g., from about 0.5 U/mL to about 4 U/mL of plasminogen, from about 0.1 U/mL to about 30 U/mL of plasminogen, or from about 0.1 U/mL to about 40 U/mL of plasminogen). In some cases, an RPE/fibrin hydrogel implant provided herein can be delivered as a suspension in solution with plasminogen and/or tissue plasminogen activator for implantation into an eye.

In some cases, an RPE/fibrin hydrogel implant provided herein can be produced over a collagen gel. In such cases, the RPE/fibrin hydrogel implant can be harvested using collagenase (e.g., from about 200 U/mL to about 1500 U/mL of collagenase). Collagenase does not interfere with cell-cell interaction and allows the RPE monolayer to detach from the collagen gel. The RPE monolayer also remains adhered to the fibrin hydrogel following collagenase treatment. In some cases, dispase (e.g., from about 0.5 U/mL to about 10 U/mL of dispase) can be use in addition to collagenase or in place of collagenase.

In some cases, an RPE/fibrin hydrogel implant provided herein can be produced in the presence of an antifibrinolytic agent, such as the protease inhibitor Aprotinin (e.g., from about 5 U/mL to about 500 U/mL of Aprotinin), to preserve the fibrin scaffold and prevent degradation of fibrin support throughout the culture period. Other anti-fibrinolytic agents that can be used as described herein include, without limitation, protease inhibitors (e.g., macroglobulin, thrombin, thrombin-activatable fibrinolysis inhibitor, and carboxypeptidases), members of the serine protease inhibitors (serpin) family (e.g., antitrypsin, alpha 2-antiplasmin, and plasminogen activator inhibitor 1 and 2), metalloprotease inhibitors (e.g., Tissue inhibitors of metalloproteinases 1-4, Batimastat, Cipemastat, and Ilorastat) and small molecules (e.g., aminocaproic acid (Amicar), tranexamic acid (Lysteda), heparin, alpha-N-acetyl-L-lysine methyl ester (NALME), Vitamin K, and p-aminomethyl-benzoic acid).

As described herein, the fibrin hydrogel of an RPE/fibrin hydrogel implant provided herein can be a short-term (e.g., less than 72 hours, or less than 1 week), mechanical support for delivering the RPE monolayer. For example, the fibrin hydrogel can be attached to the apical (top) side of RPE for delivery into subretinal space of eye, can be biocompatible, and can be rapidly degraded in a controllable manner using tPA as described herein.

Figure 2A:
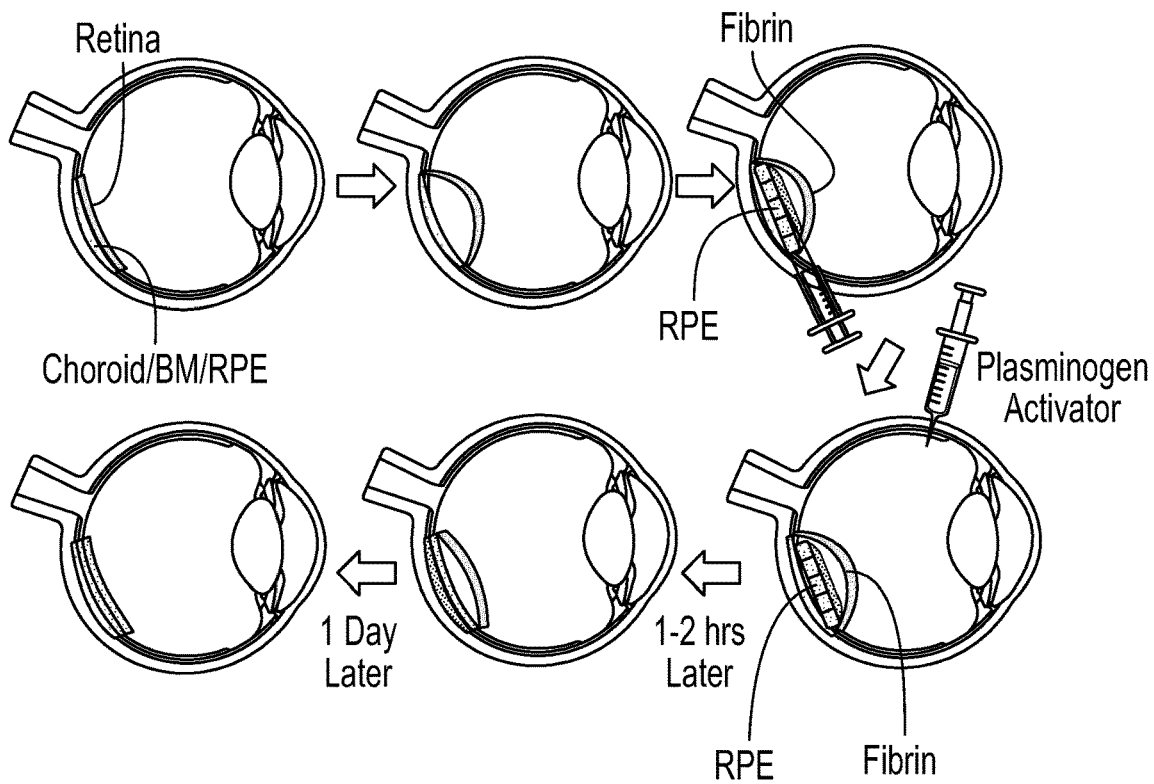
FIG. 2A is a schematic of a method for implanting an RPE monolayer with apical fibrin into an eye to treat macular degeneration.
Figure 2B:
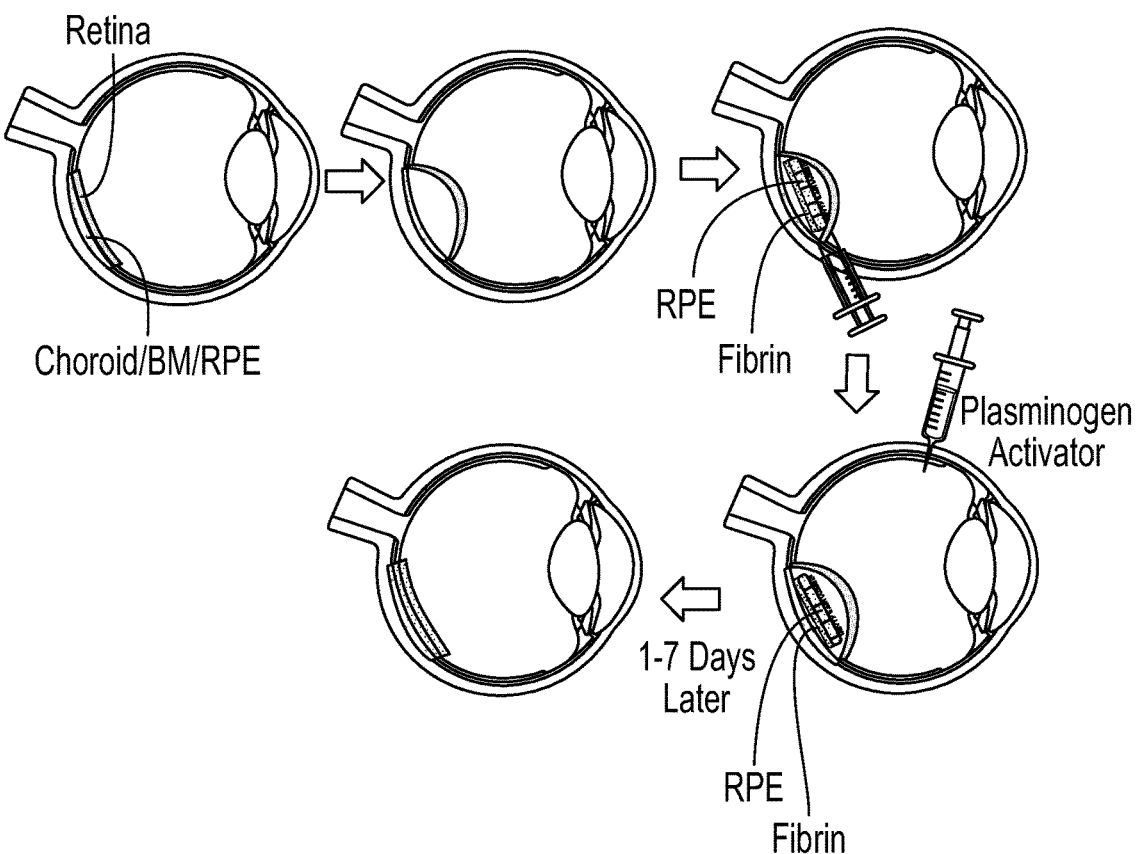
FIG. 2B is a schematic of a method for implanting an RPE monolayer with basal fibrin into an eye to treat macular degeneration.
Figure 3:
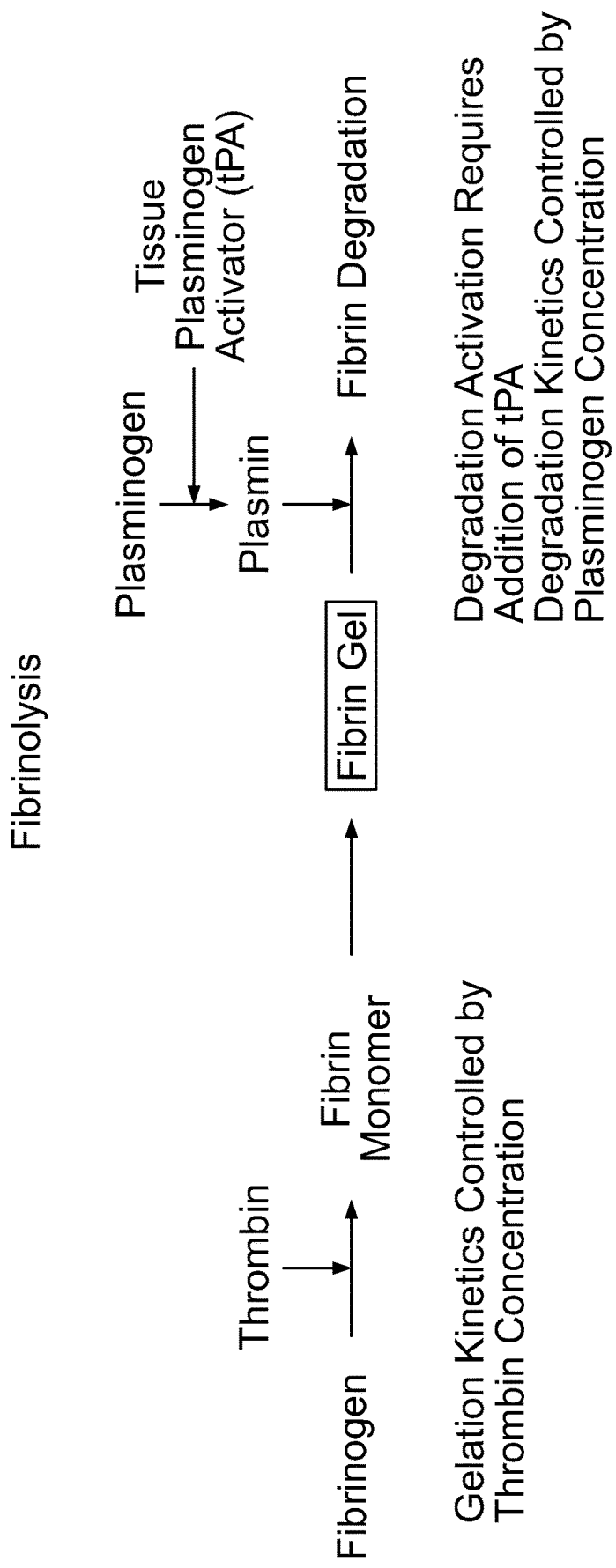
FIG. 3 is a schematic of a fibrinolysis process.

In some cases, an RPE/fibrin hydrogel implant provided herein can be implanted into an eye to provide an effective RPE (FIGS. 2A and 2B).

Figure 20:
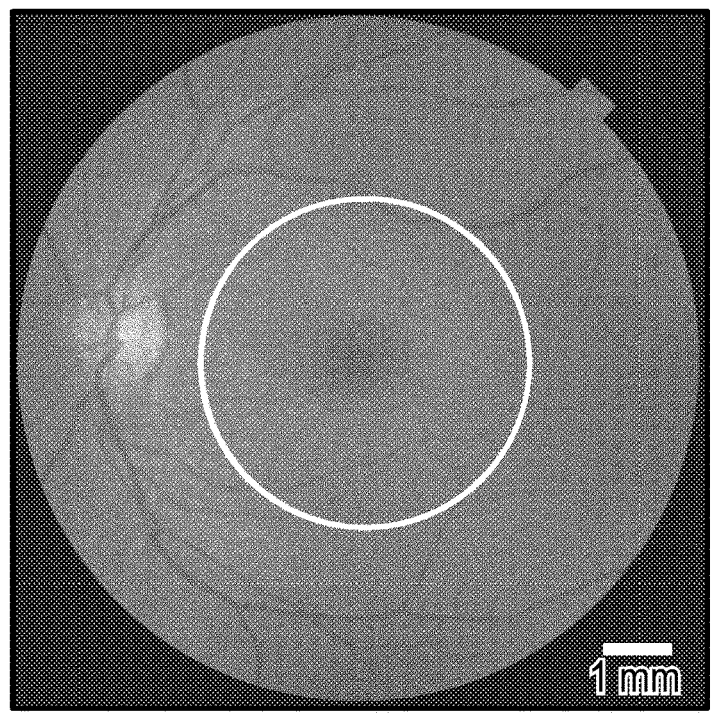
FIG. 20 is a photograph showing that the diseased retina affects a large surface area. The macula (circled area) is 5 mm in diameter (25 mm$^2$). The retina is 1200 mm$^2$. The methods and materials described herein can be used to address the entire macula or other regions of the retina.
Figure 21:
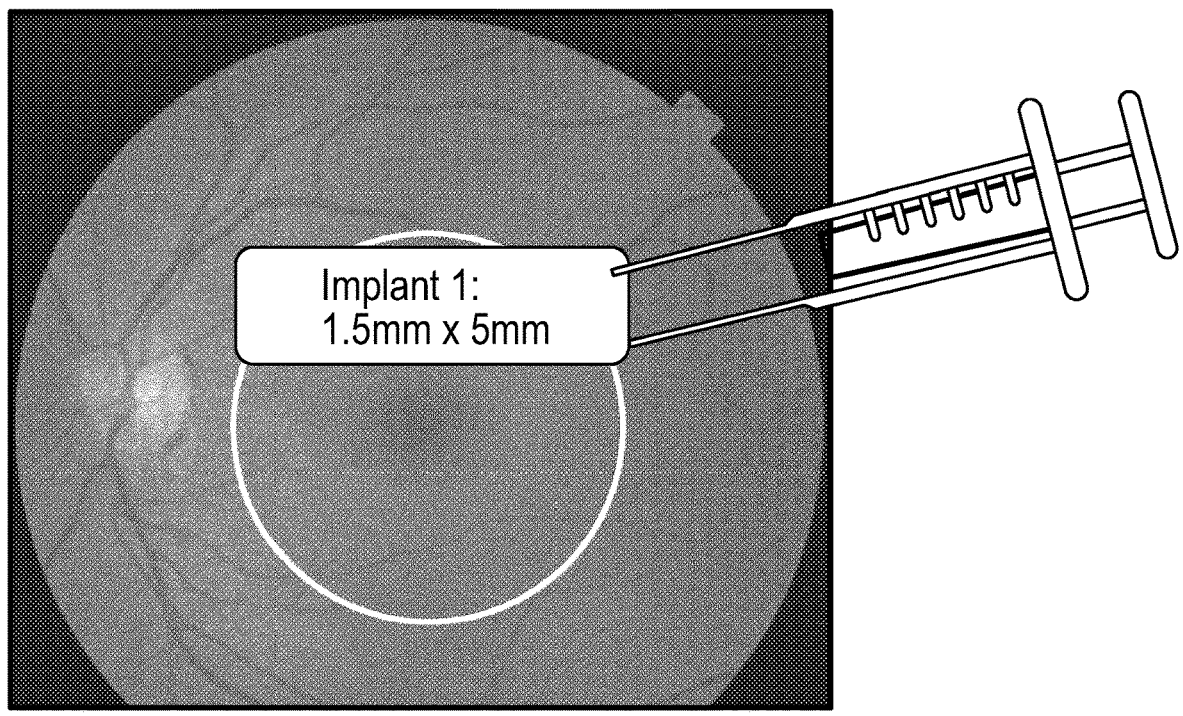
FIG. 21 is a photograph showing the use of an implantation device to deliver an RPE monolayer/fibrin implant onto the region of interest within an eye.
Figure 22:
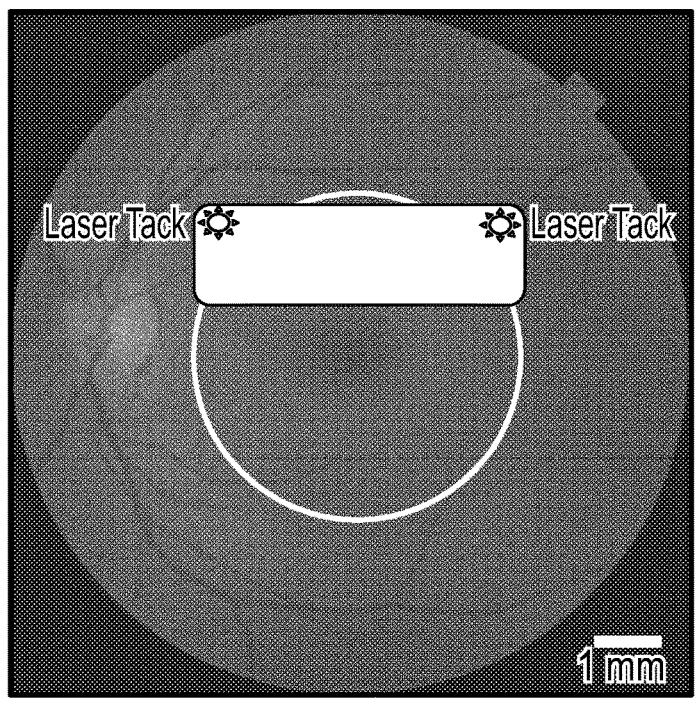
FIG. 22 is a photograph showing the result of using a laser tool to tack the implant down, preventing it from slipping.
Figure 23:
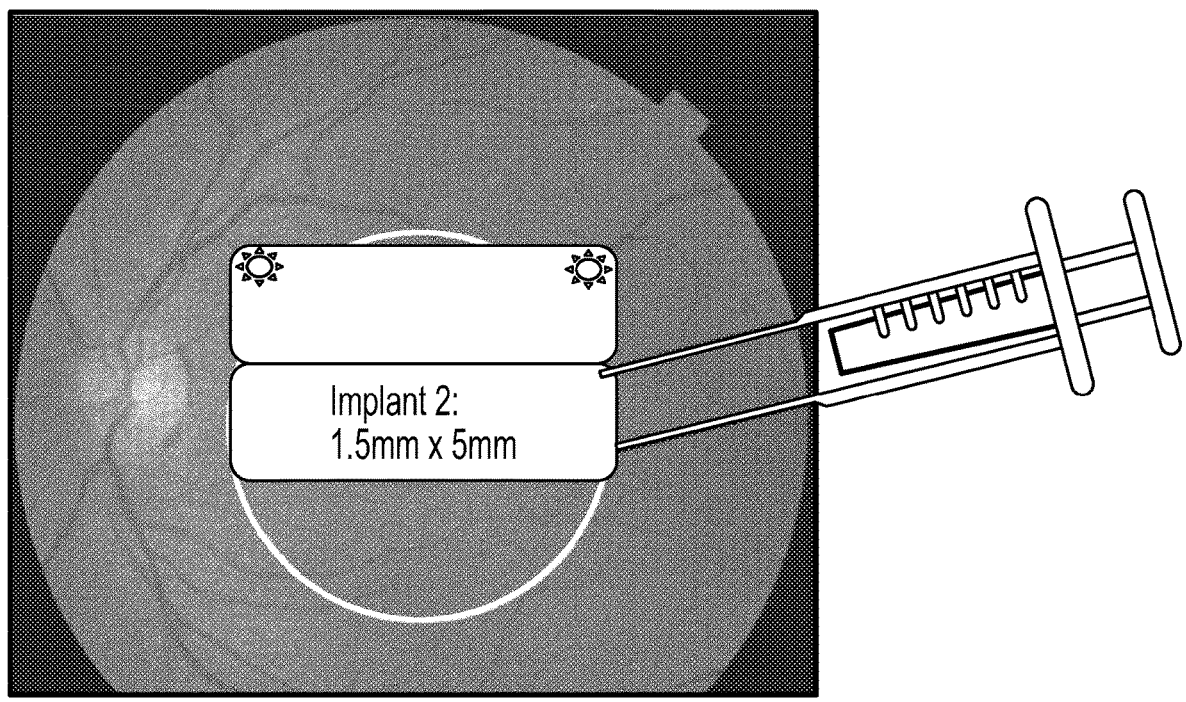
FIG. 23 is a photograph showing the use of an implantation device to deliver a second RPE monolayer/fibrin implant onto the region of interest within an eye. The second implant is placed adjacent to the first, preferably through the original incision.
Figure 24:
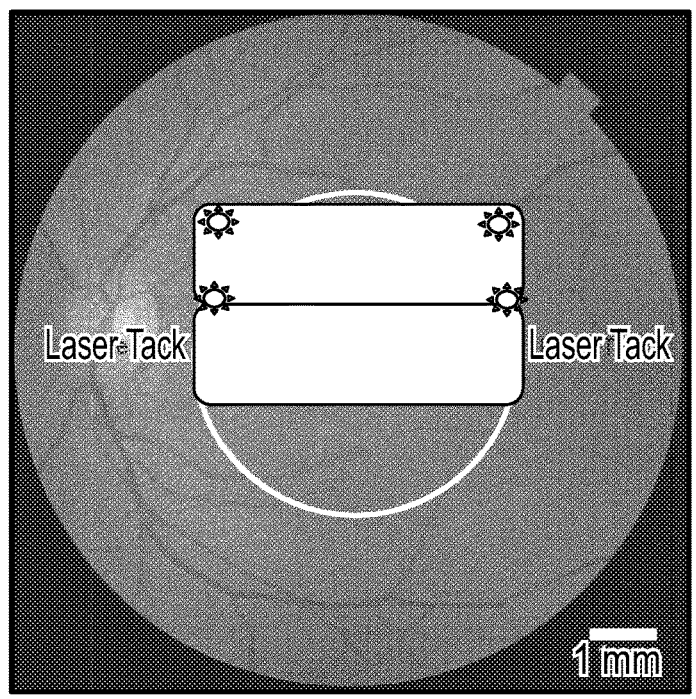
FIG. 24 is a photograph showing the result of using a laser tool to tack the second implant down, preventing it from slipping.
Figure 25:
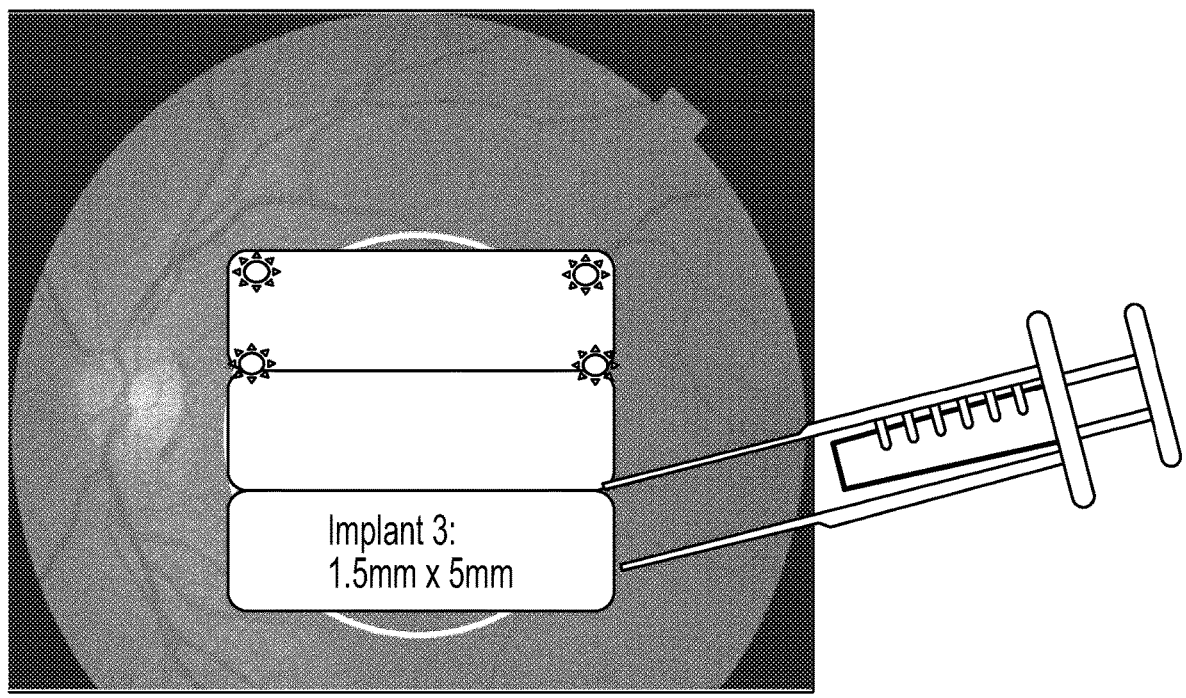
FIG. 25 is a photograph showing the use of an implantation device to deliver a third RPE monolayer/fibrin implant onto the region of interest within an eye. The third implant is placed adjacent to the second, preferably through the original incision.
Figure 26:
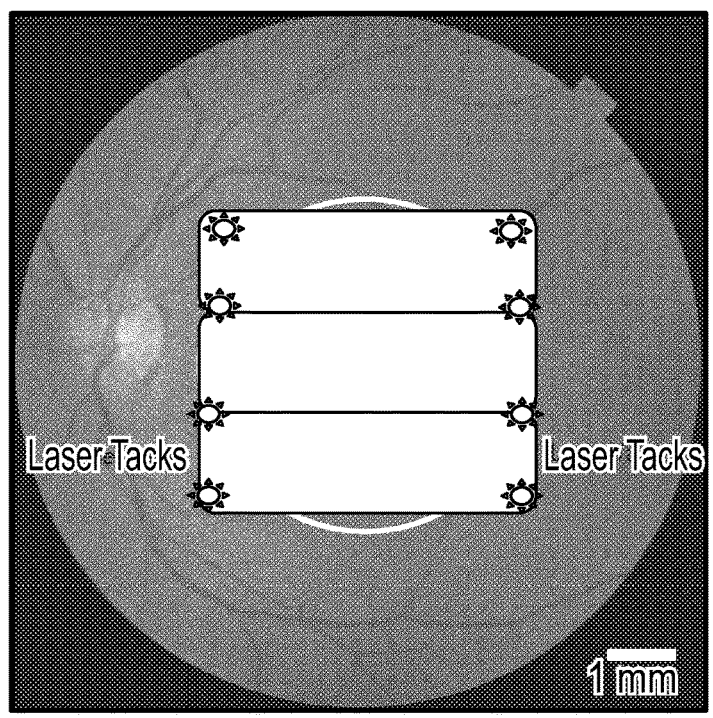
FIG. 26 is a photograph showing the result of using a laser tool to tack the third implant down, preventing it from slipping.
Figure 28:
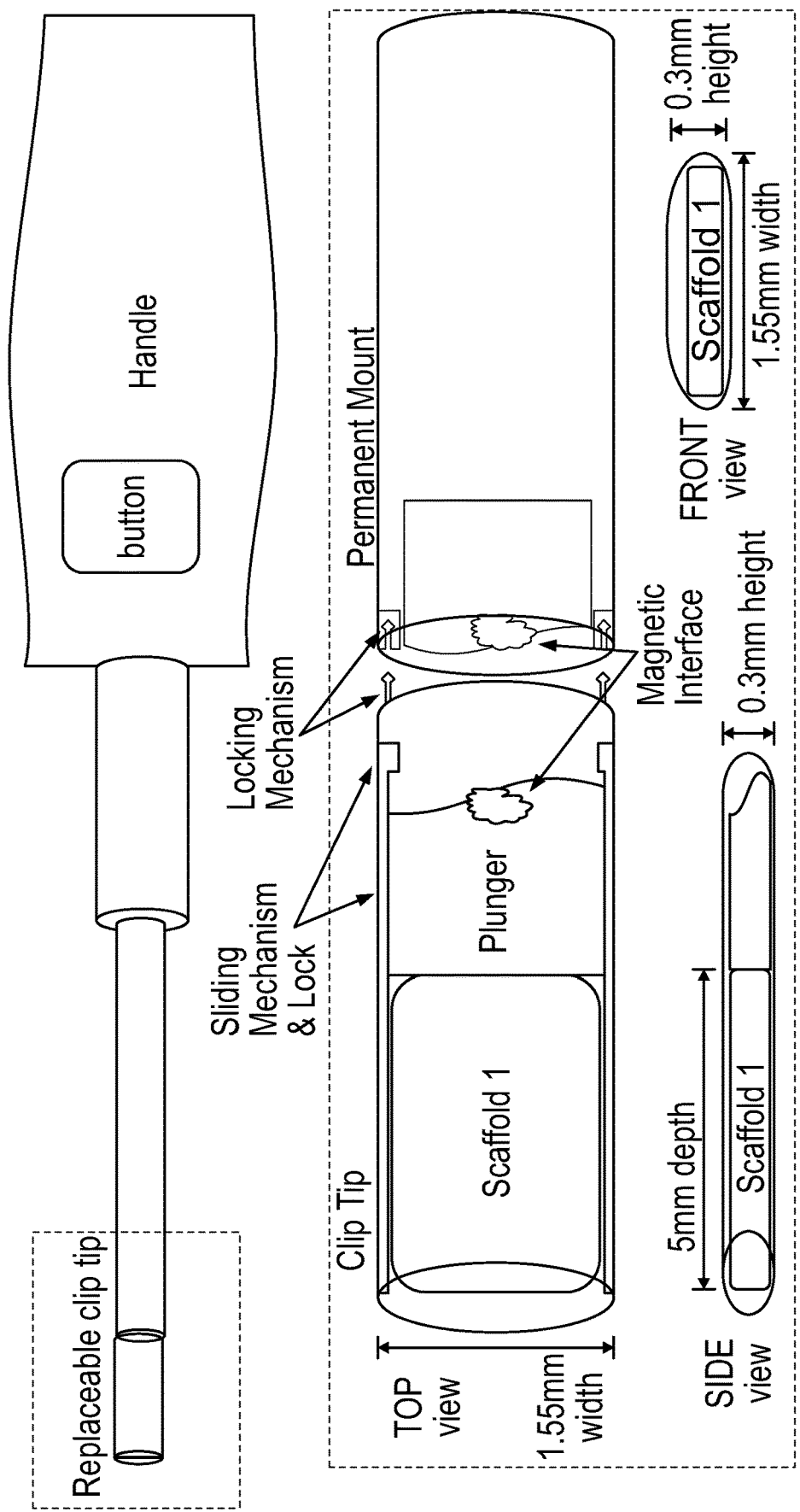
FIG. 28 is a schematic of one example of an implantation device for implanting RPE monolayer/fibrin implants into an eye.
Figure 31:
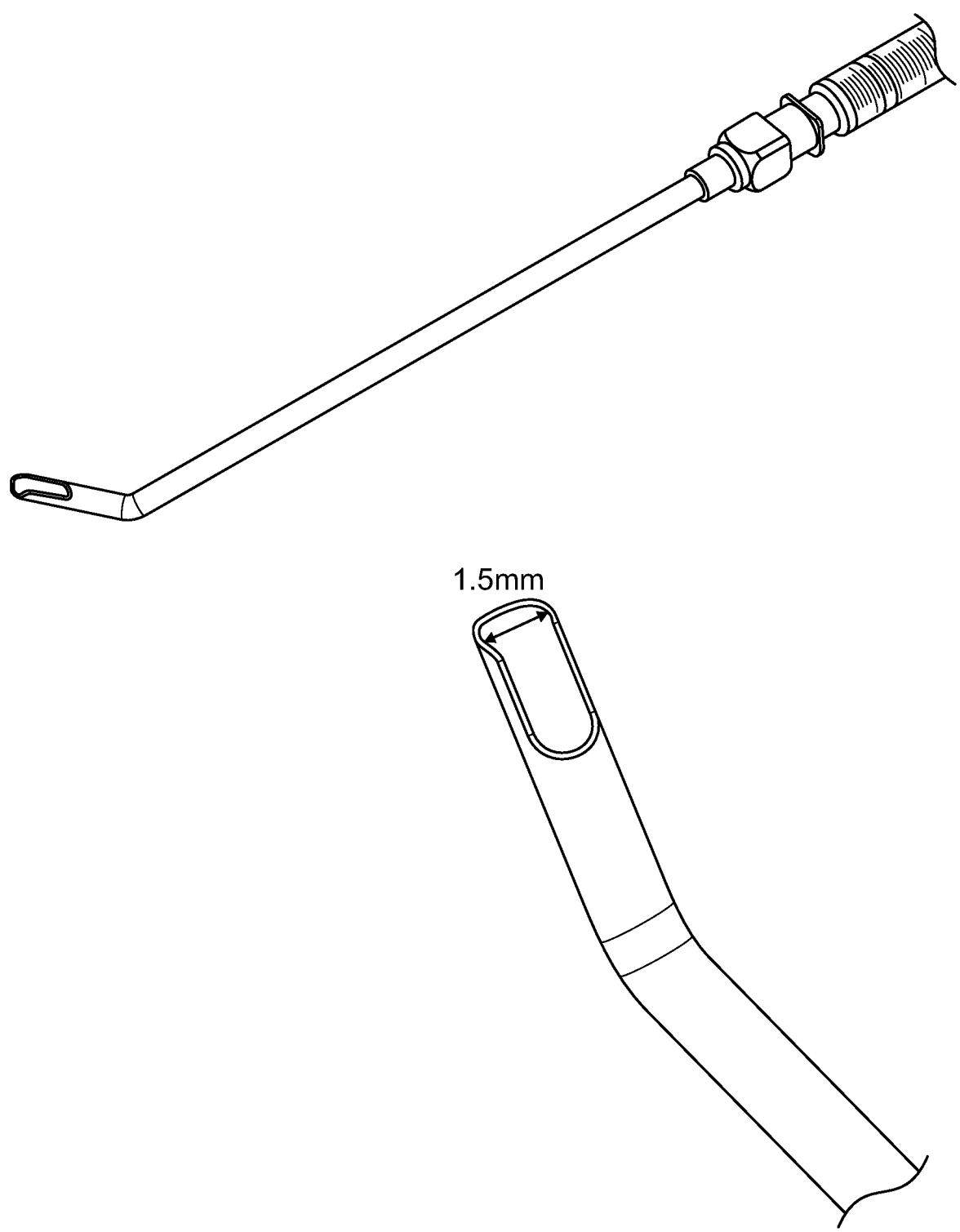
FIG. 31 contains photographs of another prototype of an implantation device for implanting RPE monolayer/fibrin implants into an eye.
Figure 32:
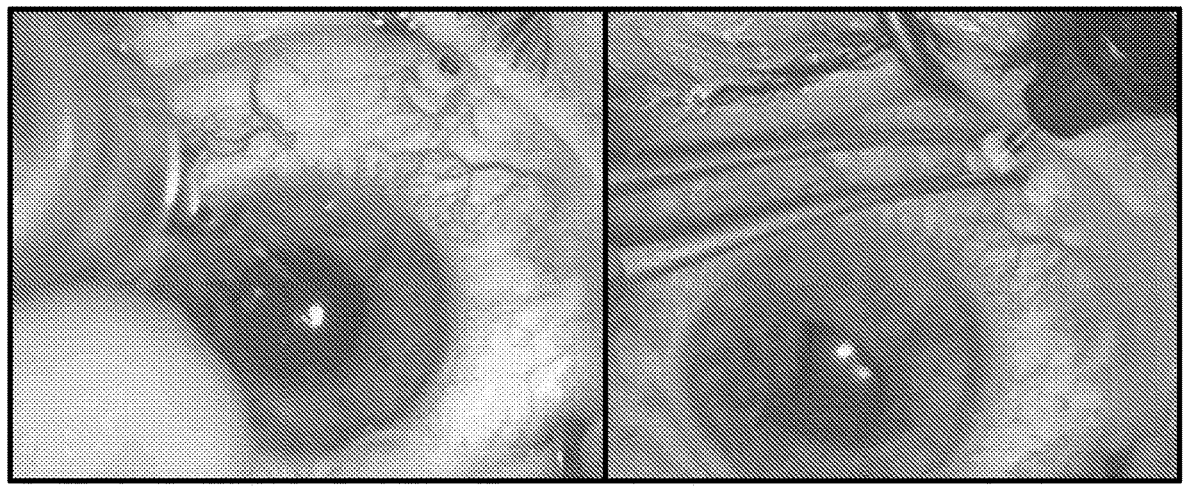
FIG. 32 contains photographs of a cannula port that provides multiple entries into the eye and that maintains eye pressure to prevent eye collapse.
Figure 33:
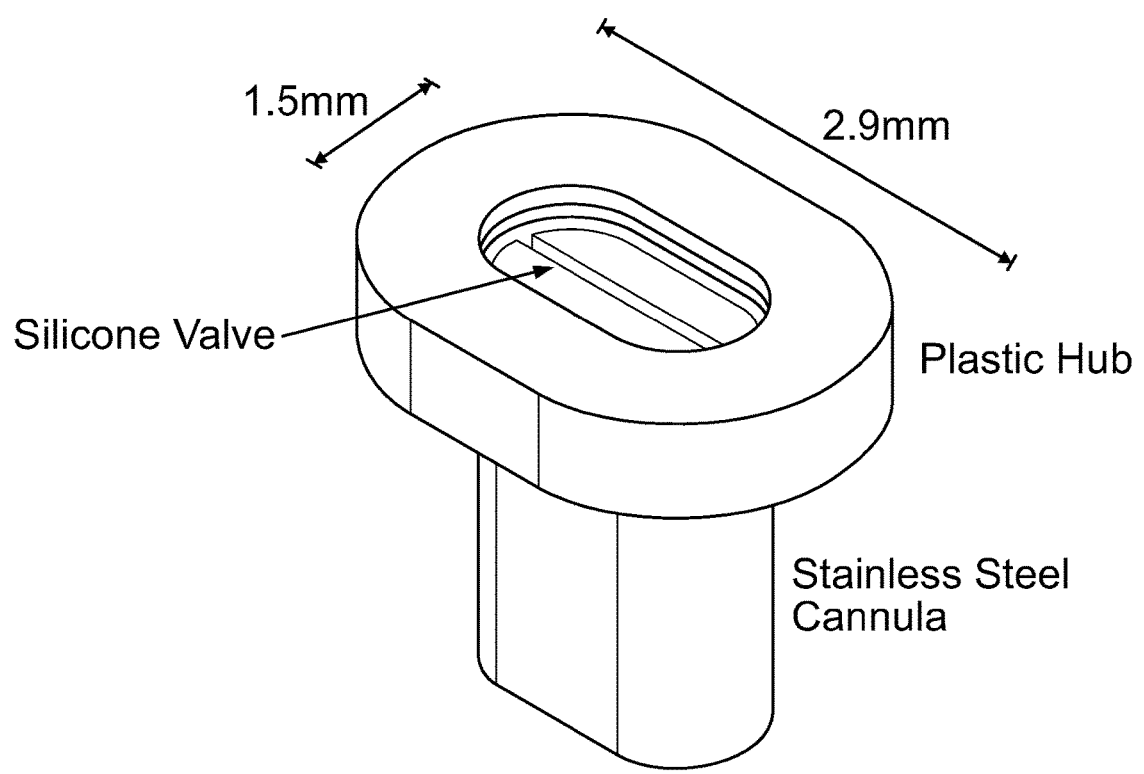
FIG. 33 is a schematic of a cannula port that provides multiple entries into the eye and that maintains eye pressure to prevent eye collapse. The length can range from about 0.1 mm to about 4 mm; and the width can range from about 0.1 mm to about 3 mm.

The document also provides methods for using an RPE/fibrin hydrogel implant provided herein to treat eye conditions such as high myopia, angioid streaks, and macular degeneration. Some of the diseases that classify as macular degeneration and that can be treated as described herein include, but are not limited to, age-related macular degeneration (AMD), central geographic atrophy, bestrophinopathies, Leber's congenital amaurosis, choroideremia, Gyrate atrophy, Sorsby's macular dystrophy, mitochondrial-inherited diabetes and deafness (MIDD), chloroquine-associated retinopathy, malattia leventinese, North Carolina dystrophy, hyperornithinemia, central serous chorioretinopathy, adult-onset foveomacular dystrophy and Stargardt's disease. For example, a mammal (e.g., a human) can be prepared for eye surgery, and a sub-retinal detachment is created to expose a damaged RPE region (FIG. 20). At this point, an implantation device such as one shown in FIG. 28, 29, or 31 can be used to deliver an RPE/fibrin hydrogel implant onto the region of interest (FIG. 21). In some cases, a cannula (see, e.g., FIGS. 32 and 33) can be used to gain access to the eye. In some cases, an air-phase bubble may be used to push the RPE/fibrin hydrogel implant into place. A laser tool (e.g., a laser tool used for diabetic retinopathy) can be used to tack the implant down via laser photocoagulation, preventing it from slipping (FIG. 22). At this point, an implantation device can be used to deliver a second RPE monolayer/fibrin implant onto the region of interest within an eye (FIG. 23). The second implant can be placed adjacent to the first, preferably through the original incision or cannula. A laser tool can be used to tack the second implant down, preventing it from slipping (FIG. 24). An implantation device can be used to deliver a third RPE monolayer/fibrin implant onto the region of interest within an eye (FIG. 25). The third implant can be placed adjacent to the second, preferably through the original incision or cannula. A laser tool can be used to tack the third implant down, preventing it from slipping (FIG. 26). While this section describes implanting three RPE monolayer/fibrin implant, any appropriate number can be used to cover the area to be treated. For example, one, two, three, four, five, six, or more RPE monolayer/fibrin implants can be implanted within a single eye being treated. In general, this modular tiling approach can allow a clinician to personalize the implants to the patient's need, is scalable to large areas, is applicable to any region of the retina, and reduces the number of incisions required.

Figure 27:
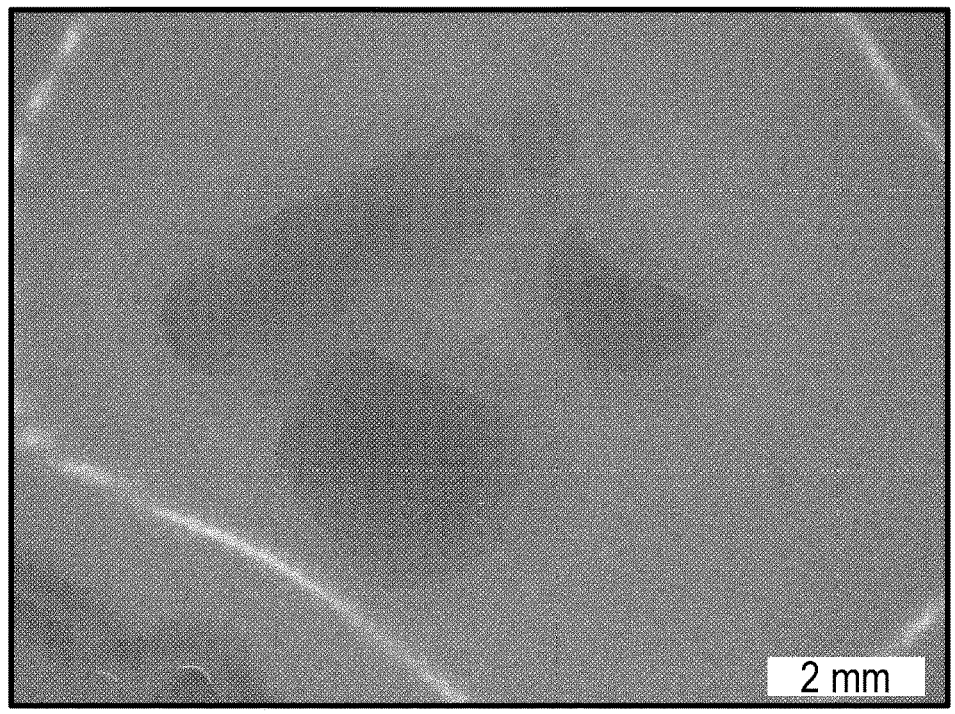
FIG. 27 is a photograph of fibrin scaffolds cut to different size and shape specifications.

In some cases, a mechanical punch can be used to design an RPE monolayer/fibrin implant having a particular shape or size (see, e.g., FIG. 27). Other methods to shape the fibrin implant can include gel casting with custom molds, laser microdissection microscopy, and 3D printing.

An implantation device for implanting an RPE monolayer/fibrin implant provided herein into an eye can be a plunger style device with a mechanical control of ejection. In some cases, an implantation device can have designed to deliver various sized RPE monolayer/fibrin implants and to have the ability to insert multiple implants rapidly using clip-style tips. In some cases, an implantation device provided herein can have a liquid reservoir to maintain hydration of cells and hydrogel. In some cases, an implantation device provided herein be designed for one hand manipulation and use.

In cases involving use of a fibrin basal support, a pre-vascularization strategy can be combined with RPE culture to form choroid tissue. Fibrin can be vascularized by various methods, including through the use of a microfluidic device (Moya et al., *Methods Mol. Biol.*, 1202:21-7 (2014)), 3D printing (Pinnock et al., *Methods*, 99:20-7 (2016)), and spontaneous vascularization of encapsulated endothelial cells within a matrix (Mishra et al., *Biomaterials*, 77:255-66 (2016)). These strategies can be combined with an RPE monolayer culture on top of the pre-vascularized fibrin to form RPE-choroid complex. RPE-choroid can be a therapeutic for macular degenerative diseases in which both the choroid and RPE are dysfunctional, including dry AMD. Endothelial cells (EC) can be obtained from various sources, such as iPSC-derived endothelial cells, blood outgrowth endothelial cells (BOEC), endothelial colony-forming cells (ECFCs), endothelial progenitor cells (EPCs), and umbilical vein endothelial cells (UVEC).

In cases involving use of fibrin basal support, a multi cell population tissue can be combined with RPE culture to form transplant tissue. The fibrin support can be loaded with other cell types found in the sub RPE tissue, including melanocytes, choroidal pericytes, and fibroblasts.

Figure 46:
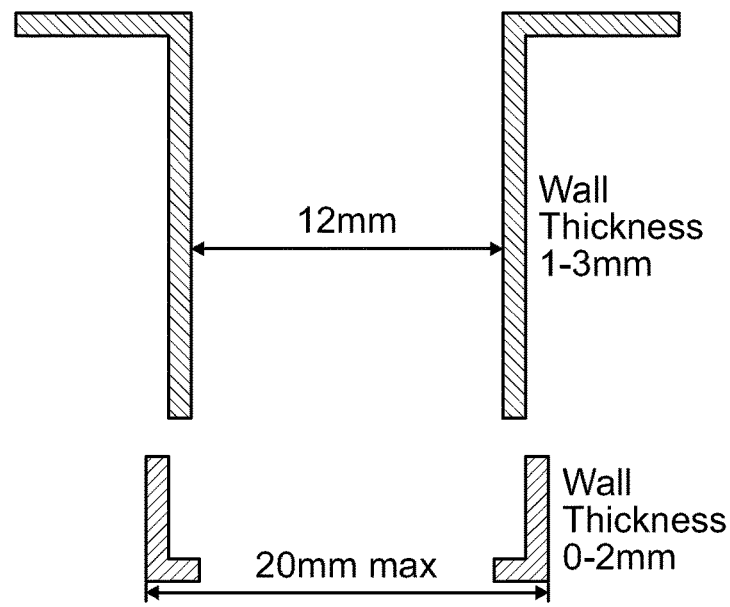
FIG. 46 is a side view of a fibrin hydrogel support device according to one embodiment.
Figure 47:
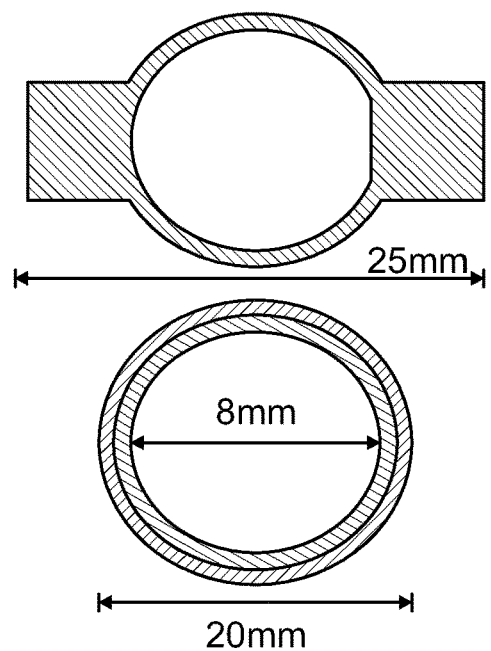
FIG. 47 is a top view of a fibrin hydrogel support device according to one embodiment.
Figure 48:
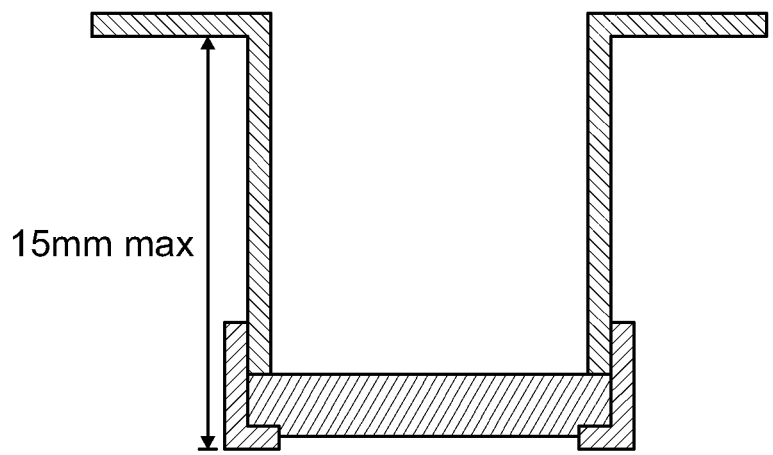
FIG. 48 is a side view of a fibrin hydrogel support device together with a fibrin hydrogel according to one embodiment.

This document also provides a fibrin hydrogel support device that can be used to grow the cells on a fibrin hydrogel that is suspended in cell culture medium. In some cases, this allows a RPE/fibrin hydrogel implant provided herein to be formed in a manner that avoids the need to detach the scaffold from a solid substrate and that allows access of culture media to the basal surface of the cells as they grow and differentiate. In one embodiment, the device can include two separate pieces that can be easily attached to each other to hold the scaffold material in suspension (FIGS. 46-48). A top piece can be a cylindrical inner tube that can be inserted into a bottom, base piece to press and secure a fibrin hydrogel layer sandwiched in between (FIG. 48). The bottom, base piece can include a side wall and an annular bottom with a central opening. The top cylindrical inner tube can be retained and supported by the bottom, base piece. The two components can be made of any appropriate material including, without limitation, Teflon, silicone, or other plastics via, for example, injection molding. In some cases, polystyrene can be used. The dimension of each component can be as shown in FIGS. 46-48. In some cases, the top cylindrical inner tube can engage the bottom, base piece via threads, a snap-fit, or clipping mechanism.

In some cases, a fibrin hydrogel provided herein can be coated prior to apply cells. For example, a fibrin hydrogel provided herein can be coated with basement membrane matrix and/or basement membrane protein (e.g., matrigel or other agent) prior to apply cells. Examples of other agents that can be used to coat fibrin hydrogel provided herein include, without limitation, geltrex, laminin 511, laminin 521, victronectin, collagen, gelatin, and combinations thereof. In some cases, matrigel and geltrex can be used interchangeably as they are both basement membrane matrix derived from mouse sarcoma cells.

The invention will be further described in the following examples, which do not limit the scope of the invention described in the claims.

EXAMPLES

Example 1—Use of Fibrin Hydrogels for IPSC-RPE Transplantation

Chemicals

Fibrinogen was obtained from three sources: as Evicel from Ethicon (60 mg/mL), as Tisseel from Baxter (95 mg/mL), and as research grade material from Sigma-Aldrich (57 mg/mL). Thrombin also was obtained from three sources: part of Evicel from Ethicon, part of Tisseel from Baxter, and research grade material from Sigma-Aldrich. Plasminogen was obtained as research grade material from Sigma-Aldrich. Recombinant tissue plasminogen activator (tPA) was obtained as research grade material from Sigma-Aldrich.

Cells

IPSC-RPE cells were produced as described elsewhere with modification (Johnson et al., *Investig. Ophthalmol. Vis. Sci.*, 56:4619 (2015)). A membrane support was utilized with apical and basal media, including either transwell or HA membrane. The membrane surface was coated with a collagen gel, per manufacturer's protocol, and, either subsequently or alternatively, coated with a geltrex or matrigel solution, up to 0.1 mg/mL for 2 hours at 37° C. Cells were then plated and allowed to form a monolayer for up to one month. For this study, IPSC-RPE was used from healthy control patients. Cells were used after diff stage 5. The trans epithelial resistance was measured above 100 ohms. Pigmentation was noted prior to use.

Formation of Thin Layer Fibrin Gels

Fibrin gels were formed by varying the fibrinogen concentration and thrombin concentration. Thin layer gels were formed initially by a plate sandwich method, in which a mixture of fibrinogen and thrombin solutions was sandwiched between two layers of parafilm within a plastic mold with a 200 μm gap thickness. The solution was allowed to gel up to 1 hour in a humid 37° C. The parafilm was removed, and the gels were hydrated and washed in PBS prior to use. Gels formed by this method had an average thickness of 196±90 μm.

Figures 4A, 4B:
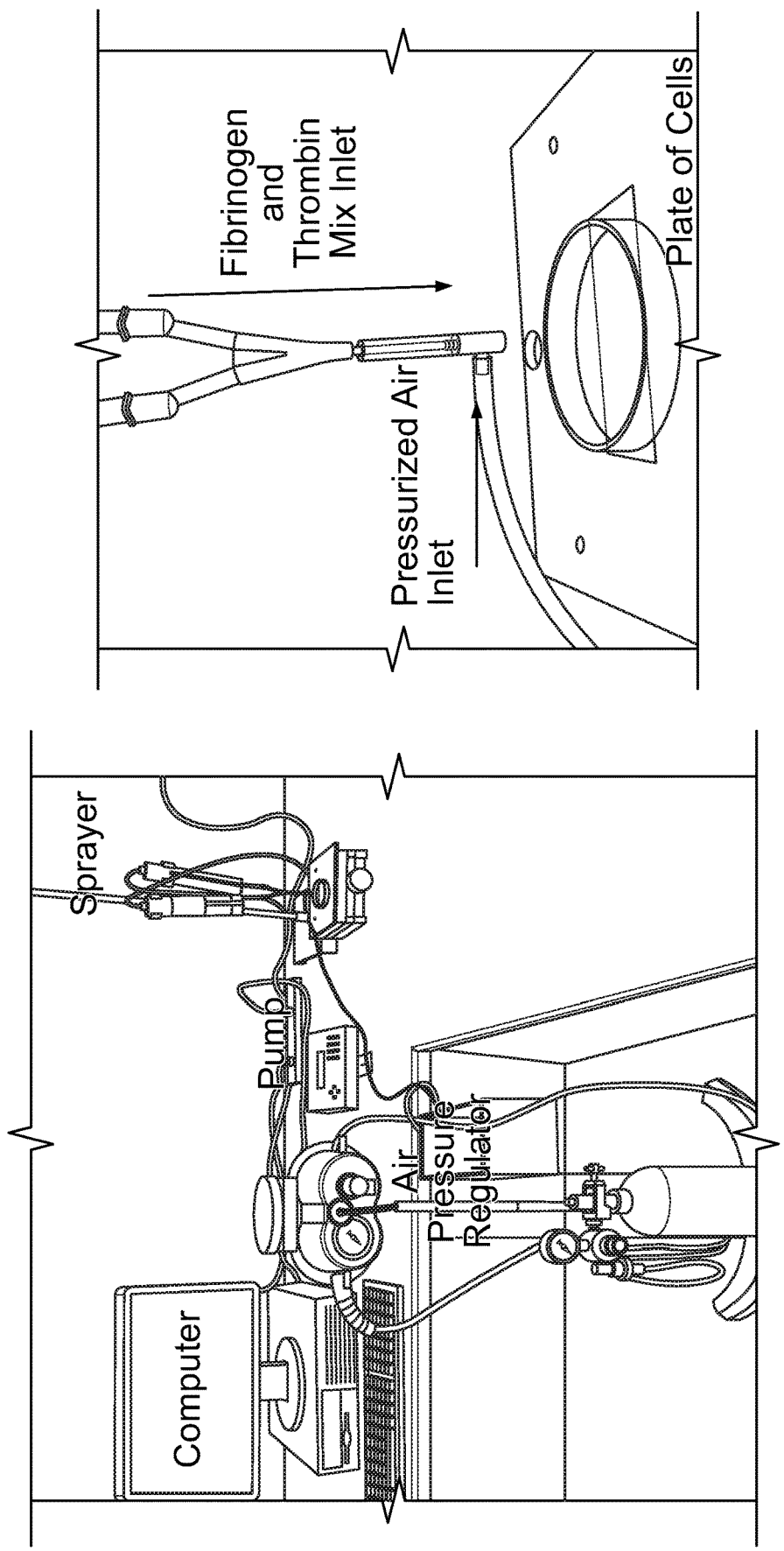
FIG. 4A is a photograph of a sprayer system for forming thin layer fibrin gels.
FIG. 4B is an enlarged photograph of the nozzle of the sprayer system.

Alternatively, a sprayer system was used to form thin layer fibrin gels. Dual microinjector systems (WPI) were connected to a pump controller, which was connected to a computer. Two 1-mL syringes, each with fibrinogen and thrombin solutions, were mounted to the microinjector apparatus, and a two-to-one mixer connector was attached to the syringes. The mixer was then connected to an atomizing nozzle (The Lee Co). A $CO_2$ gas regulator also was attached to the nozzle, to provide the air pressure for atomization. FIGS. 4A and 4B show the set up.

To achieve thin fibrin gel formation, the air pressure and amount of liquid dispensed was varied (0.3-1.5 bar). A custom MATLAB script was utilized to vary sprayer times and rates. The air pressure was varied on the regulator and controlled by a foot pedal. After spraying, the solution was allowed to gel up to 1 hour in a humid 37° C. The gels were hydrated and washed in PBS prior to use.

Gel Thickness Measurement

After gel formation using the sprayer system, the gels were stained with 0.01 mg/mL FITC isothioanate solution for 1 hour and shaken. The unlabeled FITC was removed through subsequent washes with PBS. Confocal z-series images were taken through the gel, and the measure of FITC stained slices was measured to obtain thickness.

Mechanics

Gel biomechanics were obtained using compression testing as described elsewhere (Uehara et al., *J. Bone Joint Surg. Am.*, 97:1792-1798 (2015)). Gels made with various fibrinogen concentrations and thicknesses were measured. Briefly, the gel was mounted to a custom made stainless steel block. The compression tests were done using a flat-cylindrical aluminum indenter. The diameter of the diameter was 1.3 mm. The testing was conducted using a Bose Electroforce 3200 actuator. The force was measured using a 10 gram Honeywell miniature load cell. The displacement was measured using the Bose Electroforce 3200 internal linear variable differential transformer. The data was collected using LabVIEW. A static deflection test was conducted at 0.05 mm/s until fracture. The stress and strain curve was graphed and fit for the linear region to give young's modulus values.

Degradation Kinetics

Figure 5:
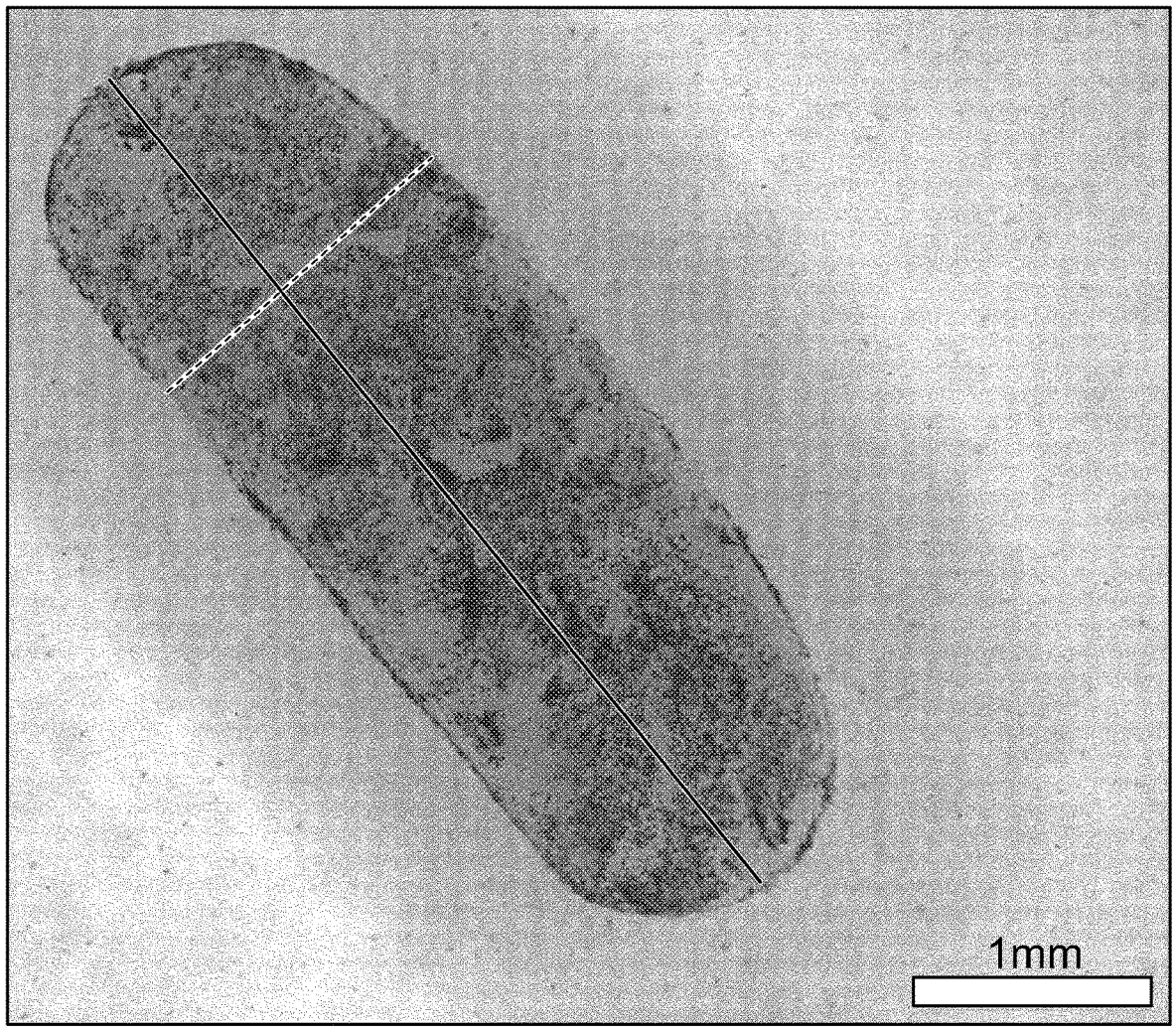
FIG. 5 is a photograph of a fibrin gel according to some embodiments. The dimensions are 1.5 mm (W)×5 mm (D)×200 µm (H).

Various gels were made using the sandwich method, with varying fibrinogen concentrations (40-60 mg/mL). Thrombin concentration did not appear to affect stiffness or degradation kinetics and was held constant at 100 U/mL. Varying plasminogen concentrations (0.8-4.0 U/mL) were loaded within the gel by mixing with the fibrinogen concentration prior to gelation. After formation, gels were punched using a custom sized, handheld hollow punch. The shape was oval, with a height of 1.5 mm and width of 5 mm (FIG. 5). The punched gels were incubated in various concentrations of tPA solution (0.1-1,000 U/mL). Over time, samples were taken of the suspension solution. To elucidate the effect of each variable (i.e., fibrinogen, plasminogen, and tPA concentrations), each was varied while holding the other two constant.

The fibrin degradation products (FDP) were quantified using a 660 nm Protein Assay, following the manufacturer's protocol. A standard curve of known FDP concentrations was used to obtain concentrations from absorbance values. A graph of concentration vs time was utilized to obtain a rate constant, using an exponential fit model.

Detachment of Fibrin/RPE Implant

Detachment of cells was attained both prior and post fibrin gel apposition. Cells on membrane supports were washed with PBS. The cells were incubated in basal 750 U/mL purified collagenase (Worthington) or 1 U/mL dispase in DMEM (Stem Cell Tech) up to 30 minutes. The transwell was removed and dried, while the membrane was cut and placed on top of parafilm. Fibrin was then sprayed on top, and allowed to fully gel. Alternatively, the sandwich method was used to appose the fibrinogen and thrombin mixture on the apical RPE monolayer and allowed to fully gel. After hydration, forceps were used to peel off the fibrin/RPE system (FRPE). The FRPE was then incubated in culture media.

Alternatively, RPE on membrane supports were washed with PBS. Once the PBS was removed, fibrin was sprayed on top and allowed to fully gel. After hydration, the cells were incubated in basal 750 U/mL purified collagenase or 1 U/mL dispase in DMEM up to 30 minutes. The membrane was carefully cut off and placed in a petri dish and submerged with PBS. The FRPE was then peeled off using forceps, or scraped off using a cell scraper.

FRPE Staining and Imaging

To determine the maintenance of monolayer phenotype, the FRPE was stained for ZO-1, a cell-cell junctional protein found in epithelial cells. FRPE samples were punched and fixed in 10% formalin for 1 hour. Staining was done as described elsewhere ((Johnson et al., *Invest. Ophthalmol. Vis. Sci* 56:4619-4630 (2015)). Fixed cells were blocked with NGS, incubated overnight at 4° C. in primary antibody, and incubated 2 hours in secondary antibody. Samples were mounted on glass slide using aquamount and imaged under Nikon Fluorescent microscope.

TEM images were obtained to view the interaction of the fibrin and RPE. FRPE samples were fixed in 2.5% glutaraldehyde for 1 hour. Fixed samples were processed for resin embedment, and 0.5 μm sections were cut and mounted. Imaging was done on a TEM microscope.

Live/Dead Assay

Punched FRPE implants were monitored over time using bright field microscopy. To determine cell viability, a live/dead kit was utilized on the FRPE, per manufacturer's protocol. Live cells were visualized under FITC spectrum (Absorbance: 495 nm; Emission: 520 nm), and dead cells were visualized under TRITC spectrum (Absorbance: 543 nm; Emission: 560 nm). Cell viability was calculated as a percent (live stained cells divided by total cells visualized).

PCR

PCR was accomplished on cells to confirm their functionality 24 hours after detachment from culture support and 24 hours after degradation of fibrin support. Markers included PEDF, RPE65, Best1, and control.

Results

FIG. 5 shows the success of attaching fibrin to the apical surface of the RPE and detachment from culture surface using dispase. After mechanical punching, the cells are still adherent to the fibrin.

Figure 6:
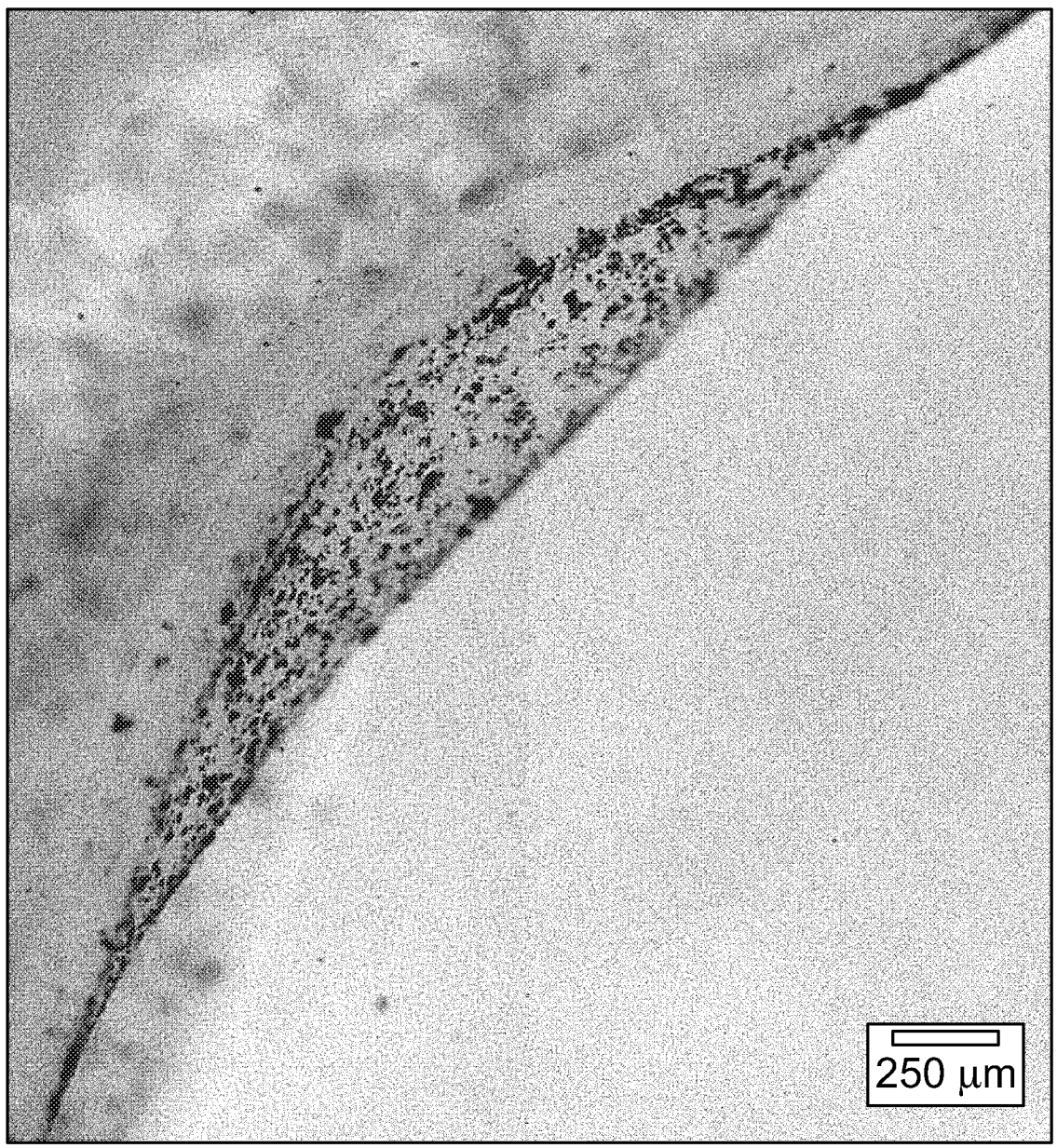
FIG. 6 is a photograph of apical fibrin attached to an RPE monolayer.
Figure 7:
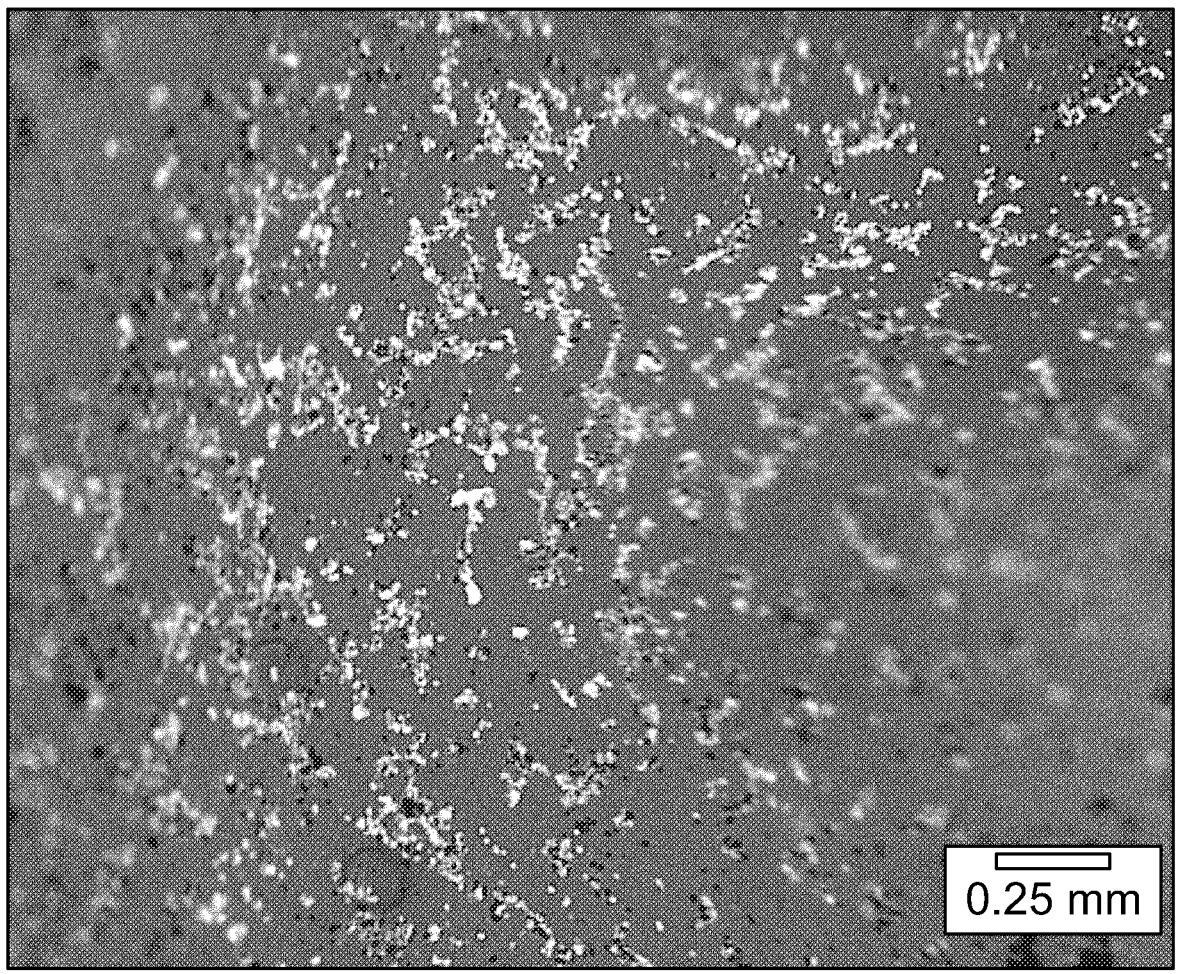
FIG. 7 is a photograph of live/dead staining of an RPE monolayer attached to apical fibrin. Attached cells are alive 2 hours later.
Figure 8:
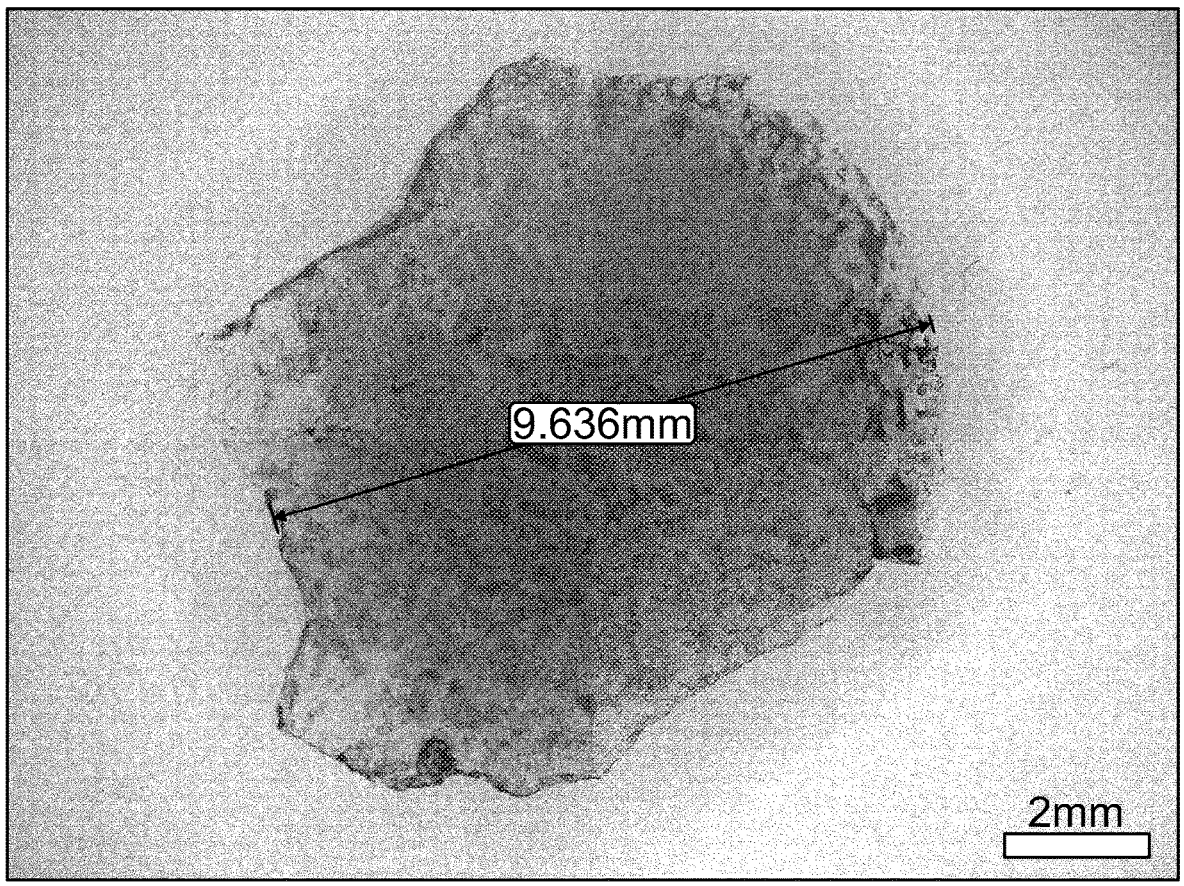
FIG. 8 is a photograph of an RPE monolayer attached to apical fibrin. The image shows a continuous monolayer attached to fibrin.
Figure 9:
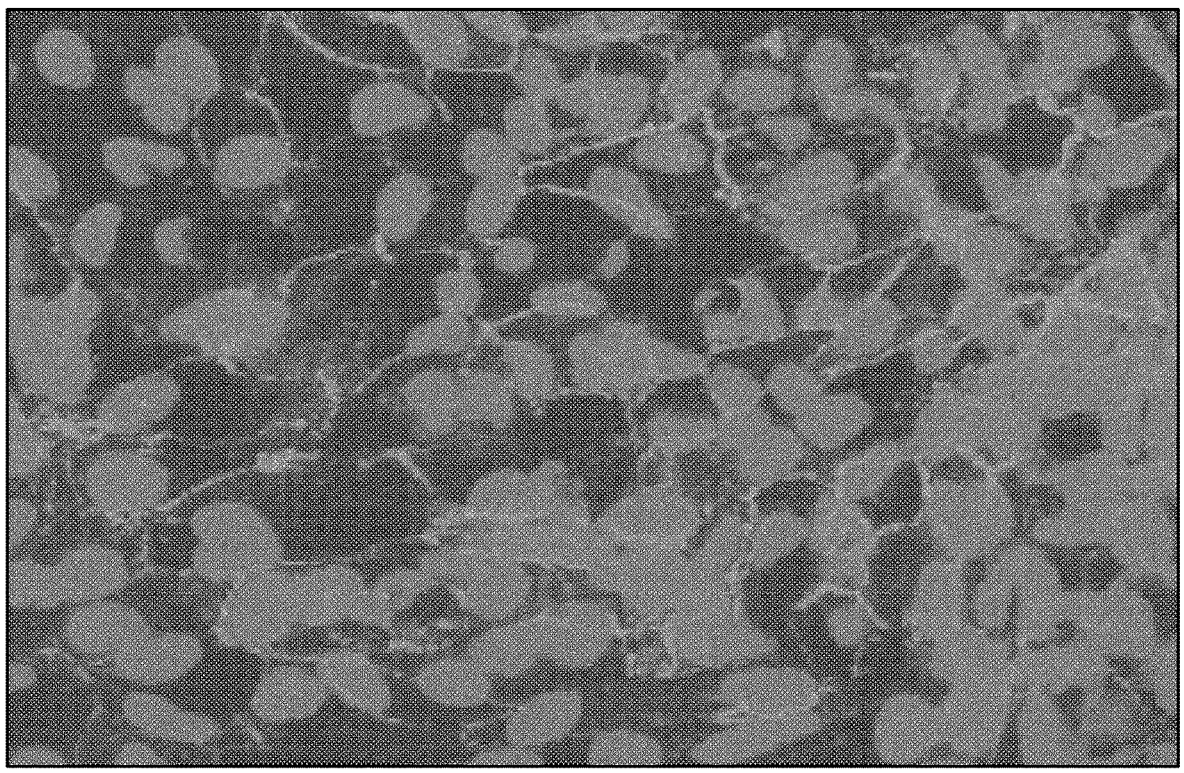
FIG. 9 is a photograph of ZO-1, a cell-cell tight junction protein, staining (red) and a DAPI (blue) staining of cell nuclei.
Figure 10:
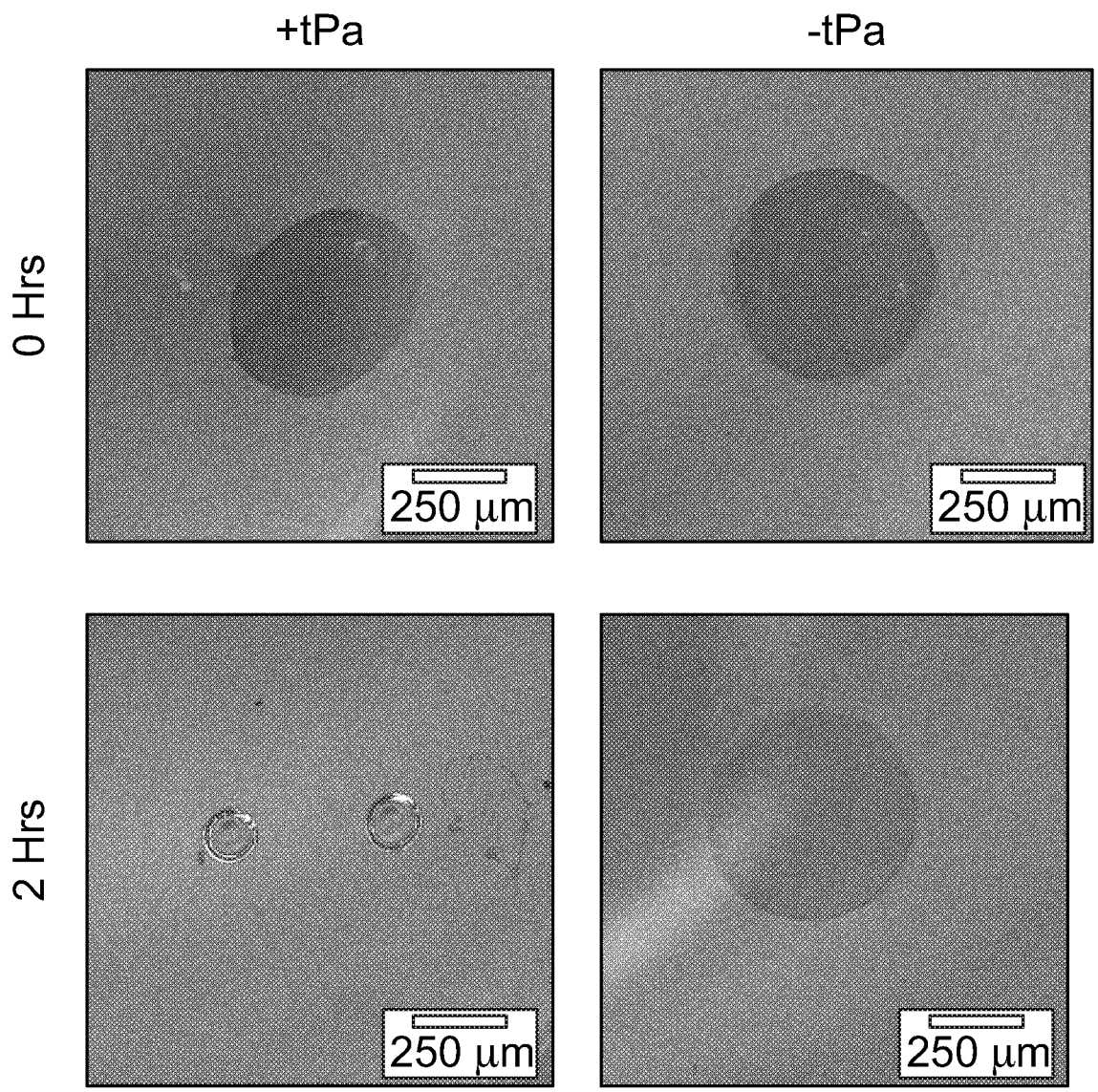
FIG. 10 contains photographs showing biomaterial degradation of fibrin following treatment with tissue plasminogen activator (tPA) for two hours. The range of time of fibrin degradation can be from one hour to 72 hours.

RPE cells were attached to the surface of the gel (FIG. 6), and the presence of calcein-AM staining suggests that the cells attached to the fibrin were still alive (FIG. 7). The successful attachment of fibrin to the apical surface of the RPE monolayer with large regions maintaining monolayer and pigmentation was observed (FIG. 8). The scale showed how scalable this method was for larger implant generation. DAPI (blue) and ZO-1(red) revealed the staining of RPE monolayers attached apically to fibrin (FIG. 9). The presence of ZO-1 suggested the presence of the monolayer through cell-cell junctions. In the presence of plasminogen, tPA was used to dissolve the fibrin gel (FIG. 10). Without tPA, plasminogen was not activated, and the gel did not degrade.

Figure 11:
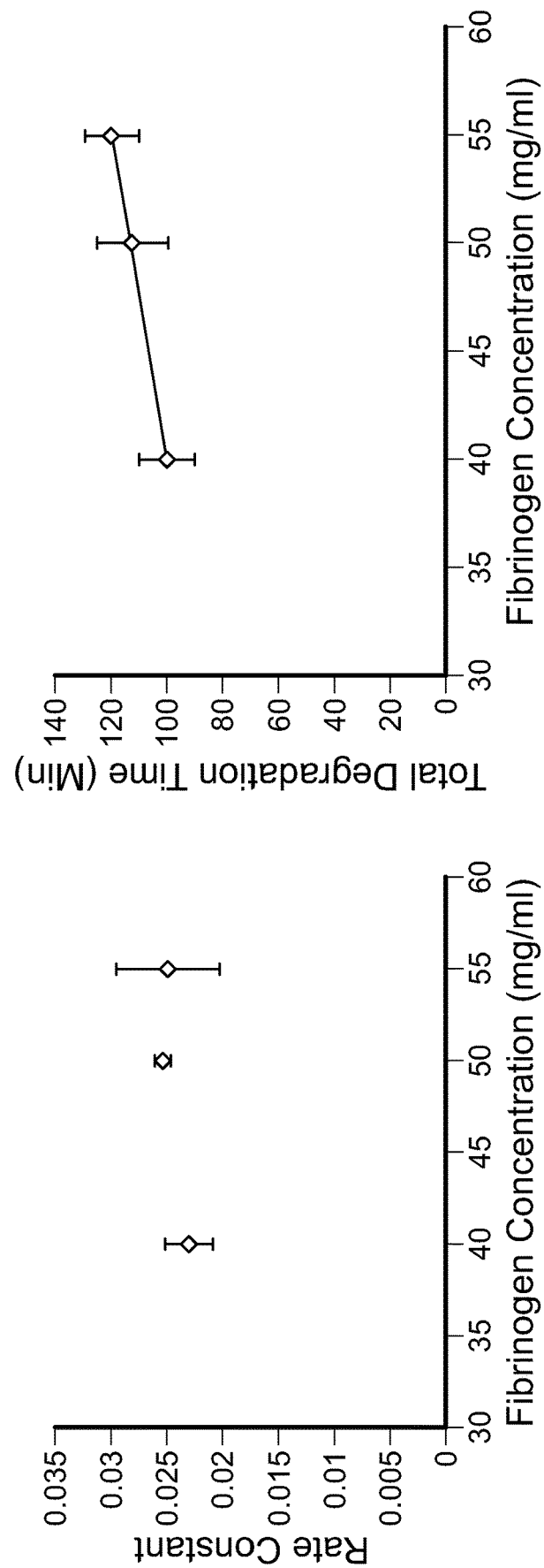
FIG. 11 contains graphs plotting the kinetics of degradation when varying fibrinogen concentrations. Plasminogen and tPA concentrations were fixed. Degradation was independent of rate constant. A linear relationship was observed between fibrinogen concentration and degradation time.
Figure 12:
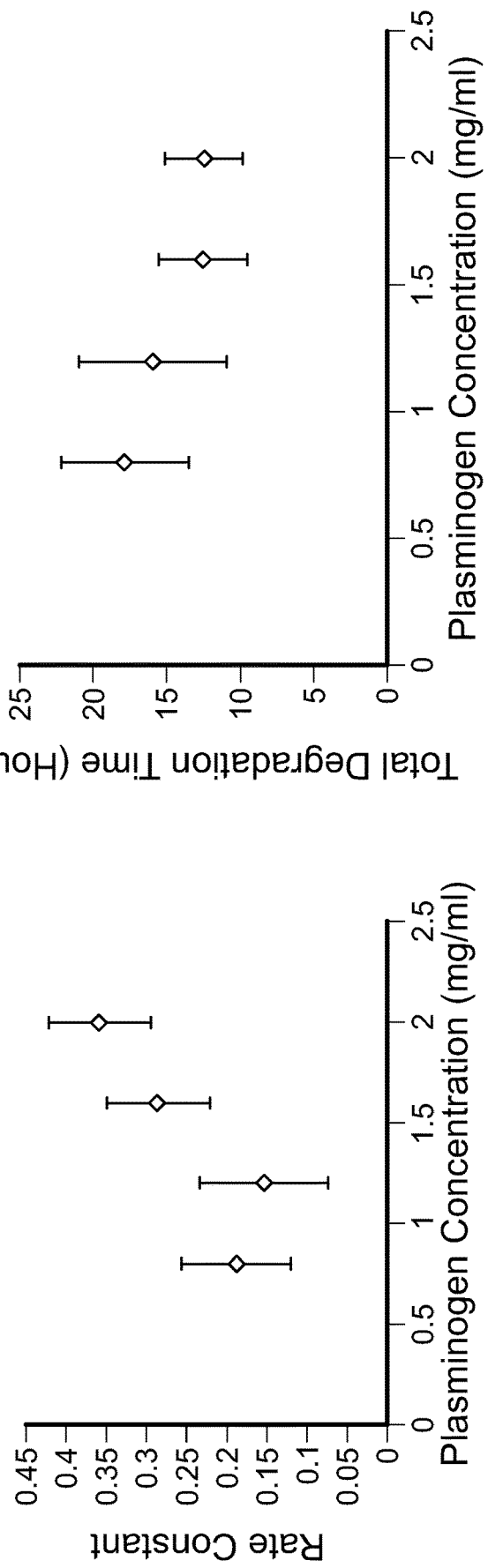
FIG. 12 contains graphs plotting the kinetics of degradation when varying plasminogen concentrations. Fibrinogen and tPA concentrations were fixed. Rate constant was dependent on plasminogen concentrations. A non-linear relationship was observed between plasminogen concentration and degradation time.
Figure 13:
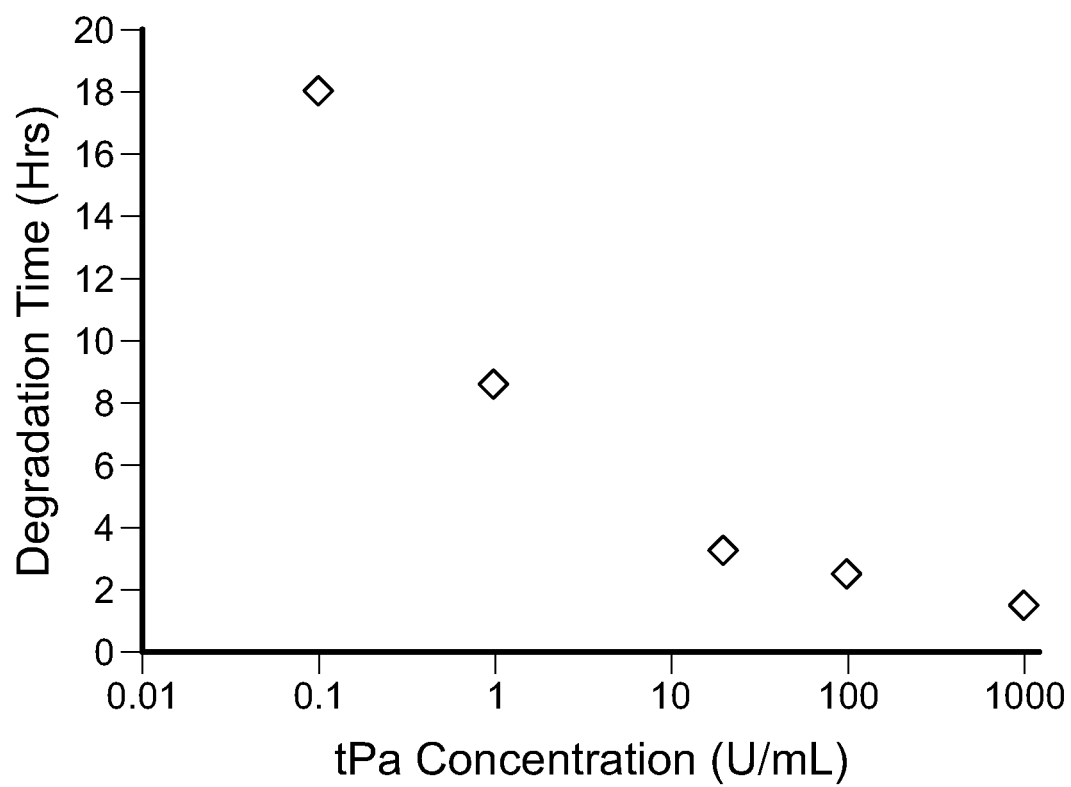
FIG. 13 is a graph plotting the kinetics of degradation when varying tPA concentrations. Fibrinogen and plasminogen concentrations were fixed. A large range of degradation times was observed.
Figure 14A:
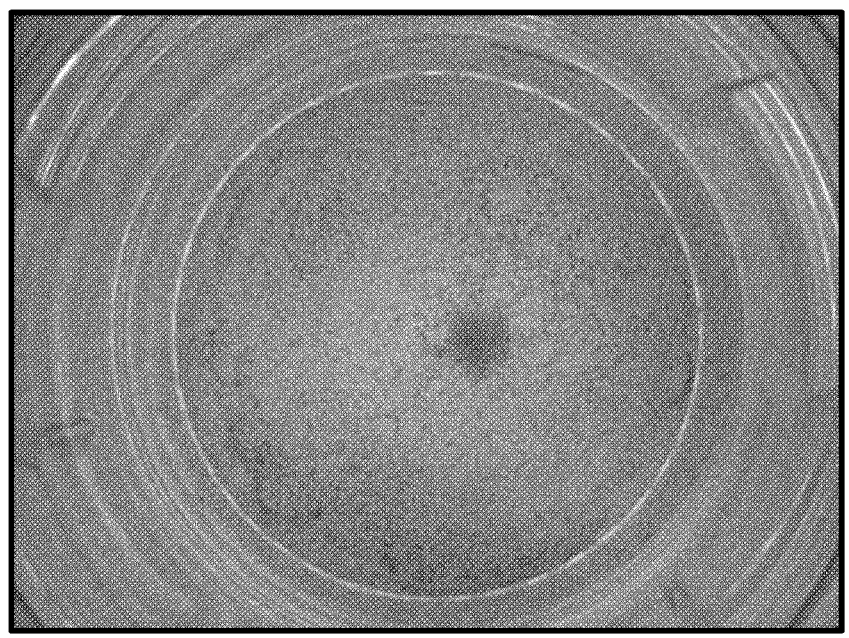
FIGS. 14A-C are images of plates containing induced pluripotent stem cell-derived (iPSC) retinal pigment epithelial (RPE) cells in a fibrin gel, cultured for two weeks in media without Aprotinin (FIG. 14A) or containing Aprotinin on plates with (FIG. 14B) or without (FIG. 14C) a geltrex coating. The inclusion of Aprotinin in the media appeared to prevent fibrin gel degradation.
Figure 14B:
Figure 14C:
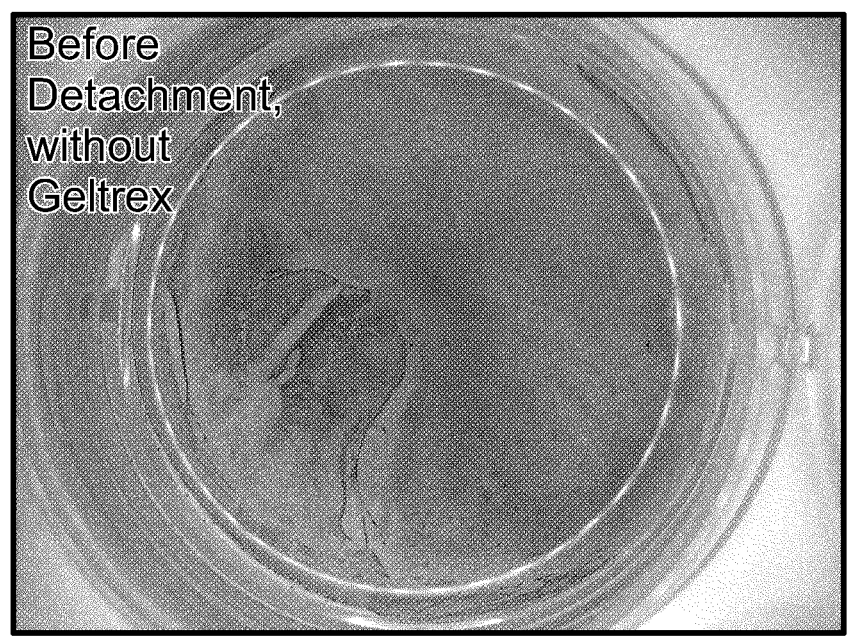

With fixed plasminogen and tPA concentrations, fibrinogen concentration had no effect on the degradation kinetics of the gel, as the rate constant was independent of fibrinogen concentration (p=0.35) (FIG. 11). With fixed fibrinogen and tPA concentrations, plasminogen concentration had an effect on degradation kinetics of the gel, as the rate constant increased with increasing plasminogen concentration (p=0.005) (FIG. 12). Thus, the total degradation time was reduced exponentially by increasing plasminogen concentration. With fixed fibrinogen and plasminogen concentrations, tPA concentration increases correlated to exponential decay in the degradation time (FIG. 13). The culture of RPE on fibrin scaffold was observed without aprotinin (FIG. 14A), where the RPE degraded the fibrin substrate within 3-4 days, causing many of the cells to die. Very few cells remained, and no phenotype of monolayer formation was observed. By including aprotinin in the culture media, RPE survival and monolayer formation were observed (FIG. 14B). This formation appeared to be independent of geltrex coating, suggesting the RPE can attach directly to fibrin (FIG. 14C).

Figure 15A:
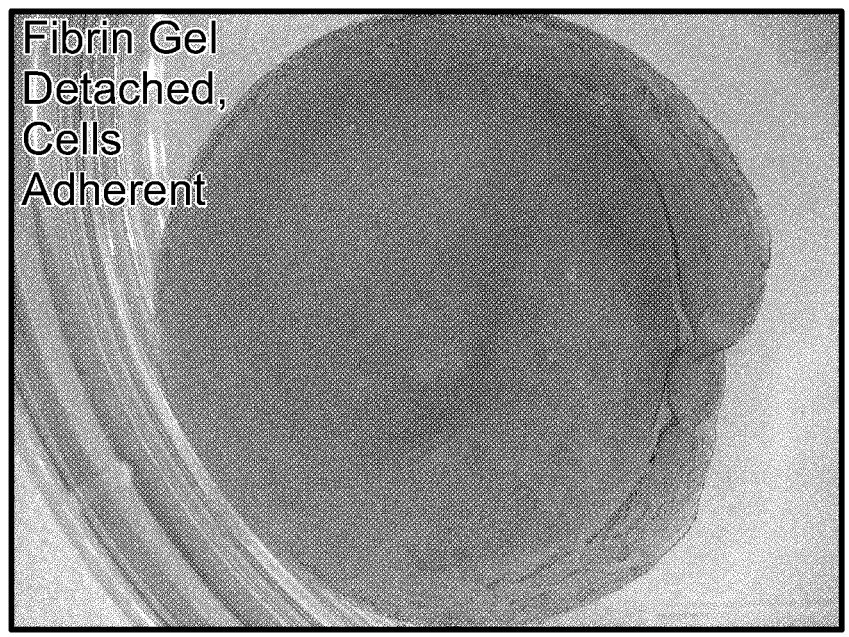
FIGS. 15A and 15B are images of plates containing iPSC-RPE cells cultured on a basal fibrin gel with Aprotinin, after detachment of the gel from the plates. The cells remained adherent after the gel was detached (FIG. 15A), and there was minimal cell removal after the gel was cut (FIG. 15B).
Figure 15B:
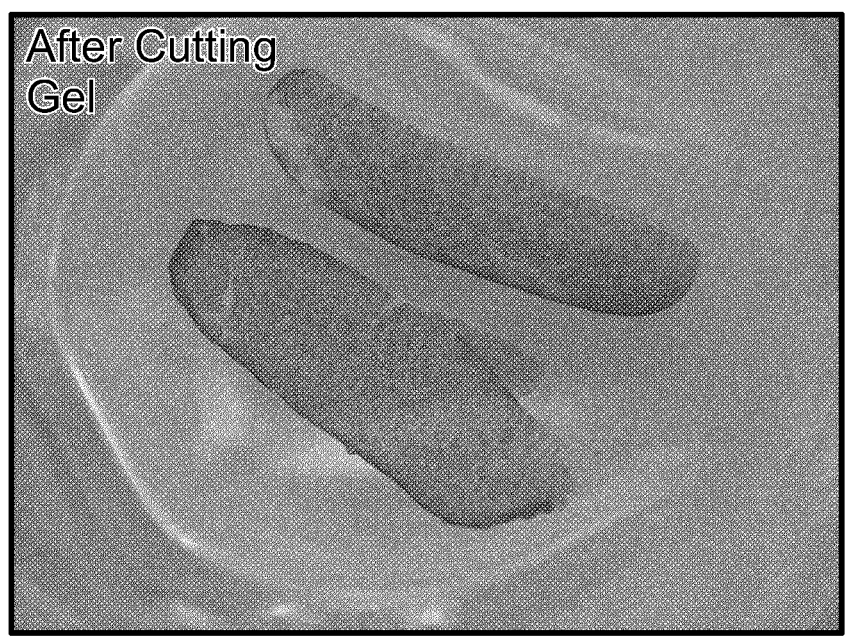

The mobilization of the fibrin basal support RPE culture was observed (FIG. 15A), and the RPE remained attached after mechanical punching (FIG. 15B).

Figure 16A:
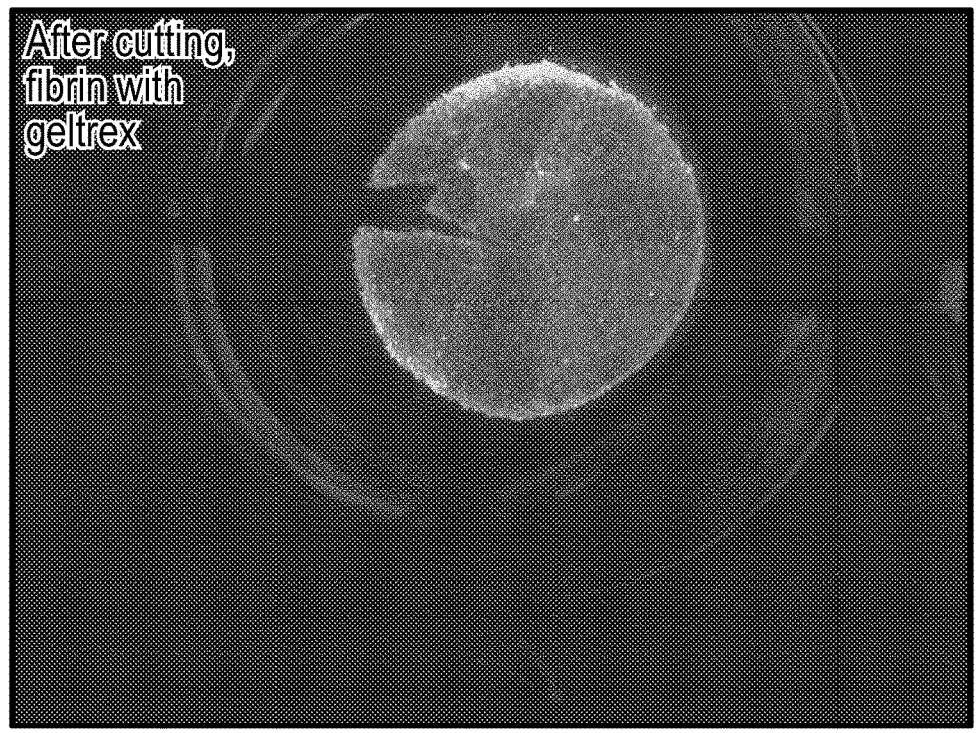
FIGS. 16A and 16B are images iPSC-RPE cells that were cultured in a fibrin gel with media containing Aprotinin, on plates with (FIG. 16A) or without (FIG. 16B) a geltrex coating, after detachment and cutting of the gel. Cells were stained with calcein-AM, indicating that they remained viable after detachment and cutting, and that geltrex may not be required for viability.

RPE attached to fibrin basal support remained viable after mechanical punching (FIG. 16). Further, the viability and adherence to the substrate was independent of the geltrex coating.

Figure 17:
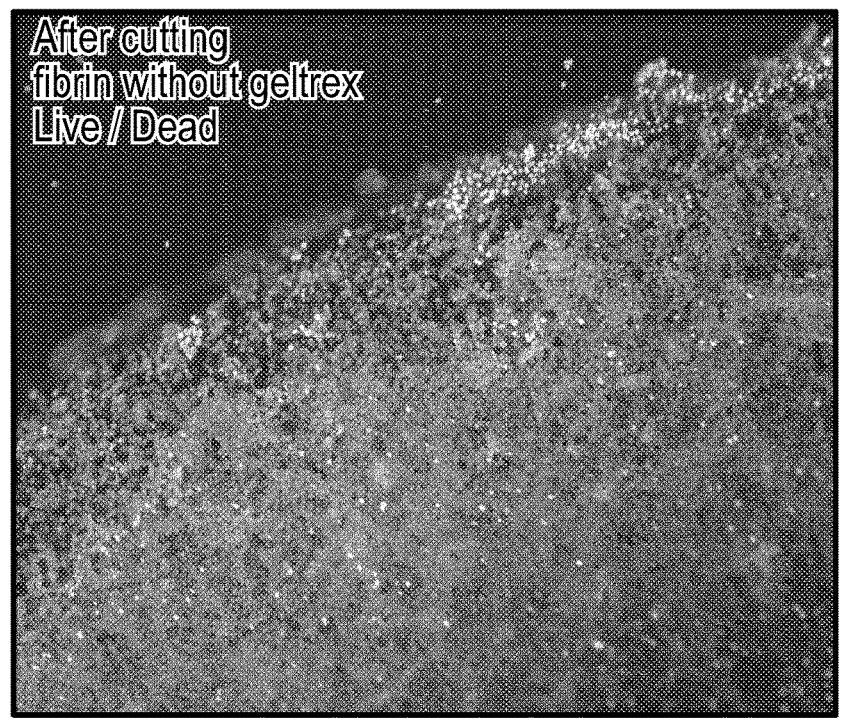
FIG. 17 is an image of iPSC-RPE cells at the edge of a fibrin gel that was cultured without geltrex coating. The gel was released from the plate and cut, and cells were stained with calcein-AM (Live) and ethidium homodimer (Dead). Live cells appear green, while dead cells are red.

A close up of a live/dead image of a punched fibrin basal supported-RPE was obtained (FIG. 17). The extreme edge revealed an increased loss of cell viability, likely due to the stress enduring during the mechanical punch. The cell viability in this region was 83.1%.

Figure 18A:
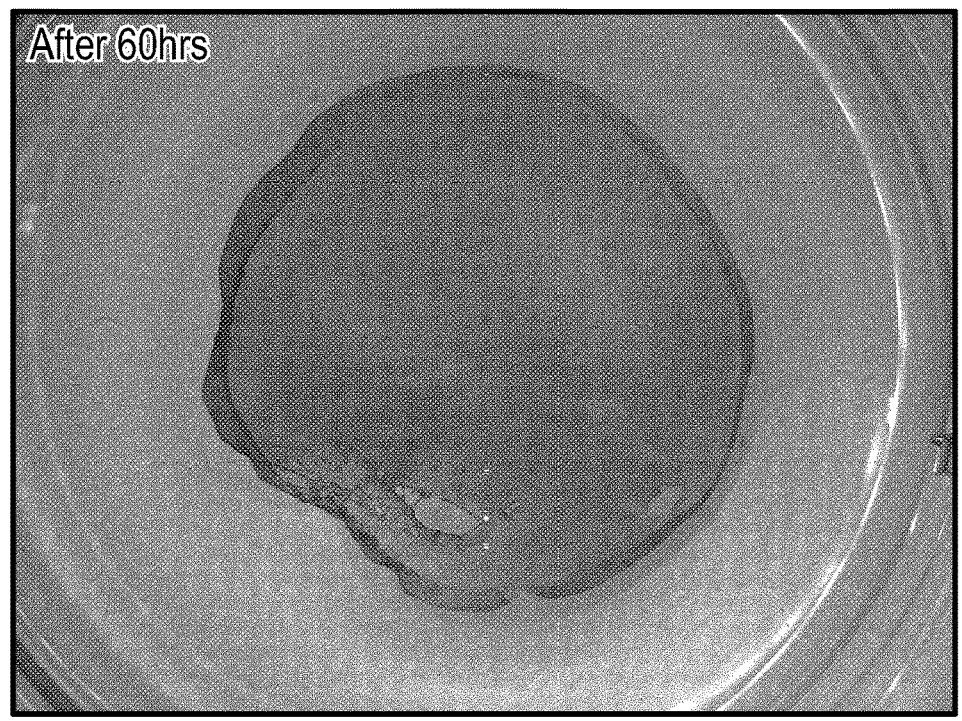
FIGS. 18A and 18B are images of plates containing iPSC-RPE cells cultured in a fibrin gel, which was then degraded by digestion with 0.1 U/ml plasminogen and 22 U/ml tissue plasminogen activator (tPA) for 60 (FIG. 18A) or 96 (FIG. 18B) hours. The cells detached from the plates as a monolayer.
Figure 18B:
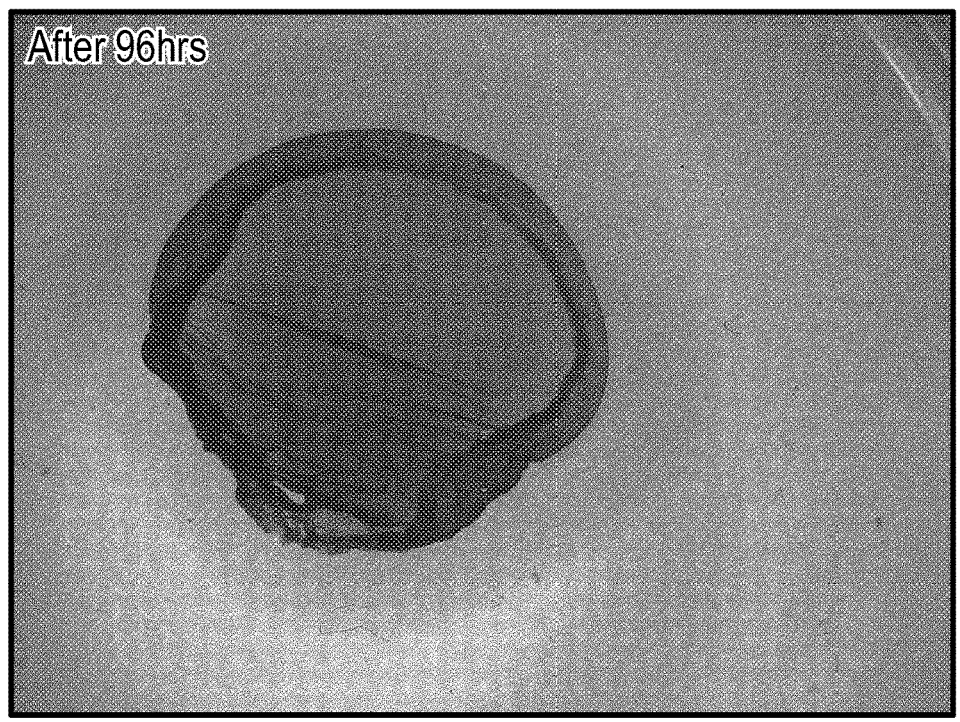

A time lapse degradation of the fibrin basal support was obtained (FIG. 18). After 60 hours, the edge of the gel degraded, showing the monolayer curling onto itself. After 96 hours, more than 50% of the gel degraded, and the remaining RPE monolayer was curling and folding onto itself. The gel was completed degraded after 120 hours. This result demonstrated a need of the mechanical support from the fibrin in order to maintain the flat, wrinkle-free phenotype of the RPE.

Figure 19:
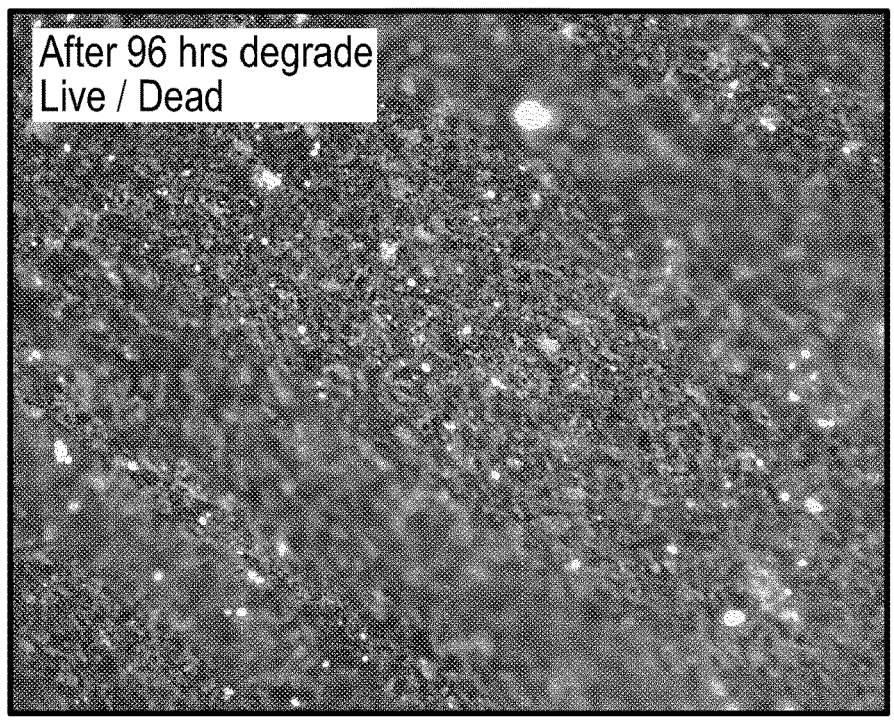
FIG. 19 is an image of iPSC-RPE cells in a monolayer after the fibrin gel was digested for 96 hours with plasminogen and tPA. Cells were stained with calcein-AM (Live) and ethidium homodimer (Dead); live cells appear green and dead cells appear red.

A close up of a live/dead image of the RPE monolayer in a region where the gel completed degraded was obtained (FIG. 19). The folds were viewed as out of focus regions. Overall, cell viability remained high and was comparable to viability of cells prior to degradation.

Figure 29:
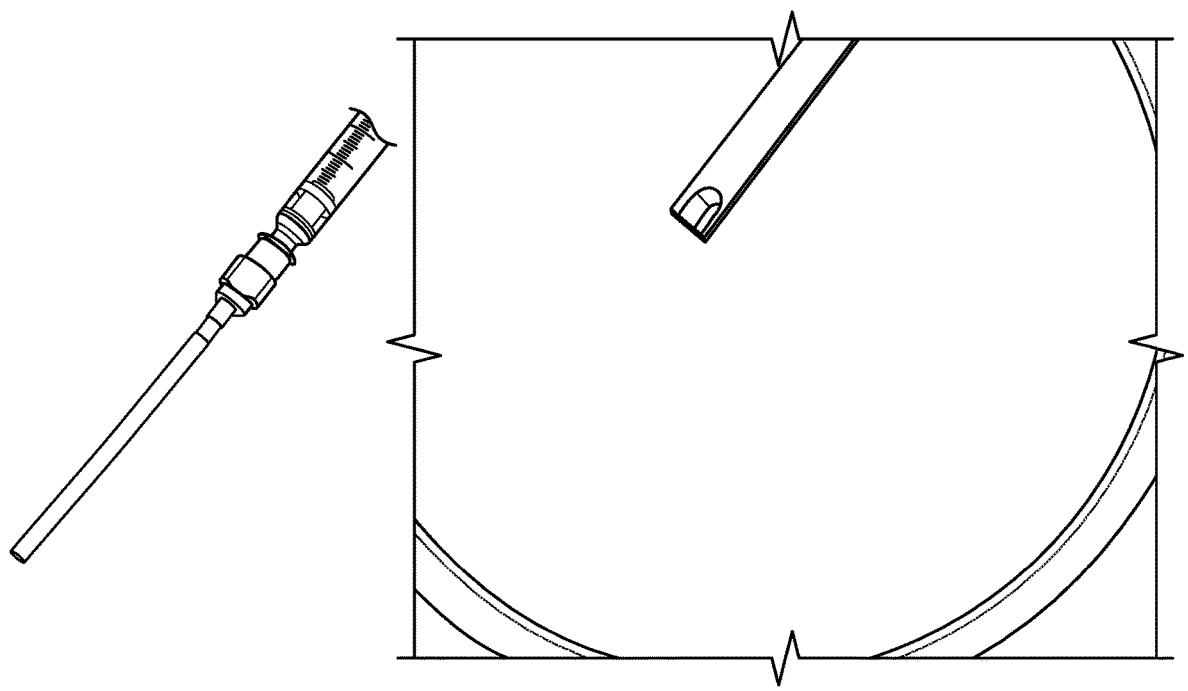
FIG. 29 contains photographs of one prototype of an implantation device for implanting RPE monolayer/fibrin implants into an eye.
Figure 30:
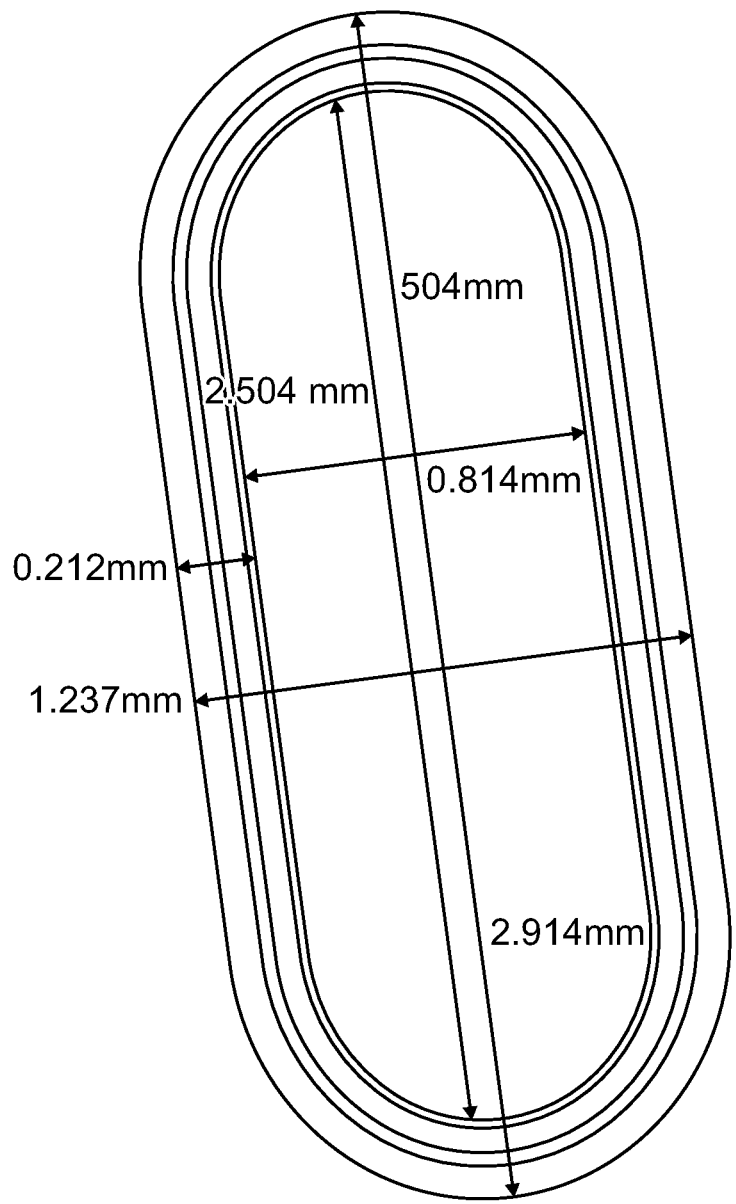
FIG. 30 is a photograph of an implant that can be delivered via the prototype of FIG. 29. The length can range from about 0.1 mm to about 3 mm, and the width can range from about 0.1 to about 2 mm.

The use of a surgical tool for delivering a RPE/fibrin implant was shown (FIG. 29). The tool used the hydrostatic pressure to flow the implant in and out of the device.

These results demonstrate that an appropriate stiffness can be achieved using a fibrinogen concentration of 40-60 mg/mL and that the gel thickness can be from about 50 μm to about 300 μm (e.g., from about 100 μm to about 200 μm, or from about 50 μm to about 200 μm). These results also demonstrate that cell-cell junctions can remain intact following treatment with collagenase and plasminogen.

The results provided herein demonstrate that the degradation kinetics of fibrin substrate can be varied from about 1.5 hours to about 20 hours by adjusting fibrinogen, plasminogen, and tPA concentrations.

Example 2—Effects of Aprotinin on Fibrin Attachment and Cell Viability

Studies were conducted to determine the effect of Aprotinin on fibrin gel attachment and maintenance, and on cell viability. iPSC-RPE cells were cultured for two weeks on a fibrin gel with (FIG. 14B) and without (FIG. 14C) geltrex coating, in media containing 50 U/mL Aprotinin. The inclusion of Aprotinin in the media appeared to prevent fibrin gel degradation. In addition, these studies indicated that attachment of the cells to the fibrin gel may occur independent of the presence of geltrex. The cells remained adherent after the gel was released from the plates (FIG. 15A), and there was minimal cell removal after the gel was cut (FIG. 15B).

Figure 16B:

To assess the viability of iPSC-RPE cells in fibrin gel after culture with Aprotinin for two weeks, followed by detachment and cutting of the gel, cells were stained with calcein-AM (Live) and ethidium homodimer (Dead). The cells remained viable after detachment and cutting, whether geltrex was present (FIG. 16A) or absent (FIG. 16B). A closer inspection of the cells at the edge of a gel cultured with Aprotinin, and with or without geltrex, after release from the plate and cutting, revealed that most cells were viable, although some dead cells were apparent around the periphery of the gel (FIG. 17).

To evaluate the effects of gel degradation on the cultured cells, a fibrin gel containing iPSC-RPE cells was degraded by digestion with 0.1 U/mL plasminogen and 22 U/mL tPA. Images were taken at 60 (FIG. 18A) and 96 (FIG. 18B) hours, showing that the cells detached from the plates as a monolayer. Cells in the monolayer were stained with calcein-AM (Live) and ethidium homodimer (Dead) to evaluate viability after 96 hours of gel digestion, showing most of the cells remained alive (FIG. 19).

Example 3—Protocol for Retinal Pigment Epithelium Monolayer with Apical Fibrin

1) Gel 2.5 mg/mL collagen onto cellulose ester membrane filter insert.
   a. 1.0-5.0 mg/mL collagen.
   b. Cellulose ester, polycarbonate, PTFE, TCPS membrane filter.

2) Coat the collagen surface with 1:5 dilution of matrigel.
   a. Range: 1:1-1:50 dilution.
   b. Matrigel, geltrex or purified laminin.
3) Plate cells at 0.5×10$^6$ cells/cm$^2$.
   a. 0.1-2.0×10$^6$ cells/cm$^2$.
4) Culture for about 2 weeks.
   a. 1-6 weeks.
5) Wash cells with PBS.
6) Dry cell surface.
7) Spray 80 μL of mixed 50 mg/mL fibrinogen, 2 U/mL plasminogen, and 100 U/mL thrombin, at total flow rate of 80 uL/sec, 0.8 bar for 1 second at a height of 10 cm.
   a. Spray 30-200 μL of mix.
   b. 30-70 mg/mL fibrinogen.
   c. 0.1-4.0 U/mL plasminogen.
   d. 10-600 U/mL thrombin.
   e. 30-400 μL/seconds flow rate.
   f. 0.6-1.2 bar.
   g. 5-15 cm height.
8) Allow fibrinogen to gel 1 hour 37° C.
   a. Gel 30 minutes to 2 hours.
9) Rehydrate with PBS.
10) Detach monolayer by placing insert on 750 U/mL collagenase.
    a. 400-1500 U/mL collagenase.
11) Wash gently with PBS.
12) Transfer fibrin-RPE implant to flat surface and punch out multiple implants.
13) Load implants into surgical device.
14) Prep eye for surgery.
15) Plunge implant into subretinal space.
16) Laser tack.
17) Tile multiple implants within subretinal space.
18) Close eye.
19) After 24 hours, intravitreal injection of 100 μL of 4,000 U/mL tissue plasminogen activator.
    a. 3-72 hours post surgery.
    b. 50-200 μL injection.
    c. 100-35,000 U/mL.

This protocol produces RPE monolayer supported by apical fibrin hydrogel.

Example 4—Protocol for Retinal Pigment Epithelium Monolayer with Basal Fibrin Support 1) Plate mixed solution of 30 mg/mL fibrinogen and 100 U/mL thrombin to gel.
   a. 20-80 mg/mL fibrinogen.
   b. 10-600 U/mL thrombin.
   c. Swirl plate to ensure uniform spread.
   d. A mold is used to compress the gel to desired thickness.
   e. Thickness: 50 μm to 1 mm.
   f. Mixture is plated onto TCPS, polycarbonate, cellulose ester.
   g. Alternatively, flat sheets of fibrin gel are pre-formed using a mold and mounted to a cell culture insert.
   h. Mixture is sprayed onto surface.
2) Coat the gel surface with 1:5 dilution matrigel.
   a. Range: 1:1-1:50 dilution.
   b. Matrigel, geltrex, Laminin 521, Laminin 511.
   c. Coating step is not necessary.
3) Plate cells at 0.5×10$^6$ cells/cm$^2$.
   a. 0.1-2.0×10$^6$ cells/cm$^2$.
4) Culture for 2 weeks with media with 50 U/mL Aprotinin.
   a. Range: 20-150 U/mL
   b. 1-10 weeks.
5) Mobilize fibrin-RPE by peeling fibrin from support.
6) Optional: Load plasminogen into basal fibrin gel.
   a. Incubate fibrin-RPE in plasminogen solution.
      i. 0.001-40 U/mL (e.g., 1-40 U/mL) plasminogen.
      ii. 2-6 hours.
7) Optional: Apical gel for additional support.
   a. Spray 80 μL of mixed 50 mg/mL fibrinogen, 2 U/mL plasminogen, and 100 U/mL thrombin, at total flow rate of 80 μL/second, 0.8 bar for 1 second at a height of 10 cm.
      i. Spray 30-200 μL of mix.
      ii. 30-70 mg/mL fibrinogen.
      iii. 0.1-4.0 U/mL plasminogen.
      iv. 10-600 U/mL thrombin.
      v. 30-400 μL/second flow rate.
      vi. 0.6-1.2 bar.
      vii. 5-15 cm height.
   b. Allow fibrinogen to gel 1 hour 37° C.
      i. Gel 30 minutes to 2 hours.
8) Transfer fibrin-RPE implant to flat surface and punch out multiple implants.
9) Load implants into surgical device.
10) Prep eye for surgery.
11) Plunge implant into subretinal space.
12) Laser tack.
13) Tile multiple implants within subretinal space.
14) Close eye.
15) After 24 hours, intravitreal injection of 100 μL of 4,000 U/mL tissue plasminogen activator.
    a. 3-72 hours post surgery.
    b. 50-200 μL injection.
    c. 100-35,000 U/mL.

This protocol produces RPE monolayer with basal fibrin support.

Example 5—Eye Treatment Protocol

A clinic obtains a patient skin biopsy and sends it to a GMP facility to produce iPSC-RPE cells as described elsewhere (Sonoda et al., *Nat. Protoc.*, 4:662-673 (2009); Johnson et al., *Ophthalmol. Vis. Sci.*, 56:4619 (2015); Brandl et al., NeuroMolecular Med., 16:551-564 (2014); Idelson et al., *Cell Stem Cell.*, 5:396-408 (2009); and Carr et al., *Mol. Vis.*, 15:283-295 (2009)). The iPSC-RPE are cultured on fibrin hydrogels using the cell culture insert for up to 3 months. The RPE/fibrin gel is cut to specifications of the patient's need. The cut implants are loaded into the tip components of an implantation device, stored in culture media with or without plasminogen, and shipped to the clinic.

The clip component pre-loaded with the RPE/fibrin gel is inserted into the implantation device. The patient is prepped for surgery. A standard 3 port vitrectomy is performed, followed by formation of a bleb using a fine cannula, followed by a retinotomy using retinal scissors. An incision (e.g., a 3 mm or 1.5 mm incision) is made in the sclera (or retina with detachment). The tip of the implantation device is inserted into the eye in position under the retinotomy, and the implant is deployed. A laser is used to tack the implant in place. This is repeated with additional implants to cover the area being treated. The retinal detachment is closed using silicone oil or perfluorocarbon liquid tampenade. The scleral incision is sutured closed. tPA is intravitreally injected. The

Example 6—Fibrin Hydrogels as a Xeno-Free and Rapidly Degradable Support for Transplantation of RPE Monolayers The following was performed to confirm the suitability of fibrin as a substrate for RPE transplantation. A variety of fibrin hydrogels were produced by varying the concentrations of fibrinogen and thrombin to form a thin rigid hydrogel with defined parameters for degradation in the scale of hours. Subsequently, the optimized conditions were utilized to produce fibrin gels on which iPSC-RPE were cultured, forming well-differentiated monolayers. Finally, the fibrin support was degraded in vitro and the effects of this degradation on the RPE monolayer were assessed. The results provided herein demonstrate that fibrin hydrogels can be used as a long-lived substrate for the differentiation of RPE from stem cells that can then be rapidly degraded under controlled circumstances following delivery to the subretinal space.

Chemicals

Fibrinogen and thrombin were obtained from Ethicon (Somerville, N.J.) (Evicel, fibrinogen at 60 mg/mL), Baxter (Deerfield, Ill.) (Tisseel, fibrinogen at 95 mg/mL), and Sigma-Aldrich (St Louis, Mo.) (fibrinogen at 57 mg/mL). Plasminogen and recombinant tissue plasminogen activator (tPA) were obtained from Sigma-Aldrich.

Formation of Thin Layer Fibrin Gels

Fibrin gels were formed by varying the fibrinogen concentration and thrombin concentration. Initial studies showed minimal variation with thrombin concentration, and all experiments utilized a final concentration of 100 U/mL thrombin. For acellular experiments, thin layer gels were formed by using a custom thickness mold, which consisted of two plates of polycarbonate and 2 layers of parafilm with a defined thickness spacer ranging from 0 to 200 µm. A mixture of fibrinogen and thrombin solutions was sandwiched between the two layers immediately after mixing, and the solution was allowed to gel for 1-2 hours at 37° C. in a humidified incubator. After the top plate and parafilm were removed, the gels were hydrated and washed in PBS. A custom mechanical punch was used to cut out similar sized gels, in an oblong shape, 1.5 mm×5 mm. Forceps were carefully used to manipulate the gels.

Gel Thickness Measure

Punched gels were imaged using OCT to determine thickness. An Envisu R4110 (Leica; Wetzlar, Germany) was set up using an AIM table, with the camera and attached telecentric lens faced down on the gel. Prior to imaging, the gels were placed in PBS in a clear 60 mm petri-dish. A and B scans were taken of the gels, and the thickness per gel was averaged across four random locations.

Electron Microscopy

Scanning electron microscopy (SEM) images were obtained of the fibrin hydrogel using a Hitachi S-4700 (Hitachi High Technologies; Schaumburg, Ill.) and Hitachi SEM software (V3.6). Gels were fixed in 2.5% paraformaldehyde and 1% glutaraldehyde in 0.1 M phosphate buffer pH 7 with divalent cations overnight. Gels were then critical-point dried using carbon dioxide, mounted on an aluminum stub, and sputter-coated for 60 seconds using gold-palladium.

Mechanics

Figure 34B:
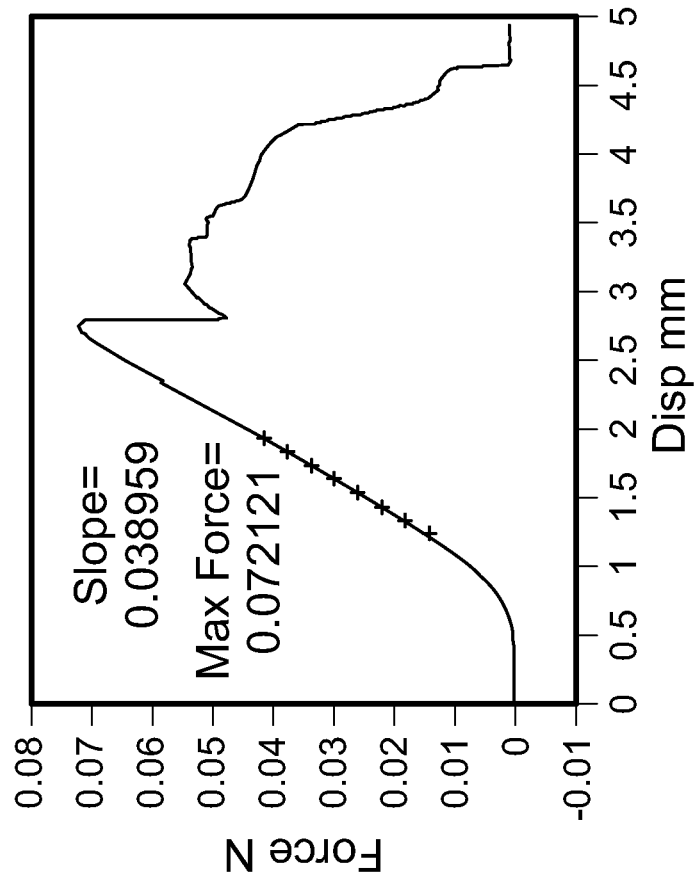
FIG. 34B shows a sample force versus displacement graph, from which slope (mechanical strength) and maximum force data are obtained.
Figure 34A:
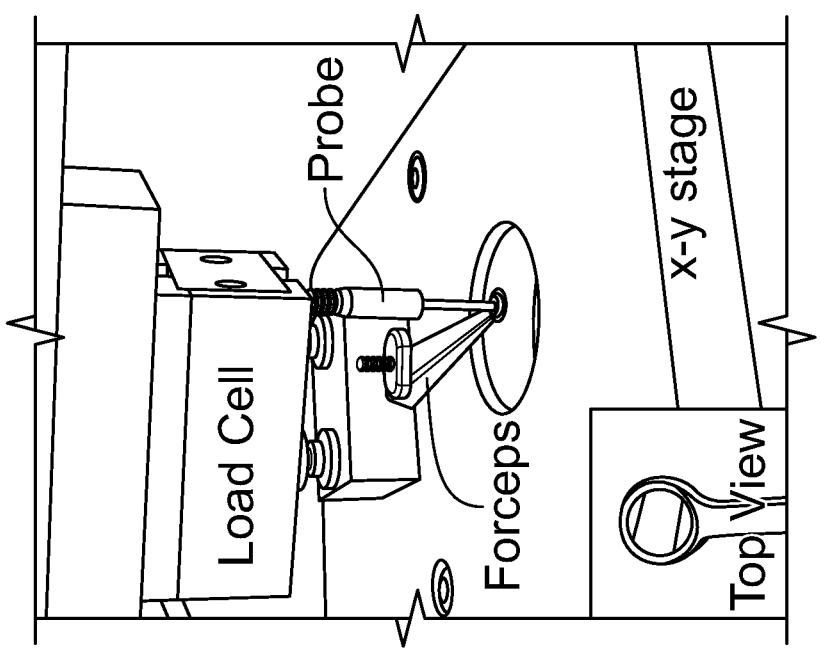
FIG. 34A shows an example of the testing setup.

Gel biomechanics were obtained using bulge testing using a setup described elsewhere (Uehara et al., *J. Bone Joint Surg. Am.*, 97:1792-1798 (2015)). Gels made with various fibrinogen concentrations and thicknesses were measured. Briefly, the gel was mounted to ring forceps (WPI; Sarasota, Fla.) with a 2 mm internal diameter, which was sanded to increase grip. The forceps were mounted to an XY stage (Klinger; Irvine, Calif.) to line up the indenter with the gel (FIG. 34A). The tests were conducted using a custom flat-cylindrical aluminum indenter with a 1.3 mm outer diameter. The testing was conducted on a custom-build z-stage driver. The force was measured using a 10 g miniature load cell (Honeywell; Morris Plains, N.J.), and the data was collected using LabVIEW V12.0 (National Instruments; Austin, Tex.). A static deflection test was conducted at 1 mm/second until fracture. The force and displacement curve was graphed and fit so that the linear region gave the mechanical stress values (FIG. 34B). Maximum load was also obtained as the peak of the curve.

Degradation Kinetics

Gel degradation kinetics were determined by varying the concentration of fibrinogen, plasminogen, or tissue plasminogen activator (tPA). Thrombin concentration did not appear to affect stiffness or degradation kinetics and was held constant at 10 U/mL. Identical sized gels (1.5 mm×5.0 mm oblong) were generated using a custom punch. The punched gels were incubated in various concentrations of plasminogen (0.01-1 U/mL) and tPA solution (0.1-1,000 U/mL). To elucidate the effect of each variable (fibrinogen, plasminogen, and tPA concentrations), each was varied while holding the other two constant.

Over time, samples were taken of the suspension solution. The fibrin degradation products (FDP) were quantified using a Pierce 660 nm Protein Assay (Life Technologies; Carlsbad, Calif.), following the manufacturer's protocol. A standard curve of known FDP concentrations was used to obtain concentrations from absorbance values. A graph of concentration vs time was utilized to obtain a rate constant, using an exponential fit model assuming first order kinetics.

Cells

The iPSC line 006-BIOTR-001 generated from a 21-year old Caucasian female donor was used (Johnson et al., *Investig. Ophthalmol. Vis. Sci.*, 56:4619 (2015)). iPSC-RPE cells were generated from this line by LAgen Laboratories (Rochester, Minn.) using a differentiation process described elsewhere (Johnson et al., *Investig. Ophthalmol. Vis. Sci.*, 56:4619 (2015)).

Fibrin gels were made by mixing fibrinogen (final: 30 mg/mL) and thrombin (final: 10 U/mL) solutions in the bottom of the culture surface (either 60 mm, 6 well plate, 12 well plate, or 12 well Transwell), and a custom Teflon weight was used to flatten and smooth the gel surface. The gels were then incubated for 1-2 hours in 5% $CO_2$, 37° C. humid incubator. Gels were washed with PBS prior to plating.

RPE were passaged as described elsewhere (Johnson et al., *Investig. Ophthalmol. Vis. Sci.*, 56:4619 (2015)). Suspended cells were plated onto the fibrin or matrigel-coated surfaces at a density of $0.4$-$0.5 \times 10^6$ cells/mL. RPE differentiation media (RPEM (LAgen Laboratories), with 2% (v/v) B27 and 1% (v/v) antimycotic/antibiotic (Life Technologies)) was supplemented with varying concentrations of aprotinin to preserve the fibrin gel. Media was changed every 2 days. RPE were cultured on the gels for 6-10 weeks prior to use. When appropriate, RPE cultured on matrigel-coated tissue culture polystyrene was used as a positive control.

RPE Immunofluorescence

Immunofluorescence was used to visualize protein expression in the iPSC-RPE. Samples were fixed in 100% ice-cold methanol for 10 minutes at −20° C. Staining was as performed as described elsewhere (Johnson et al., *Investig. Ophthalmol. Vis. Sci.*, 56:4619 (2015)), using the following primary antibodies at a 1:1000 dilution: polyclonal rabbit-anti Best1 (pAB125); polyclonal rabbit-anti Ezrin (Cell Signaling; Danvers, Mass.); and polyclonal rabbit-anti ZO1 (Life Technologies). Samples were mounted on glass slides using Fluoromount and imaged using a Nikon E600 fluorescence microscope (Nikon; Tokyo, Japan).

Live/Dead Assay

A LIVE/DEAD Viability/Cytotoxicity kit (Live Technologies) was utilized per manufacturer's protocol to perform a live/dead assay. Live cells were visualized using a FITC filter (Absorbance: 495 nm/Emission: 520 nm), and dead cells were visualized using a TRITC filter (Absorbance: 543 nm/Emission: 560 nm). RPE monolayers cultured on fibrin were used before or after degradation. Degradation was achieved using 1 U/mL plasminogen with 100 U/mL tPA. Cell viability was calculated as the percent of live stained cells divided by total cells visualized. Results for experimental groups were normalized to control groups.

PCR

RPE cultured on fibrin were scraped into 1×DPBS, centrifuged for 5 minutes at 5,000 g at 4° C. Cells were lysed in Trizol, and total RNA was isolated using a total RNA isolation kit (Zymo; Irvine, Calif.). Total RNA was treated with RNase-free DNAse I (Roche Bio; Basel, Switzerland). cDNA was synthesized from total RNA using Superscript III reverse transcriptase (Life Technologies). Total RNA was primed with oligo dT (Life Technologies). Primers were designed using Primer-BLAST software (Ye et al., *BMC Bioinformatics*, 13:134 (2012)). Sendai Viral Primer sequences were from the CytoTune™-iPS 2.0 Sendai Reprogramming Kit. Primers were ordered desalted from IDT (Coralville, Iowa). Forty cycles of PCR using 10-100 ng of input cDNA and PowerUp Sybr Green Master Mix (Applied Biosystems; Foster City, Calif.) were done on an Applied Biosystems QuantStudio 5 qPCR instrument. PCR reactions were batched according to the annealing temperature of the primer sets. A gene was deemed present if the $C_T$ was less than 37 cycles.

ELISA

An ELISA assay kit (RND Systems; Minneapolis, Minn.) was used to quantify VEGF and PEDF secretion using pre-coated plates, following the manufacturer's protocol from media collected after 48 hours. Total protein was determined using a standard curve.

Western Blot

RPE were scraped from fibrin in TPI buffer with 1% Triton-X, 20 mM Tris, 150 mM NaCl, and 5 mM EDTA, pH 8.0. Cells were lysed for 1 hour at 4° C. Samples were diluted and resolved on a capillary electrophoresis-based western blot instrument (Protein Simple Wes; San Jose, Calif.) using manufacturer's solution kits and protocol. Primary antibodies included RPE65 (401.8B11.3D9), Bestrophin 1 (pAB125), CRALBP (B2), and β-actin (AC-15).

Statistics

Data was analyzed using JMP 10 (SAS; Cary, N.C.). For fibrin mechanical testing and degradation studies, a 1-way ANOVA test was used. For aprotinin toxicity studies, a 2-way ANOVA test was used. After ANOVA analysis, significance was tested amongst groups using a Tukey HSD test. For all cellular quantitative data, a student's t-test was used to compare individual groups. Statistical significance was considered for $p<0.05$.

Results

Gel Formation Mechanical Properties

The materials provided herein for RPE transplant can be designed to be thin, laminar sheets with sufficient strength to maintain flatness while being manipulated with surgical instruments. A custom mold (50 mm×50 mm square, 400 µm thick) was used to produce identical thickness gels while varying concentrations of fibrinogen and thrombin. Thrombin concentration did not affect mechanical properties of fibrin hydrogels made at concentrations above $1 \text{ U}^*\text{mL}^{-1}*\text{mg}^{-2}$ fibrinogen as described elsewhere (Rowe et al., *Acta Biomater* 3:59-67 (2007)). The following work was done with a fixed thrombin concentration (100 U/mL).

Figure 35A:
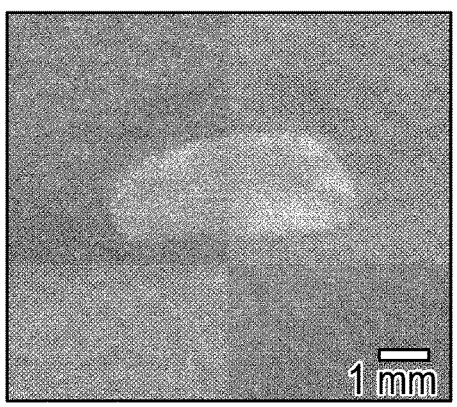
FIG. 35A shows a macroscopic image of the fibrin hydrogel after begin cut to the 1.5 mm by 5 mm geometry.
Figure 35B:
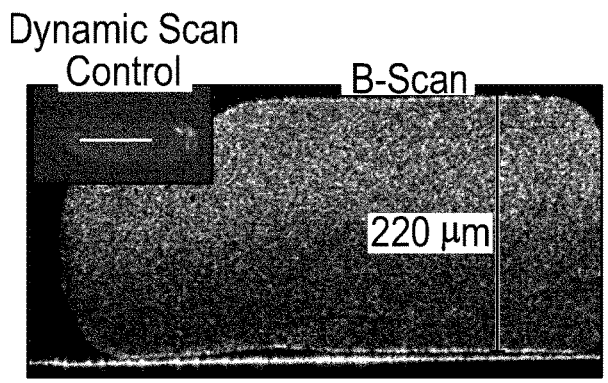
FIG. 35B shows a cross sectional view of the fibrin hydrogel using spectral domain optical coherence tomography.
Figure 35C:
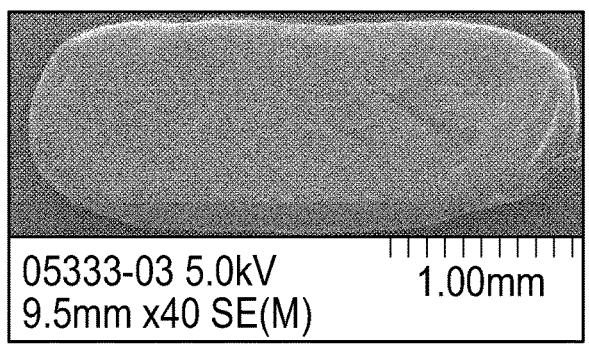
FIG. 35C shows a scanning electron microscope image of the surface of the fibrin hydrogel.
Figure 35D:
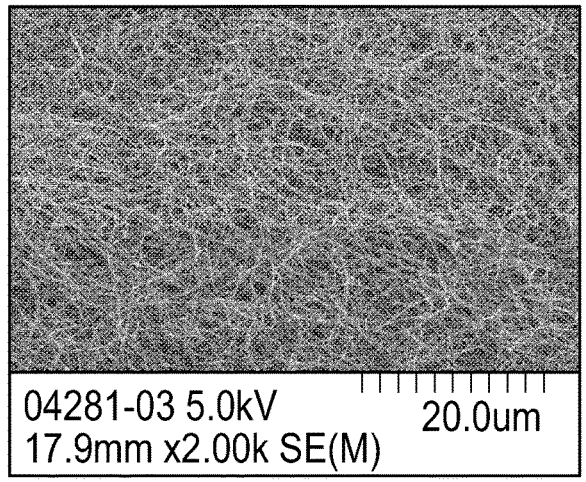
FIG. 35D shows a higher magnification of the fibrin hydrogel fibril structure using SEM.

Fibrin produced smooth, thin, and rigid gels that were opaque (FIG. 35A). No swelling of the fibrin gel was noticeable after hydration. The edges of the gels were well defined. OCT imaging demonstrated that the gels formed by this method had an average thickness of 200±30 µm (FIG. 35B), within the range expected based on the dimensions of the mold. SEM images of the fibrin gels indicated a smooth surface (FIG. 35C), with a fibrilar microstructure similar to that described elsewhere for fibrin (Filová et al., *J. Biomed. Mater. Res. A.*, 90A:55-69 (2009); FIG. 35D).

Figure 35E:
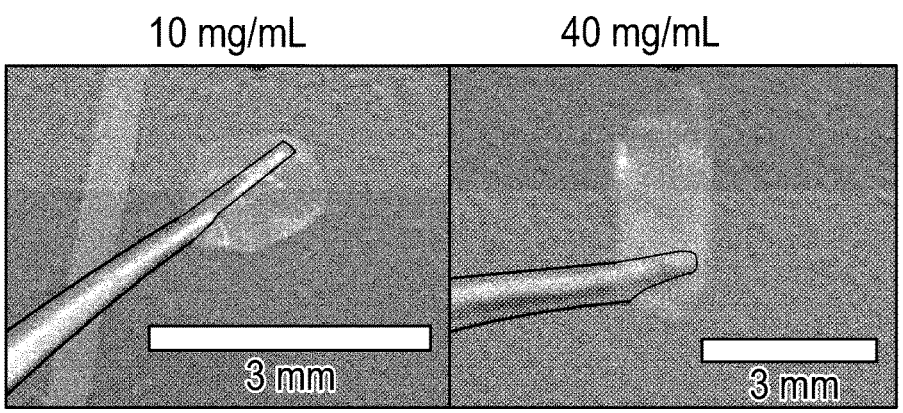
FIG. 35E shows that the fibrin hydrogel curls at lower fibrinogen concentrations such as 10 mg/mL, but have sufficient strength to retail its shape when formed with 40 mg/mL fibrinogen concentration.

A custom oblong shaped punch with dimensions of 1.5 mm×5 mm was used to generate similar sized hydrogels from a large sheet of fibrin formed in a custom mold. The 1.5 mm×5 mm dimension was chosen to balance the need to cover the surface area of the macula (5 mm diameter) while maintaining a small incision to perform the implantation. With these dimensions, 3 implants could be lined up to cover >90% of the surface area of the macula while requiring a <3 mm incision. Fibrin gels punched in this geometry appeared more rigid with increasing fibrinogen concentration. Gels of varying fibrinogen concentration were lifted with forceps out of the PBS to qualitatively observe an ability to retain its shape and support its hydrated weight (FIG. 35E). The 10 mg/mL concentration gels exhibited immediate curling of the gel when removed from the PBS and folded onto itself. Gels made of 20 and 30 mg/mL fibrinogen concentrations exhibited reduced curling, and 40 mg/mL and above exhibited no curling. All gels exhibited sufficient plasticity to revert to a flat shape after being placed back in PBS. Gels made at or above 40 mg/mL fibrinogen concentration appeared pliable, durable, and maneuverable with a variety of surgical instruments. Obtaining gels from very high concentrations of fibrinogen solution can be difficult due to the high viscosity of the solution, and the highest concentration tested was 80 mg/mL. However, no observable differences on rigidity were made between gels made of 40 mg/mL and 80 mg/mL.

Figure 34C:
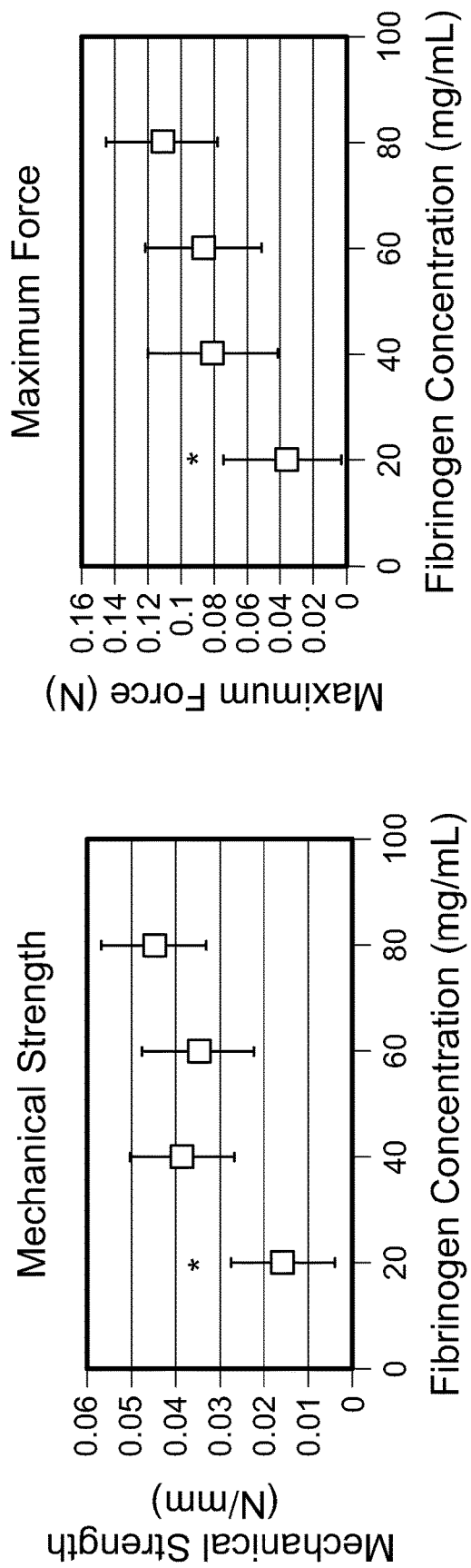
FIG. 34C shows mechanical strength and maximum force by varying the fibrinogen concentration of the fibrin hydrogel from 20-80 mg/mL.

Quantitatively, mechanical strength increased with increasing fibrinogen concentration at a fixed thickness of 300 µm (FIG. 34C). For gels made of 20, 40, 60, and 80 mg/mL fibrinogen, the mechanical strength was 0.016±0.012 N/mm, 0.039±0.011 N/mm, 0.035±0.013 N/mm, and 0.045±0.012 N/mm (n=5, p=0.003), respectively. Within groups, the 20 mg/mL concentration group was statistically different from 40 mg/mL (p=0.027) and from 80 mg/mL (p=0.006). Maximum yield force also increased with increasing fibrinogen concentration. Maximum force values for 20, 40, 60, and 80 mg/mL fibrinogen were 0.036±0.038 N, 0.081±0.039 N, 0.086±0.035 N, and 0.111±0.033 N (n=5, p=0.030), respectively. Within groups, only the 20 mg/mL concentration group was statistically different from 80 mg/mL (p=0.023).

Figure 34D:
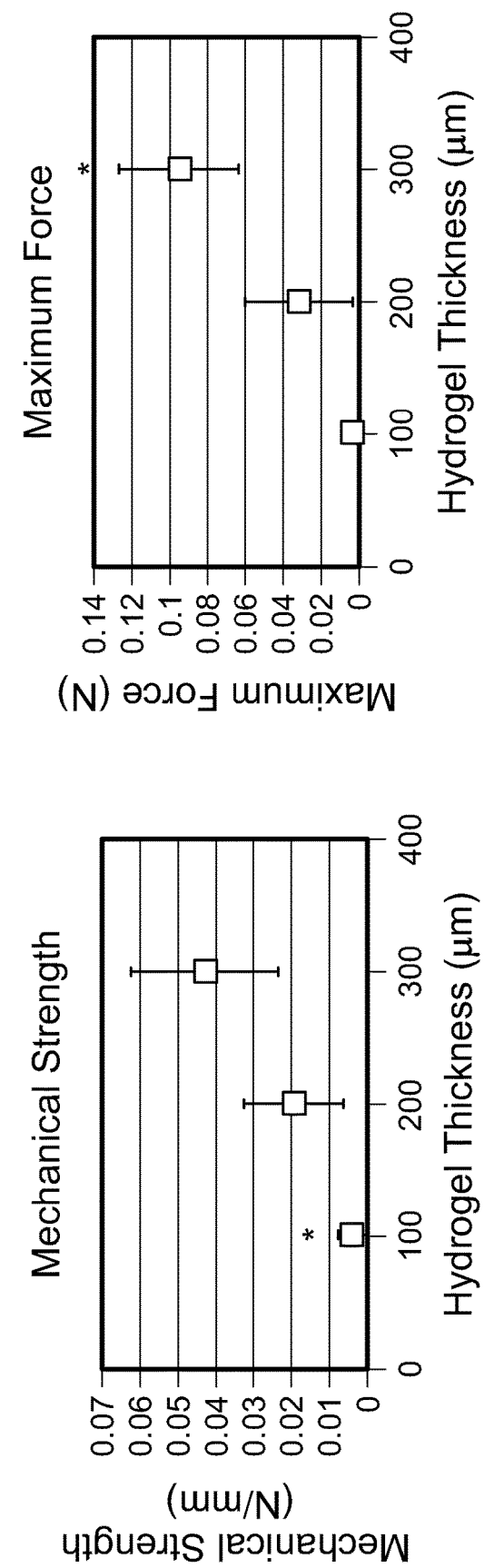
FIG. 34D shows mechanical strength and maximum force by varying the hydrogel thickness from 100-300 μm.

After casting gels in a custom mold with varying thickness spacers, the fibrin gels were punched out, imaged using OCT to quantify actual thickness, and mounted for mechanical testing. To insure proper handling of thinner gels, the fibrinogen concentration was fixed at 60 mg/mL, while varying thickness. Using OCT, the 100 µm group had an actual thickness of 91±13 µm, the 200 µm group was 198±10 µm, and the 300 µm group was 298±9 µm (n=5). Varying the thickness showed a direct exponential relationship to both mechanical strength and maximum force (FIG. 34D). A thickness of 100 µm yielded a mechanical strength of 0.004±0.003 N/mm and max force of 0.004±0.003 N, while a thickness of 200 µm yielded a mechanical strength of 0.020±0.013 N/mm and max force of 0.032±0.028 N. A thickness of 300 µm yielded a mechanical strength of 0.043±0.019 N/mm and max force of 0.094±0.031 N. There was a significant effect of thickness on mechanical strength (n=3, p=0.034), with the 100 µm group statistically different from the 300 µm group (p=0.029). Similarly, thickness had a significant effect on max force (n=3, p=0.010), with the 300 µm group significantly different from both 100 µm (p=0.009) and 200 µm (p=0.045) groups. Qualitatively, the 100 µm gels were difficult to maneuver with surgical instruments compared to both the 200 µm and 300 µm gels, as they tore easily. The 200 µm thickness appeared to be the thinnest gel with sufficient mechanical strength for surgical manipulation.

Degradation Kinetics of Fibrin Hydrogels

Figure 36A:
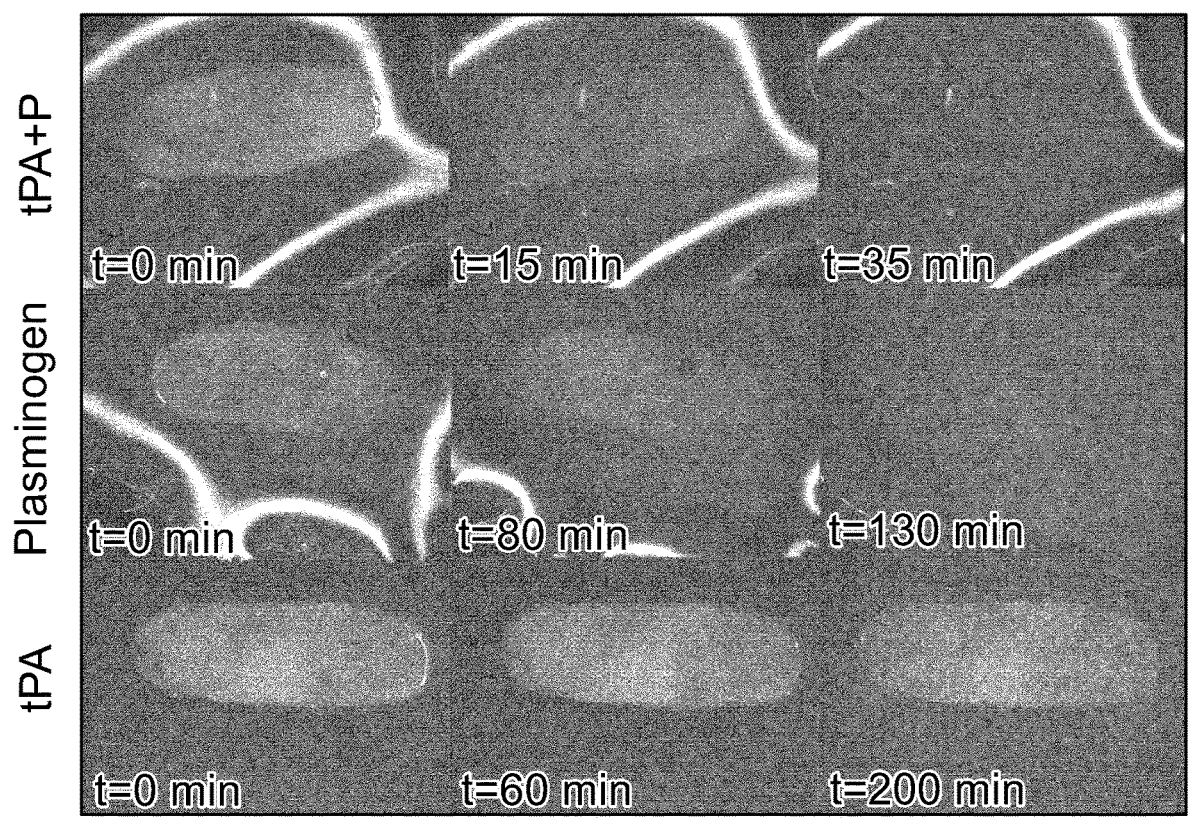
FIG. 36A contains photographs showing degradation of fibrin following treatment with tissue plasminogen activator plus plasminogen (tPA+P), plasminogen, or tPA over time.

Fibrin gels did not undergo noticeable degradation on their own when stored sterile in PBS at room temperature. To date, fibrin gels have been stored at room temperature for >9 months. Fibrin gels in PBS did not undergo noticeable degradation when exposed to tPA (FIG. 36A). However, when the combination of plasminogen and tPA was added, fibrin gels began to degrade rapidly. Degradation proceeded as an overall thinning of the gel with some gels breaking into smaller fragments. Degradation was considered complete when no visible remnants remained.

Figure 36B:
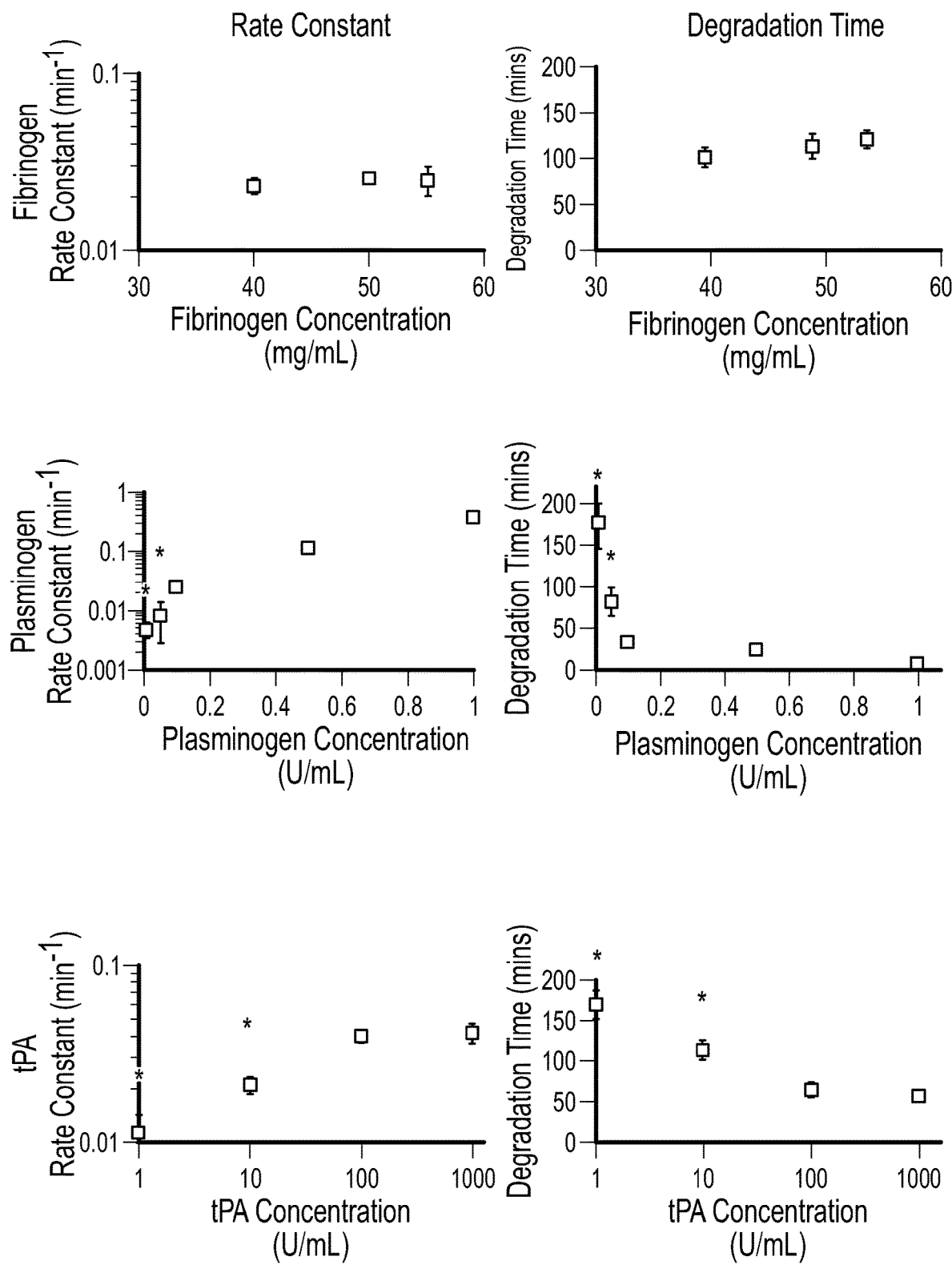
FIG. 36B contains graphs plotting the kinetics of degradation when varying fibrinogen concentrations. Plasminogen and tPA concentrations were fixed. Degradation was independent of rate constant. A linear relationship was observed graphs plotting the kinetics of degradation when varying plasminogen concentrations. Fibrinogen and tPA concentrations were fixed. Rate constant was dependent on plasminogen concentrations. A non-linear relationship was observed between plasminogen concentration and degradation time.

For degradation kinetics studies, 200 µm thick fibrin hydrogels of the same dimensions used for mechanical studies (1.5 mm×5 mm, oblong) were used. The effect of three different component concentrations (fibrinogen, plasminogen, and tPA) were studied by fixing the other two (FIG. 36B). At constant plasminogen (0.1 U/mL) and tPA concentrations (100 U/mL), kinetic rate constants for the degradation of gels produced using various fibrinogen concentrations were 0.023±0.002 $min^{-1}$ for 40 mg/mL, 0.025±0.001 $min^{-1}$ for 50 mg/mL, and 0.025±0.005 $min^{-1}$ for 55 mg/mL. There was no effect of fibrinogen concentration on the rate constant (n=3, p=0.55), suggesting zero-order kinetics. As such, degradation time was related linearly to fibrinogen concentration: 100±10 minutes for 40 mg/mL, 113±13 minutes for 50 mg/mL, and 120±10 minutes for 40 mg/mL. As no difference was detected in the mechanical stiffness of gels above 40 mg/mL, the 40 mg/mL concentration was determined to be the optimal condition for a rigid gel capable of fast degradation.

At fixed fibrinogen (40 mg/mL) and tPA concentrations (100 U/mL), plasminogen concentration variation had an effect on the degradation rate constant and total degradation time. Degradation rate constants at varying plasminogen concentrations were 0.363±0.048 $min^{-1}$ at 1 U/mL, 0.116±0.008 $min^{-1}$ at 0.5 U/mL, 0.025±0.002 $min^{-1}$ at 0.1 U/mL, 0.0083±0.0055 $min^{-1}$ at 0.05 U/mL, and 0.0048±0.0013 $min^{-1}$ at 0.01 U/mL (n=3, p<0.001). Within groups, the 1 U/mL group (P<0.001) and the 0.5 U/mL group (p<0.003) was different from all other groups. The total degradation times at varying plasminogen concentrations were 7±1 min at 1 U/mL, 24±3 min at 0.5 U/mL, 34±3 min at 0.1 U/mL, 81±16 min at 0.05 U/mL, and 177±32 min at 0.01 U/mL (n=3, p<0.001). Within groups, the 0.01 U/mL group (p<0.001) and the 0.05 U/mL (p=0.03) groups were statistically different from all other groups.

At fixed fibrinogen (40 mg/mL) and plasminogen concentrations (0.1 U/mL), degradation rate constant increased with respect to tPA concentration until reaching a plateau at 100 U/mL. Degradation rate constant values at varying tPA concentrations were 0.011±0.003 $min^{-1}$ at 1 U/mL, 0.021±0.003 $min^{-1}$ at 10 U/mL, 0.039±0.002 $min^{-1}$ at 100 U/mL, and 0.042±0.005 $min^{-1}$ at 1,000 U/mL (n=3, p<0.001). Within groups, the 1 U/mL (p=0.036) and 10 U/mL (p=0.036) groups were significantly different from all other groups. Total degradation time similarly approaches a plateau at 100 U/mL tPA concentration. Total degradation times at varying tPA concentrations were 170±17 min. at 1 U/mL, 113±12 min. at 10 U/mL, 65±9 min. at 100 U/mL, and 57±6 min. at 1,000 U/mL (n=3, p<0.001). Within groups, the 1 U/mL (p<0.001) and the 10 U/mL (p=0.004) were statistically different from all other groups.

RPE Culture on Fibrin Requires Aprotinin

Figure 37A:
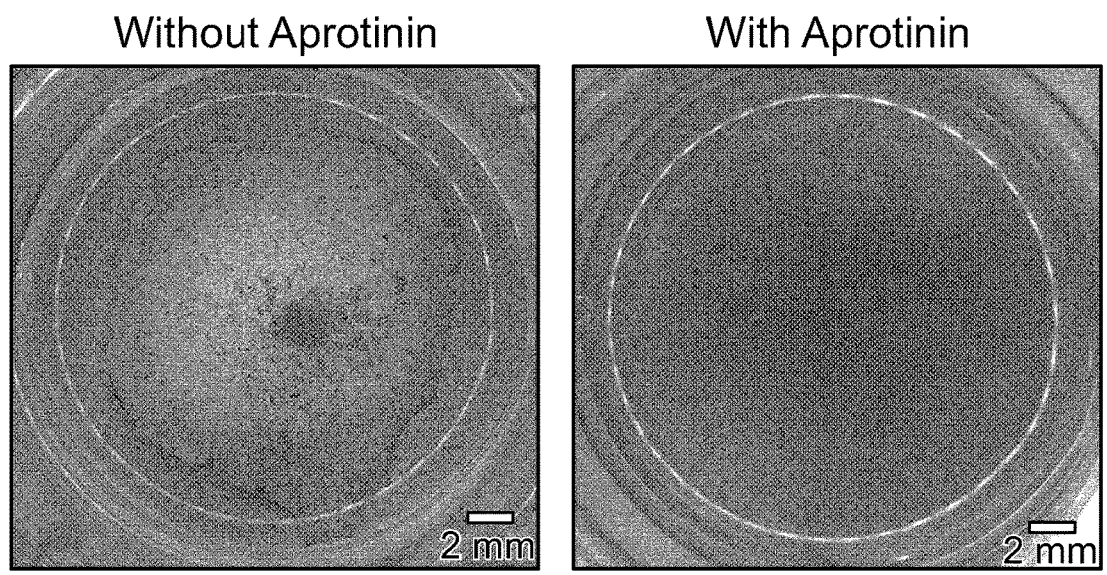
FIG. 37A shows a macroscopic view of iPSC-RPE cultured on fibrin with and without aprotinin supplement. Without aprotinin, the fibrin is degraded and the cells are unable to attach to form monolayers.

For RPE culture, fibrin gels were formed to fit various cell culture formats using a custom Teflon weight to flatten the meniscus. All cell culture was done using fibrin gels formed with 40 mg/mL fibrinogen concentration. RPE initially cultured on fibrin degraded the substrate within the first 48 hours (FIG. 37A). To address this, the protease inhibitor aprotinin was used. Aprotinin is FDA approved for use in humans.

Figure 37B:
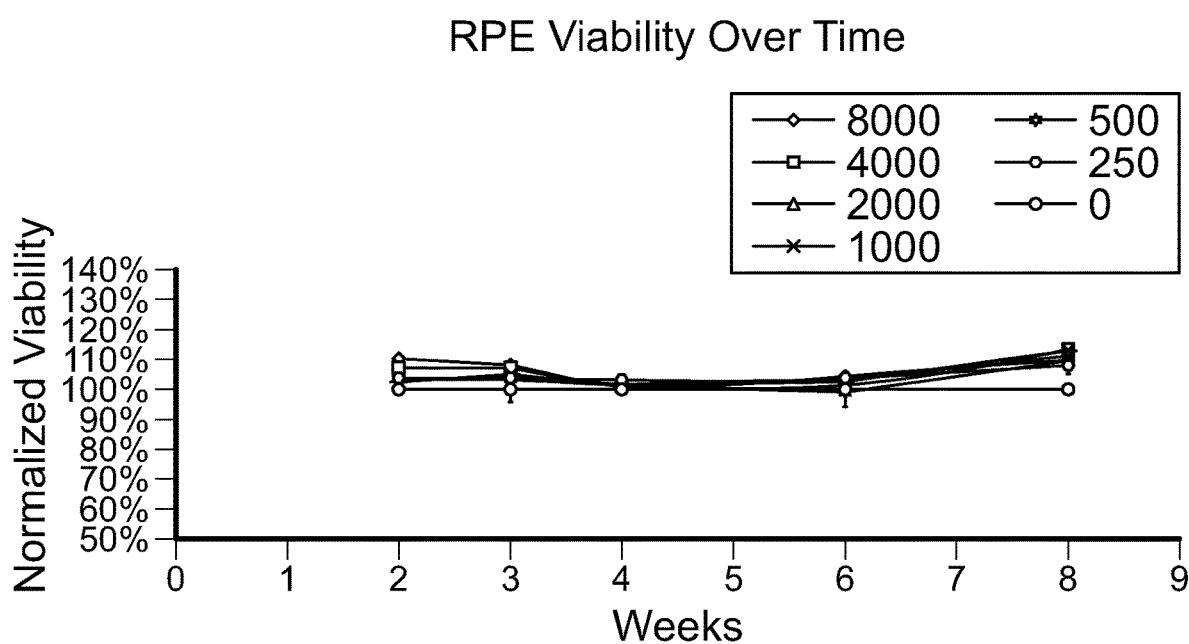
FIG. 37B shows that aprotinin, as high as 8,000 U/mL, does not show any toxicity to the iPSC-RPE.

To determine the range of aprotinin concentrations that might be useful, it was determined whether aprotinin exhibited any toxicity toward iPSC-RPE. To accomplish this, a live/dead assay was utilized on iPSC-RPE in 96-well plates. Cells were fed media supplemented with aprotinin at concentrations ranging from 250 U/mL to 8,000 U/mL (FIG. 37B) at 2 day intervals. The percentage of live cells was normalized to the percentage of live cells present in a 0 U/mL control group. Viability for all aprotinin concentrations tested did not vary from the control (FIG. 37B). Using a two-way ANOVA, no significant effect decrease in viability was observed at any concentration of aprotinin tested over the course of the 8-week experiment (n=3, p>0.999).

Figure 37C:
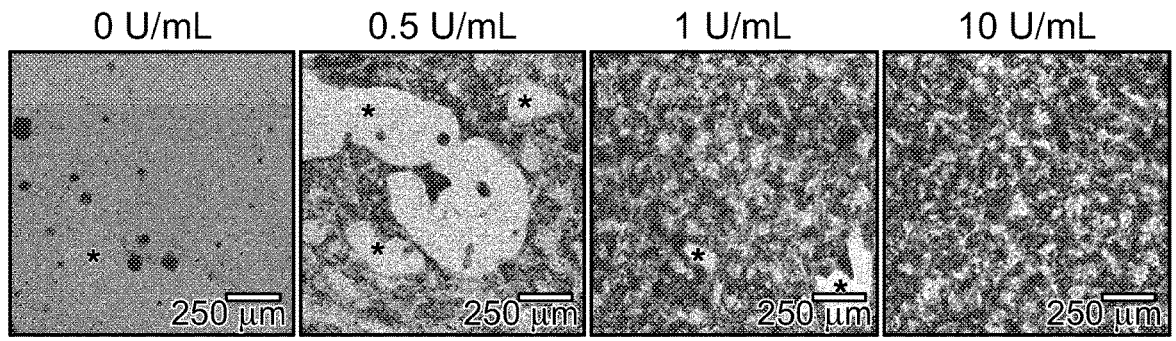
FIG. 37C shows how varying the aprotinin concentration affects iPSC-RPE monolayer formation. For example, at concentrations below 1 U/mL, the incidence of holes within the monolayer increases.

To determine the optimal amount of aprotinin necessary to maintain the fibrin support, aprotinin was added to RPE culture media at concentrations varying from 0.5 U/mL to 50 U/mL, and the survival of the fibrin hydrogel supporting an RPE monolayer was monitored qualitatively over time. After 1 week, photomicrographs were taken of various groups over the course of 8 weeks (FIG. 37C). At 0 U/mL, the majority of gel was degraded, and minimal cell attachment was observed within 2 days. Cells that attached to the surface did not form monolayers. In the 0.5 U/mL group, the majority of gel remained intact after 2 days in culture. At this concentration, iPSC-RPE cells grew over the patches in which fibrin gel remained but not in areas where the gel was degraded (FIG. 37C, asterisks). In the groups receiving 1-10 U/mL, fewer patches of degraded gel were observed with increasing aprotinin concentration.

Figure 37D:
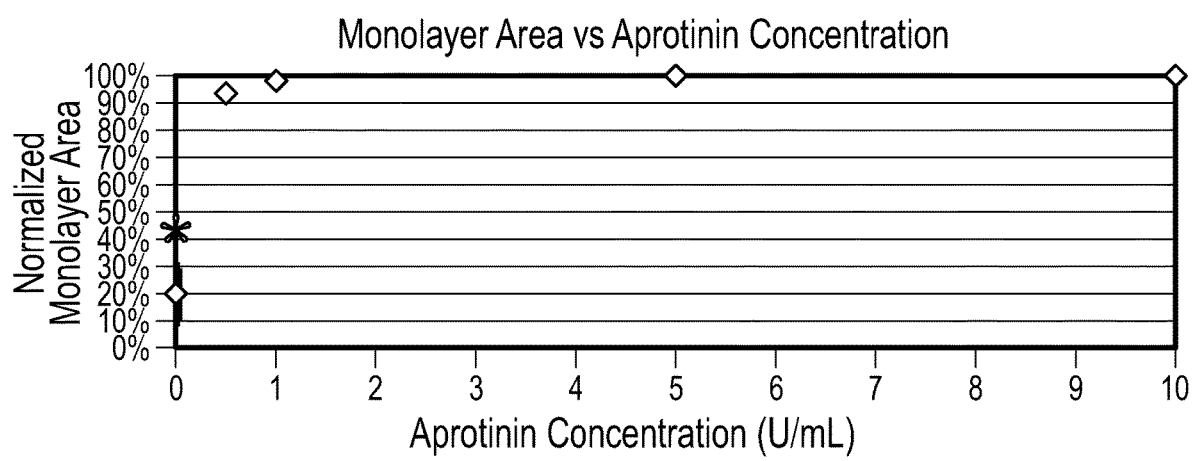
FIG. 37D shows quantification of the total iPSC-RPE monolayer at various aprotinin concentrations.

Gels exposed to aprotinin concentrations from 10 U/mL to 50 U/mL remained intact, covering the entire surface of the plate, and showed coverage with a monolayer of iPSC-RPE. Quantitatively after 1 week, the percent of surface area with cell attachment was 20.0±8.9% at 0 U/ml, 93.6±1.3% at 0.5 U/mL, 98.1±0.9% at 1 U/mL, 99.7±0.5% at 5 U/mL, and 99.8±0.2% at 10 U/mL (n=3, p<0.001; FIG. 37D). Within groups, the 0 U/mL control was significantly different from all other groups (p<0.001). Overall, the addition of 25 U/mL aprotinin prevented RPE degradation of fibrin for >8 months.

Phenotype of RPE on Fibrin iPSC-RPE cultured on fibrin are pigmented and form a cobblestone monolayer of cells (FIG. 38A). Live/dead assay confirmed that the cells were viable (FIG. 38B). Validation of the RPE phenotype was performed by qPCR using a panel of 20 key RPE markers (FIG. 40). A marker was considered present if a peak was observed prior to the $37^{th}$ cycle of PCR. Similar to what was observed for iPSC-RPE grown on matrigel coated tissue culture plastic, all RPE markers (notably, RPE65, CRALBP, and MITF) were detected in iPSC-RPE grown on fibrin gels for 10 weeks. The pluripotency marker LIN28A and markers for sendai virus delivered "Yamanaka" factors (KLF, KOS, c-myc) were negative in all groups.

Figure 38E:
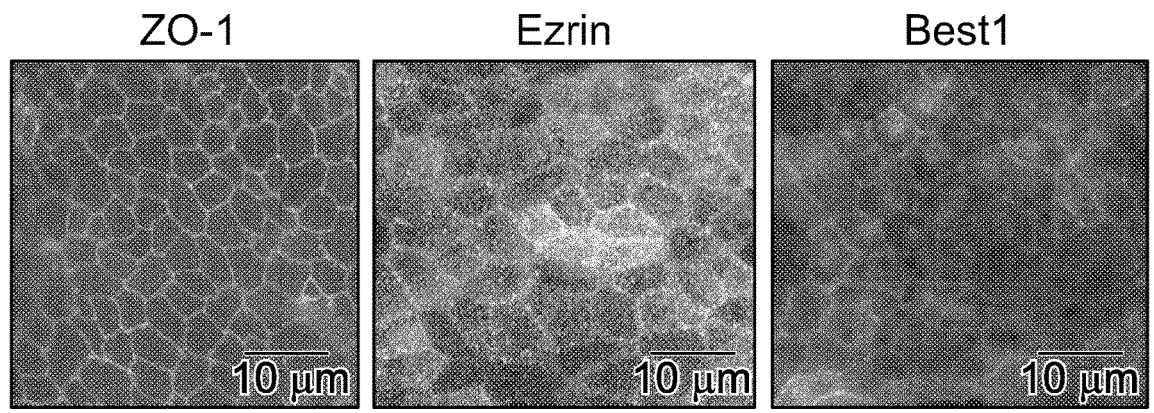
FIG. 38E shows immunofluorescent staining for Best1, Ezrin, and ZO-1.

Western blot analysis was used to confirm the protein expression of RPE markers (FIG. 38D). Bands for RPE65, Best 1, and CRALBP (normalized to α-actin) were observed in lysates from iPSC-RPE grown on fibrin gels. Immunofluorescent staining was performed for Best 1, Ezrin, and ZO-1 (FIG. 38E). Previously reported staining for Best1, Ezrin, and ZO-1 in iPSC-RPE grown on matrigel-coated transwells were used as reference (Johnson et al., *Investig. Ophthalmol. Vis. Sci.*, 56:4619 (2015)). Best1 was localized to the basolateral surface of the cells. Ezrin, a marker of microvilli, was observed as puncta on the apical surface of the cells indicative of microvilli. ZO-1 was observed to outline the borders of all cells indicating the presence of junctional complexes and a single monolayer.

RPE secretion of VEGF and PEDF was quantified by ELISA (FIG. 38C). After 48 hours of culture with RPE, the media from the fibrin group had a VEGF concentration of 6.46±0.23 ng/mL. For PEDF, the fibrin group had a concentration of 6.41±1.61 µg/mL, and the matrigel control had 6.10±0.53 µg/mL (n=3, p=0.822). Thus, no differences were noted between RPE grown on fibrin hydrogels or tissue culture plastic.

Figure 42A:
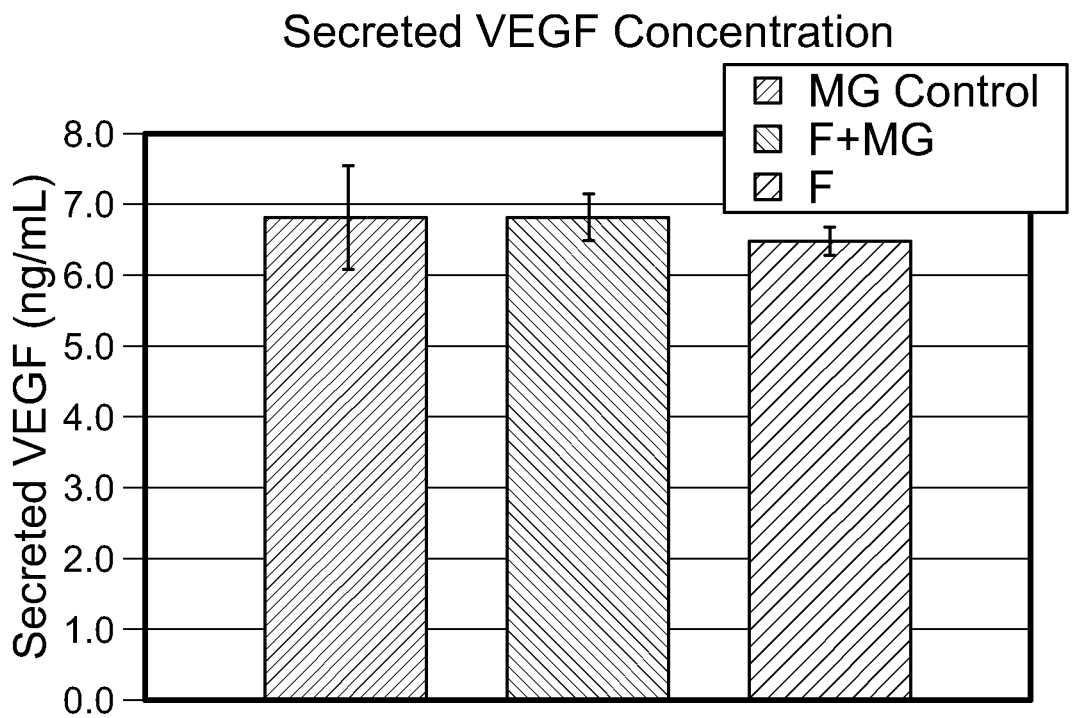
FIG. 42A is a graph comparing VEGF release from fibrin (F), fibrin plus matrigel, and matrigel control.
Figure 42B:
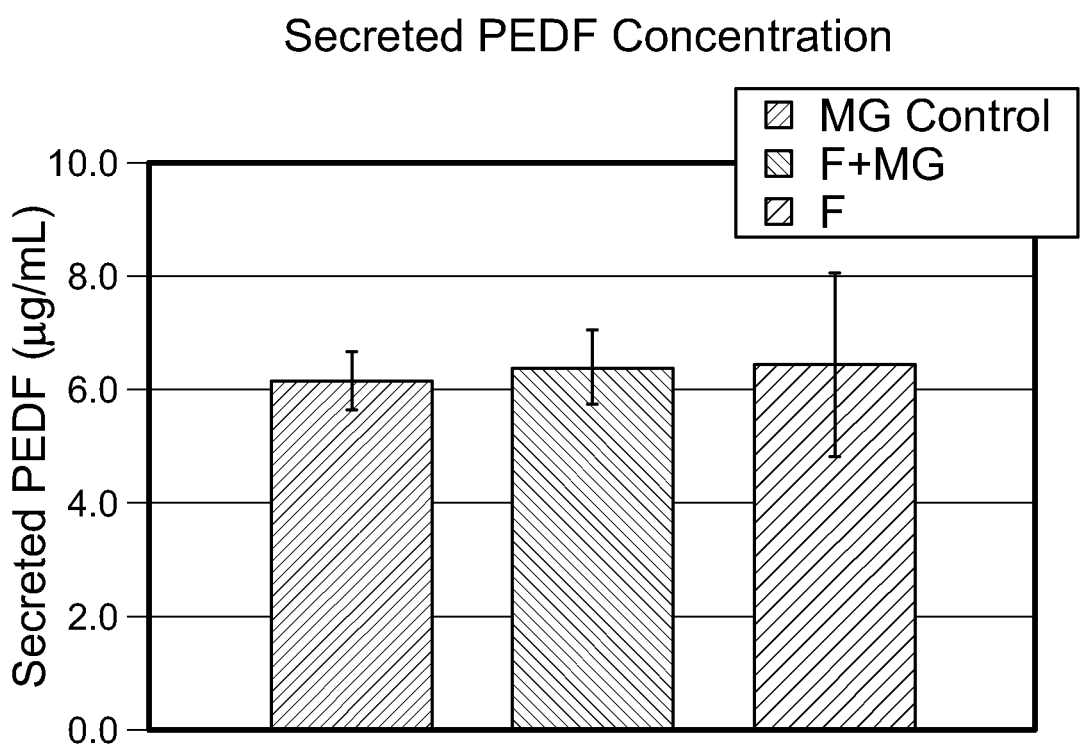
FIG. 42B is a graph comparing PEDF release from fibrin (F), fibrin plus matrigel, and matrigel control. The secretion of both growth factors was similar between all three samples.
Figure 43:
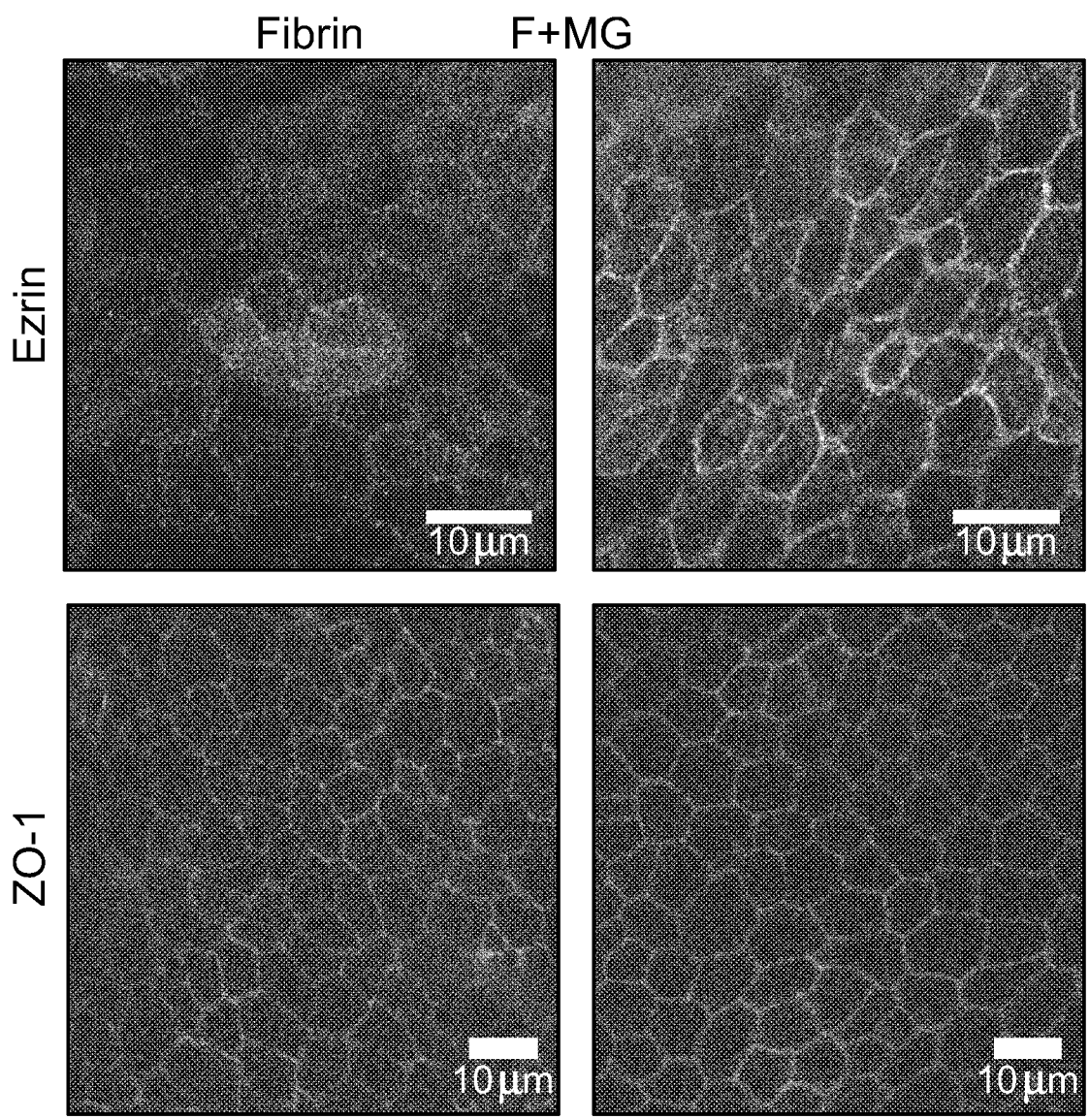
FIG. 43 contains images of immunofluorescent staining for Ezrin and Zo-1 with iPSC-RPE grown on fibrin or fibrin plus matrigel (F+MG). Both groups exhibited positive, characteristic staining patterns.
Figure 44:
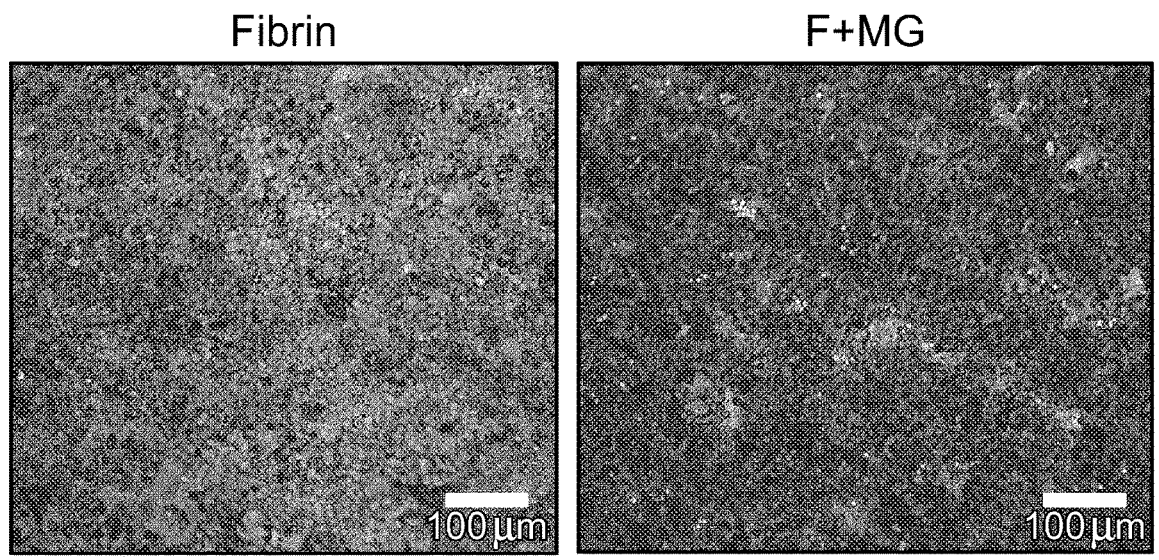
FIG. 44 contains images of live/dead assay with iPSC-RPE grown on fibrin or fibrin plus matrigel (F+MG). Cell viability was similar between the groups.
Figure 45:
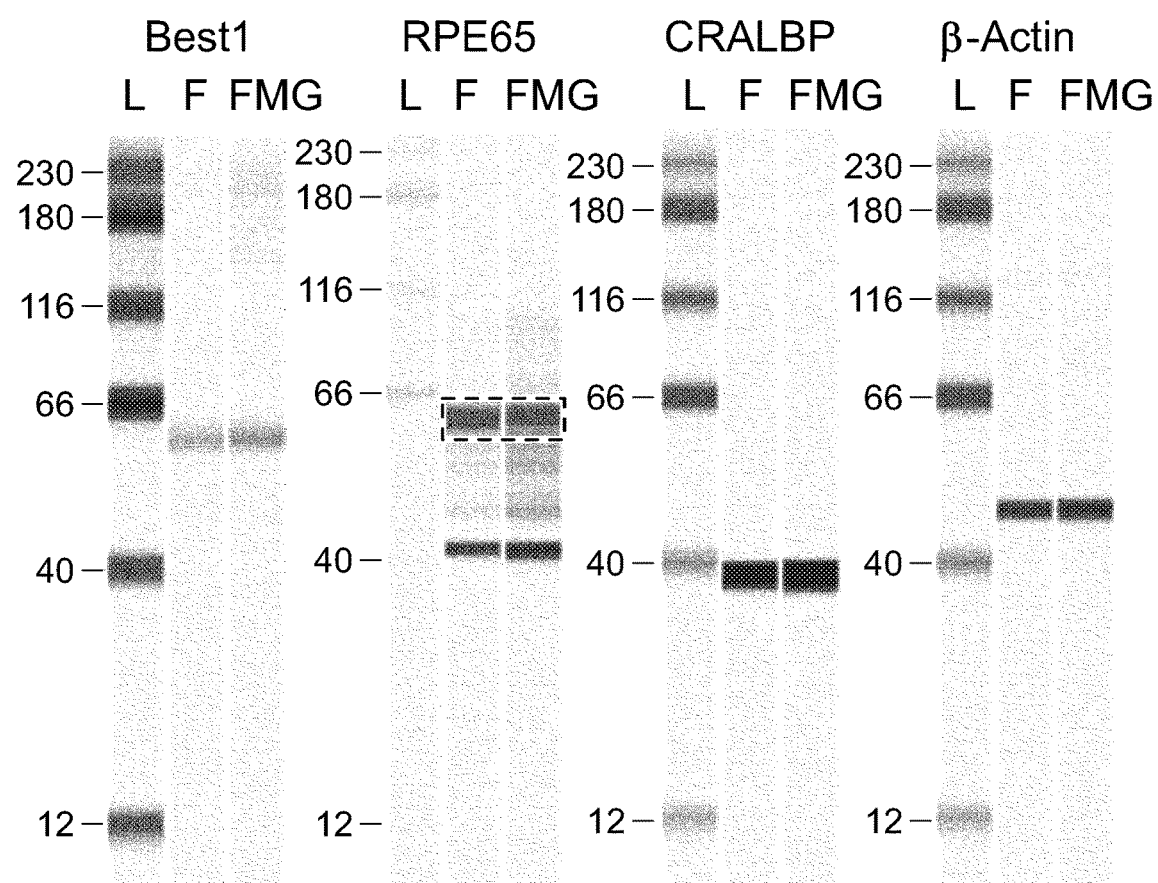
FIG. 45 contains an image of a Western blot analysis for Best1, RPE65, CRALBP, and B-actin with iPSC-RPE grown on fibrin (F) or fibrin plus matrigel (FMG). L is the size ladder. Best1, RPE65, and CRALBP are RPE markers.

Similar results were obtained culturing iPSC-RPE on matrigel-coated fibrin hydrogels. For example, ELISA quantification of VEGF and PEDF showed similar release of iPSC-RPE cultured on fibrin+matrigel coating to both fibrin hydrogels alone and matrigel-coated TCPS (FIG. 42). Immunofluorescent staining showed similar patterns of Ezrin and ZO-1 between iPSC-RPE cultured on fibrin or fibrin+matrigel coating (FIG. 43). Live/Dead assay showed similar viability of iPSC-RPE grown on fibrin or fibrin+matrigel (FIG. 44). Western blot analysis showed expression of Best1, RPE65 and CRALBP from iPSC-RPE grown on fibrin or fibrin+matrigel (FIG. 45).

Degradation of Fibrin Leaves an Intact RPE Monolayer

Figure 39A:
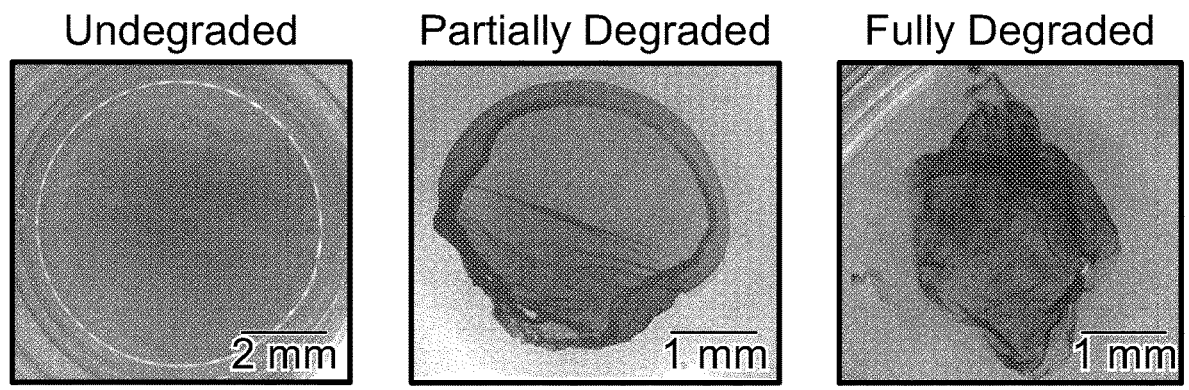
FIG. 39A contains images of a plate containing iPSC-RPE cells cultured on a fibrin gel, which was then degraded with 0.1 U/mL plasminogen and 22 U/mL tissue plasminogen activator (tPA) over time. The cells detached from the plates as a monolayer and formed wrinkles and folds.

The purpose of this study was to generate a rapidly degradable support for the growth and transplantation of an RPE monolayer. Having established parameters to produce fibrin hydrogels that are rapidly degradable and of appropriate size and mechanical strength, the following was performed to determine whether the presence of an iPSC-RPE monolayer and growth in aprotinin altered the degradation kinetics of the gels and whether degradation altered the viability of the iPSC-RPE in vitro. Based on the data accumulated using gels sans iPSC-RPE, degradation studies were performed using 0.5 U/mL plasminogen and 100 U/mL tPA. As shown in FIG. 39A as the fibrin began to degrade, the RPE monolayer began curling onto itself from the edges (FIG. 39A). Wrinkles were seen in regions where no fibrin support remained. In regions with fibrin still intact, the RPE appeared flat. Once fully degraded, the RPE remained as a monolayer sheet, with many curls and wrinkles, and it became difficult to handle with surgical instruments. However, the RPE appeared as a continuous, pigmented tissue (FIG. 39A).

Figure 39B:
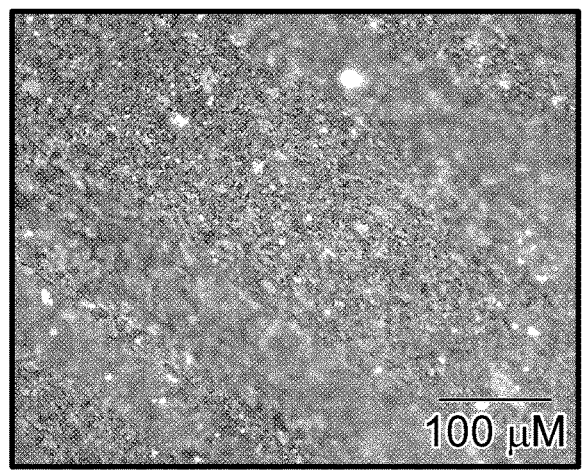
FIG. 39B is shows live/dead assay of iPSC-RPE after fibrin gel had been completely degraded.
Figure 39C:
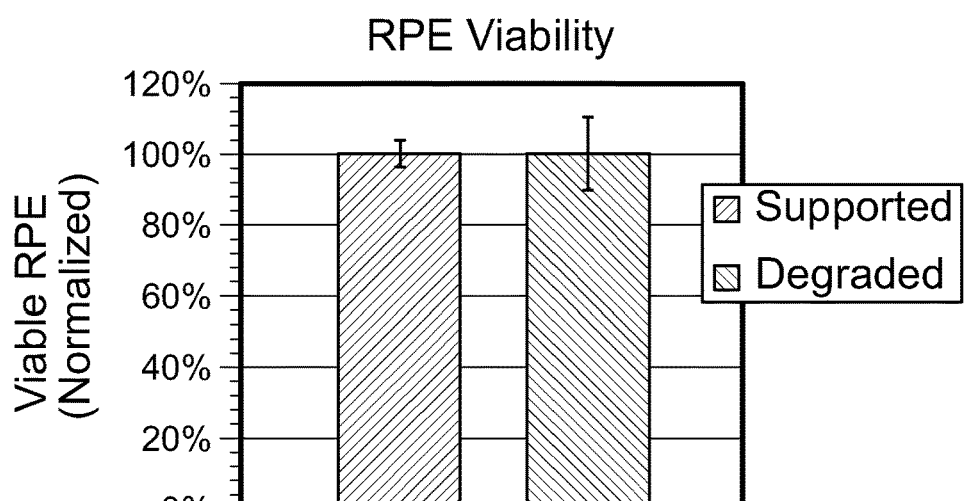
FIG. 39C is a graph showing quantitative iPSC-RPE viability before and after fibrin degradation.

To confirm the viability of the RPE after the fibrin support was degraded, a live/dead assay was performed 24 hours after the fibrin was completely degraded (FIGS. 39B and 39C). Viability was normalized to percent of viable RPE cultured on fibrin prior to degradation. The normalized viability values for RPE prior to degradation were 100.0±3.9% and following degradation were 101.1±10.5% (n=3, p=0.877).

Figure 39D:
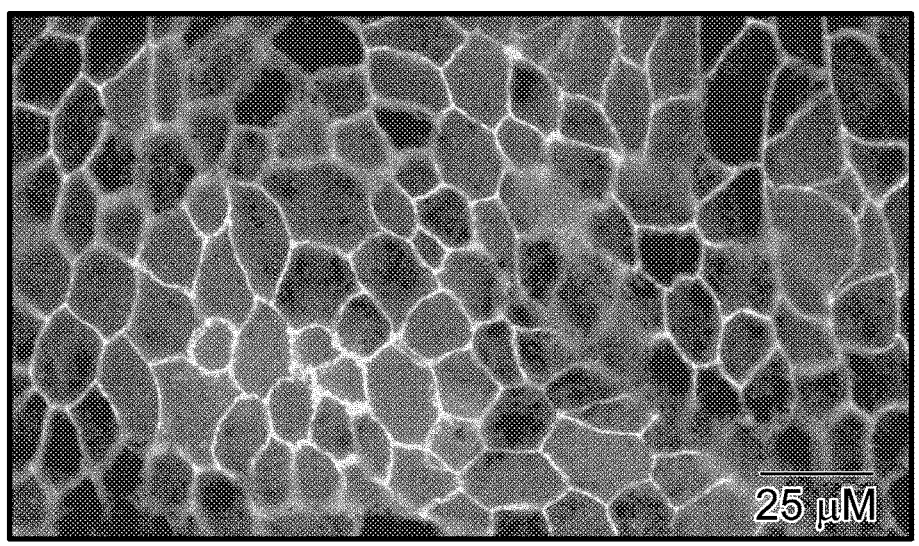
FIG. 39D is an immunofluorescent stain of ZO-1 in iPSC-RPE monolayer after fibrin was fully degraded, showing the retention of the monolayer.

Finally, immunofluorescence was utilized to detect ZO-1 presence after fibrin degradation (FIG. 39D). 24 hours after complete fibrin degradation, fixed RPE monolayers exhibited positive staining for ZO-1. Staining of the unsupported RPE monolayer was indistinguishable from that of monolayers on undegraded fibrin.

While certain results provided herein were obtained using iPSC-derived RPE, there is no reason why the fibrin hydrogel materials described herein could not be used for RPE derived from other sources such as ESCs and adult stem cells.

The results provided herein demonstrate that fibrin can be used as a material for RPE transplantation. Fibrin can be formed in a variety of shapes and sizes, with mechanical stiffness and degradation properties appropriate for RPE delivery. The results provided herein also demonstrate that a protease inhibitor such as aprotinin can be used to slow the ability of RPE to degrade the fibrin. In addition, when iPSC-RPE are cultured on fibrin in the presence of a protease inhibitor such as aprotinin, the cells can appear phenotypically similar to RPE. After the fibrin is degraded, the RPE can remain as a viable monolayer.

Example 7—Implanting a Fibrin Hydrogel Containing a RPE Monolayer

Figure 41:
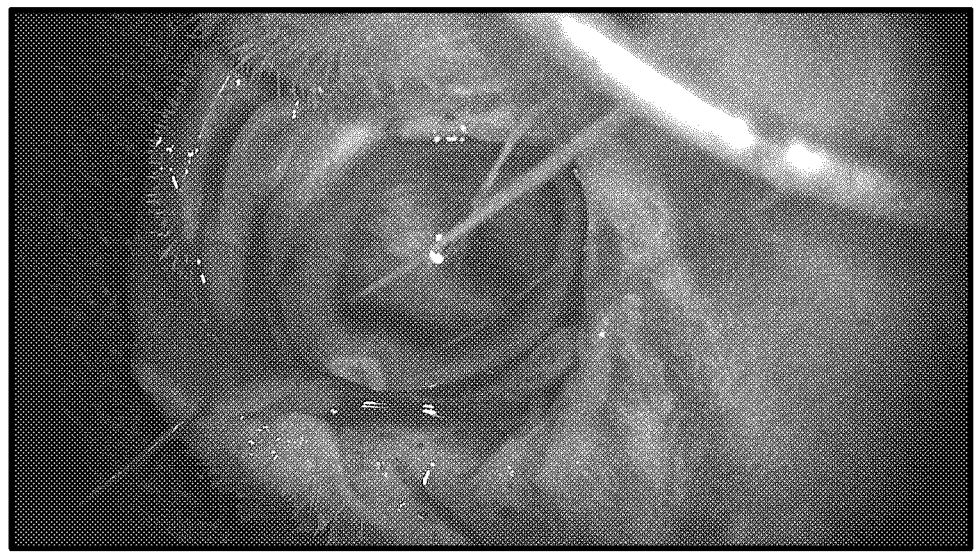
FIG. 41 is a photograph of a fibrin hydrogel implanted into the subretinal space of a rabbit eye. No evidence of the fibrin hydrogel was observed in the eye after 48 hours.

A fibrin hydrogel was implanted into the subretinal space of a rabbit eye (FIG. 41). The fibrin hydrogel was prepared by mixing fibrinogen (final: 40 mg/mL) and thrombin (final: 100 U/mL) solutions in a custom mold to generate a thin sheet (200 µm). A small volume of trypan blue was added to make the gel easier to visualize after implantation. Implants were punched to a 1.5 mm×5 mm oblong geometry. Once prepared, the implant was loaded into an implantation device. To perform the surgical implantation, a white female New Zealand rabbit (3 kg) was anesthetized and prepped for surgery. A standard 3-port vitrectomy was performed, followed by bleb formation using a fine cannula, and a retinotomy was created using retinal scissors. A 3.2 mm slit knife was used to create an incision through the sclera. The implantation device was inserted into the eye and positioned under the retinotomy. The implant was deployed into place. After the implantation device removed, the scleral incision was sutured closed. Prior to the animal awakening, the implant could be seen as a flat sheet under a flattened retina. The animal was sacrificed after 48 hours, and the eye was harvested. Gross dissection examination revealed no remaining evidence of the fibrin hydrogel.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A retinal implant comprising (a) a retinal pigment epithelium monolayer having an apical surface and a basal surface and that is a flat, wrinkle-free monolayer, and (b) a fibrin hydrogel layer directly attached to said basal surface of said monolayer, wherein said apical surface is free of a fibrin hydrogel layer, wherein said retinal implant lacks patches of degraded fibrin hydrogel within said fibrin hydrogel layer, and wherein said fibrin hydrogel layer degrades when said retinal implant is implanted into an eye of a mammal.

2. The implant of claim 1, wherein said fibrin hydrogel layer is from about 20 µm to about 400 µm thick.

3. The implant of claim 1, wherein said implant comprises plasminogen.

4. The implant of claim 1, wherein said implant comprises from about 0.1 U of plasminogen per mL to about 40 U of plasminogen per mL or from about 0.001 U of plasminogen per mL to about 40 U of plasminogen per mL.

5. A method for making a retinal implant, wherein said method comprises culturing retinal epithelial cells directly on a fibrin basal support substrate in a medium comprising a protease inhibitor or an anti-fibrinolytic agent to form a retinal pigment epithelium monolayer having an apical surface and a basal surface, wherein said basal surface is closer to said fibrin basal support substrate than said apical surface, wherein said apical surface is free of said fibrin basal support substrate, wherein said retinal implant lacks patches of degraded fibrin hydrogel within said fibrin hydrogel layer, wherein said fibrin hydrogel layer degrades when said retinal implant is implanted into an eye of a mammal, and wherein said retinal pigment epithelium monolayer is a flat, wrinkle-free monolayer.

6. The method of claim 5, wherein said fibrin basal support substrate is from about 20 µm to about 400 µm thick.

7. The method of claim 5, wherein said fibrin basal support substrate comprises from about 20 mg of fibrinogen per mL to about 80 mg of fibrinogen per mL.

8. The method of claim 5, wherein said fibrin basal support substrate comprises from about 2 U of thrombin per mL to about 1500 U of thrombin per mL.

9. The method of claim 5, wherein said fibrin basal support substrate comprises from about 0.1 U of plasminogen per mL to about 40 U of plasminogen per mL or from about 0.001 U of plasminogen per mL to about 40 U of plasminogen per mL.

10. The method of claim 5, wherein said medium comprises said protease inhibitor, and said protease inhibitor is aprotinin.

11. The method of claim 10, wherein said medium comprises from about 5 U of aprotinin per mL to about 500 U of aprotinin per mL.

12. The method of claim 5, wherein said medium comprises said anti-fibrinolytic agent, and said antifibrinolytic agent is transexamic acid or aminocaproic acid.

13. The method of claim 5, wherein said medium further comprises plasminogen.

14. The method of claim 13, wherein said medium comprises from about 0.1 U of plasminogen per mL to about 40 U of plasminogen per mL or from about 0.001 U of plasminogen per mL to about 40 U of plasminogen per mL.

15. The method of claim 5, wherein said method further comprises culturing endothelial cells on said fibrin basal support substrate.

16. The method of claim 15, wherein said endothelial cells were obtained from a source selected from the group consisting of iPSC-derived endothelial cells, blood outgrowth endothelial cells (BOEC), endothelial colony-forming cells (ECFCs), endothelial progenitor cells (EPCs), and umbilical vein endothelial cells (UVEC).

17. The method of claim 5, wherein said method further comprises culturing sub-RPE tissue cell populations on said fibrin basal support substrate.

18. The method of claim 17, wherein said sub-RPE tissue cell populations comprise melanocytes, pericytes, or fibroblasts.

\* \* \* \* \*